United States Patent
Rogers et al.

(10) Patent No.: US 8,623,028 B2
(45) Date of Patent: Jan. 7, 2014

(54) SURGICAL PORT FEATURE

(75) Inventors: Theodore W. Rogers, Alameda, CA (US); Craig R. Gerbi, Half Moon Bay, CA (US); John Ryan Steger, Sunnyvale, CA (US); Charles E. Swinehart, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 461 days.

(21) Appl. No.: 12/618,621

(22) Filed: Nov. 13, 2009

(65) Prior Publication Data
US 2011/0071473 A1      Mar. 24, 2011

Related U.S. Application Data

(63) Continuation-in-part of application No. 12/618,549, filed on Nov. 13, 2009, now abandoned.

(60) Provisional application No. 61/245,171, filed on Sep. 23, 2009.

(51) Int. Cl.
*A61M 29/00*      (2006.01)

(52) U.S. Cl.
USPC ........................................................ 606/108

(58) Field of Classification Search
USPC ............. 600/114, 115; 604/164.04, 174, 539; 606/108
See application file for complete search history.

(56) References Cited

U.S. PATENT DOCUMENTS

| | | | |
|---|---|---|---|
| 4,616,631 A | 10/1986 | Takahashi | |
| 4,678,459 A | 7/1987 | Onik et al. | |
| 4,863,430 A | 9/1989 | Klyce et al. | |
| 5,269,772 A | 12/1993 | Wilk | |
| 5,402,793 A | 4/1995 | Gruner et al. | |
| 5,507,758 A * | 4/1996 | Thomason et al. | 606/148 |
| 5,797,835 A | 8/1998 | Green | |

(Continued)

FOREIGN PATENT DOCUMENTS

| | | |
|---|---|---|
| EP | 1334700 A1 | 8/2003 |
| EP | 1870043 A2 | 12/2007 |

(Continued)

OTHER PUBLICATIONS

PCT/US2010/056203 International Search Report and Written Opinion of the International Searching Authority, mailed Jul. 13, 2011, 15 pages.

(Continued)

*Primary Examiner* — Kathleen Holwerda
*Assistant Examiner* — Sarah W Aleman

(57) ABSTRACT

A robotic surgical system is configured with rigid, curved cannulas that extend through the same opening into a patient's body. Surgical instruments with passively flexible shafts extend through the curved cannulas. The cannulas are oriented to direct the instruments towards a surgical site. Various port features that support the curved cannulas within the single opening are disclosed. In one aspect, surgical instrument channels extend at different angles between top and bottom surfaces of a port feature. In another aspect, a funnel portion and a tongue portion are separated by a waist portion, and surgical instrument channels extend from the funnel portion through the waist portion. Cannula support fixtures that support the cannulas during insertion into the single opening and mounting to robotic manipulators are disclosed. A teleoperation control system that moves the curved cannulas and their associated instruments in a manner that allows a surgeon to experience intuitive control is disclosed.

41 Claims, 41 Drawing Sheets

(56) References Cited

U.S. PATENT DOCUMENTS

| | | |
|---|---|---|
| 6,331,181 B1 | 12/2001 | Tierney et al. |
| 6,508,759 B1 * | 1/2003 | Taylor et al. ................ 600/168 |
| 6,551,270 B1 * | 4/2003 | Bimbo et al. ................ 604/264 |
| 6,821,285 B2 | 11/2004 | Laufer et al. |
| 6,913,609 B2 * | 7/2005 | Yencho et al. ........... 604/167.01 |
| 7,066,926 B2 | 6/2006 | Wallace et al. |
| 7,070,602 B2 | 7/2006 | Smith et al. |
| 7,833,156 B2 | 11/2010 | Williams et al. |
| 7,854,738 B2 | 12/2010 | Lee et al. |
| 7,942,885 B2 | 5/2011 | Sixto, Jr. et al. |
| 7,988,679 B2 * | 8/2011 | Daly et al. ................ 604/537 |
| 8,037,591 B2 | 10/2011 | Spivey et al. |
| 8,114,097 B2 | 2/2012 | Brock et al. |
| 8,187,229 B2 | 5/2012 | Weitzner et al. |
| 8,287,554 B2 | 10/2012 | Cerier et al. |
| 2001/0021859 A1 | 9/2001 | Kawai et al. |
| 2002/0040226 A1 | 4/2002 | Laufer et al. |
| 2002/0138082 A1 | 9/2002 | Brock et al. |
| 2002/0198537 A1 | 12/2002 | Smith et al. |
| 2004/0010245 A1 | 1/2004 | Cerier et al. |
| 2005/0043718 A1 | 2/2005 | Madhani et al. |
| 2005/0182386 A1 | 8/2005 | Aggerholm |
| 2006/0074406 A1 | 4/2006 | Cooper et al. |
| 2006/0111615 A1 | 5/2006 | Danitz et al. |
| 2006/0124134 A1 | 6/2006 | Wood et al. |
| 2006/0247500 A1 * | 11/2006 | Voegele et al. ............ 600/208 |
| 2006/0247673 A1 | 11/2006 | Voegele et al. |
| 2006/0270911 A1 * | 11/2006 | Voegele et al. ............ 600/235 |
| 2006/0293643 A1 | 12/2006 | Wallace et al. |
| 2007/0027458 A1 | 2/2007 | Sixto, Jr. et al. |
| 2007/0049966 A1 | 3/2007 | Bonadio et al. |
| 2007/0208312 A1 * | 9/2007 | Norton et al. ................ 604/284 |
| 2007/0239106 A1 | 10/2007 | Weitzner et al. |
| 2007/0282266 A1 | 12/2007 | Davidson |
| 2008/0027476 A1 | 1/2008 | Piskun |
| 2008/0065105 A1 | 3/2008 | Larkin et al. |
| 2008/0065107 A1 | 3/2008 | Larkin et al. |
| 2008/0065111 A1 | 3/2008 | Blumenkranz et al. |
| 2008/0071288 A1 | 3/2008 | Larkin et al. |
| 2008/0177283 A1 | 7/2008 | Lee et al. |
| 2008/0188986 A1 | 8/2008 | Hoppe |
| 2008/0255519 A1 | 10/2008 | Piskun et al. |
| 2008/0255585 A1 | 10/2008 | Gerbi et al. |
| 2008/0269562 A1 | 10/2008 | Marescaux et al. |
| 2009/0012477 A1 * | 1/2009 | Norton et al. ................ 604/264 |
| 2009/0062602 A1 | 3/2009 | Rosenberg et al. |
| 2009/0093752 A1 | 4/2009 | Richard et al. |
| 2009/0149936 A1 | 6/2009 | Lentz |
| 2009/0157076 A1 | 6/2009 | Athas et al. |
| 2009/0187079 A1 | 7/2009 | Albrecht et al. |
| 2009/0192444 A1 | 7/2009 | Albrecht et al. |
| 2009/0216234 A1 | 8/2009 | Farr et al. |
| 2009/0227843 A1 | 9/2009 | Smith et al. |
| 2009/0270676 A1 | 10/2009 | Sicvol |
| 2010/0063452 A1 | 3/2010 | Edelman et al. |
| 2010/0081871 A1 | 4/2010 | Widenhouse et al. |
| 2010/0081881 A1 | 4/2010 | Murray et al. |
| 2010/0081883 A1 | 4/2010 | Murray et al. |
| 2010/0100043 A1 | 4/2010 | Racenet |
| 2010/0113886 A1 | 5/2010 | Piskun et al. |
| 2010/0204713 A1 | 8/2010 | Ruiz |
| 2010/0228091 A1 | 9/2010 | Widenhouse et al. |
| 2010/0249523 A1 | 9/2010 | Spiegal et al. |
| 2010/0249524 A1 | 9/2010 | Ransden et al. |
| 2010/0312063 A1 | 12/2010 | Hess et al. |
| 2011/0028793 A1 | 2/2011 | Martin et al. |
| 2011/0071347 A1 | 3/2011 | Rogers et al. |
| 2011/0071541 A1 | 3/2011 | Prisco et al. |
| 2011/0071542 A1 | 3/2011 | Prisco et al. |
| 2011/0071543 A1 | 3/2011 | Prisco et al. |
| 2011/0071544 A1 | 3/2011 | Steger et al. |
| 2011/0125165 A1 | 5/2011 | Simaan et al. |

FOREIGN PATENT DOCUMENTS

| | | |
|---|---|---|
| EP | 2047805 A1 | 4/2009 |
| WO | WO9712557 A1 | 4/1997 |
| WO | WO9712558 A1 | 4/1997 |
| WO | WO2006100658 A2 | 9/2006 |
| WO | WO2008045350 A2 | 4/2008 |
| WO | WO2008103151 A2 | 8/2008 |
| WO | WO20080157225 A1 | 12/2008 |
| WO | WO2009080399 A2 | 7/2009 |
| WO | WO2009102102 A1 | 8/2009 |
| WO | WO2009120944 A2 | 10/2009 |
| WO | WO2010041900 A2 | 4/2010 |

OTHER PUBLICATIONS

PCT/US10/56193 International Search Report and Written Opinion of the International Searching Authority, mailed Jun. 1, 2011, 19 pages.
PCT/US10/56193 Invitation to Pay Additional Fees with Results of the Partial International Search, mailed Apr. 8, 2011, 7 pages.
PCT/US10/56203 Invitation to Pay Additional Fees with Results of the Partial International Search, mailed Apr. 8, 2011, 4 pages.
PCT/US10/46948 International Search Report and Written Opinion of the International Searching Authority, mailed Nov. 26, 2010, 11 pages.
PCT/US10/56173 International Search Report and Written Opinion of the International Searching Authority, mailed Apr. 5, 2011, 13 pages.
PCT/US10/56188 International Search Report and Written Opinion of the International Searching Authority, mailed Apr. 5, 2011, 14 pages.
Final Office Action mailed Dec. 5, 2012 for U.S. Appl. No. 12/618,598, filed Nov. 13, 2009.
Final Office Action mailed Nov. 13, 2012 for U.S. Appl. No. 12/618,631, filed Nov. 13, 2009.
Non-Final Office Action mailed Dec. 6, 2012 for U.S. Appl. No. 12/618,608, filed Nov. 13, 2009.
Decision on Petition mailed Mar. 12, 2013 for U.S. Appl. No. 12/618,608, filed Nov. 13, 2009.
Final office action mailed Apr. 5, 2013 for U.S. Appl. No. 12/618,608, filed Nov. 13, 2009.
Final Office Action mailed Jan. 25, 2013 for U.S. Appl. No. 12/618,583, filed Nov. 13, 2009.
Requirement for Restriction and Election mailed Sep. 19, 2012 for U.S. Appl. No. 12/618,608, filed Nov. 13, 2009.
Requirement for Restriction and Election mailed Feb. 21, 2012 for U.S. Appl. No. 12/618,631, filed Nov. 13, 2009.
Interview Summary mailed Oct. 10, 2012 for U.S. Appl. No. 12/618,631, filed Nov. 13, 2009.
Interview Summary mailed Sep. 11, 2012 for U.S. Appl. No. 12/618,583, filed Nov. 13, 2009.
Interview Summary mailed Sep. 11, 2012 for U.S. Appl. No. 12/618,598, filed Nov. 13, 2009.
Office Action mailed Jul. 5, 2012 for U.S. Appl. No. 12/618,583, filed Nov. 13, 2009.
Office Action mailed Jul. 10, 2012 for U.S. Appl. No. 12/618,631, filed Nov. 13, 2009.
Office Action mailed Jun. 22, 2012 for U.S. Appl. No. 12/618,598, filed Nov. 13, 2009.

* cited by examiner

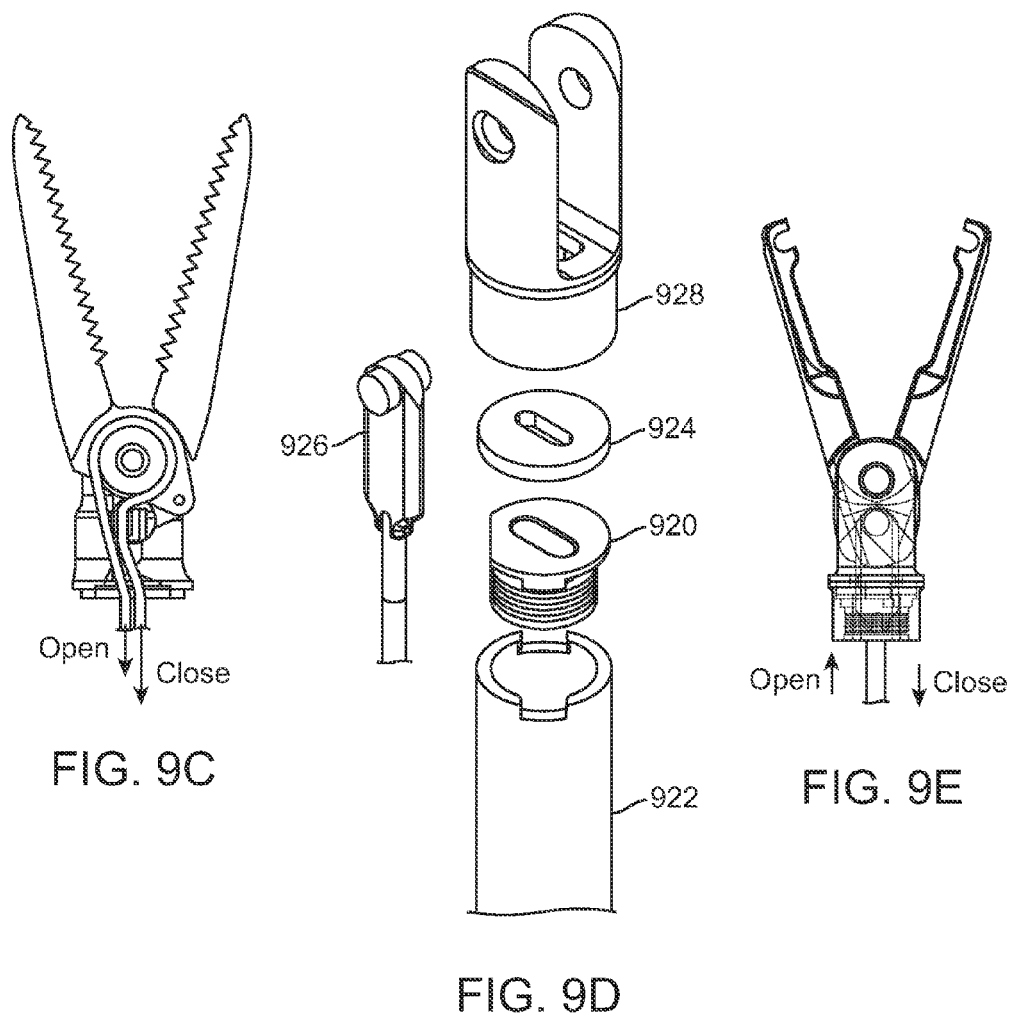

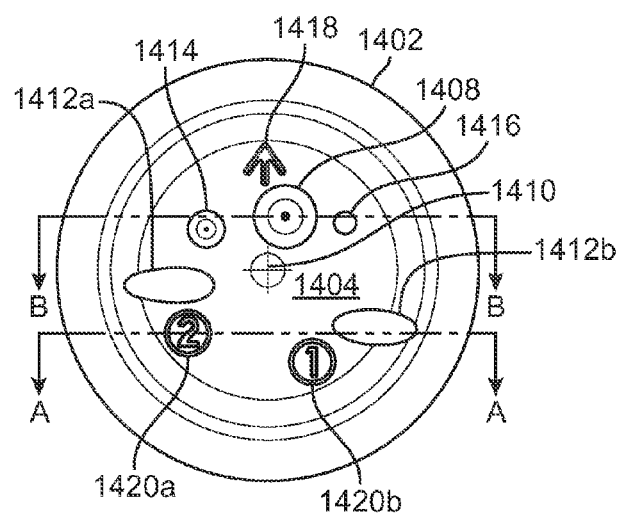
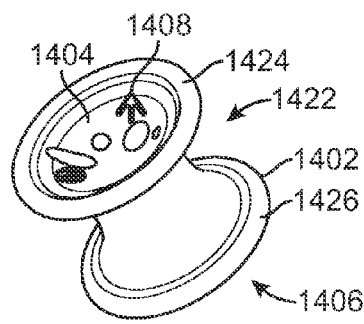
FIG. 14A    FIG. 14B
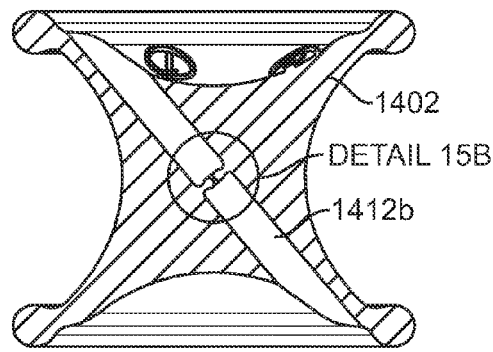
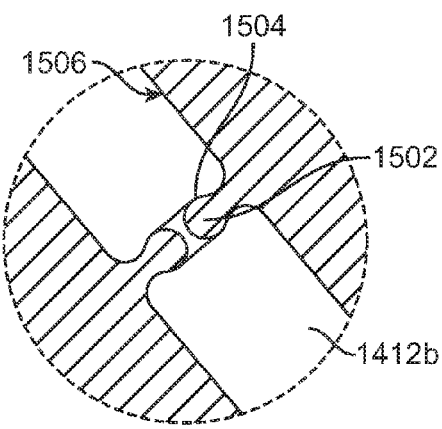
FIG. 15A    FIG. 15B
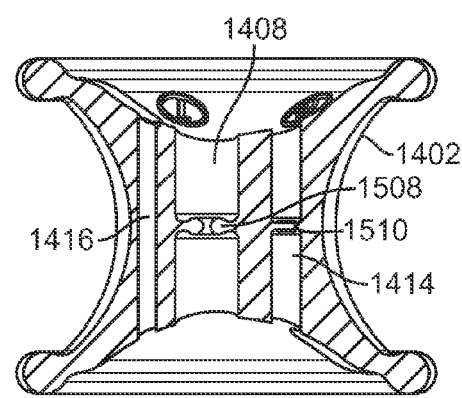
FIG. 15C

SURGICAL PORT FEATURE

CROSS REFERENCE TO RELATED APPLICATIONS

This application is a continuation in part of U.S. patent application Ser. No. 12/618,549 (filed Nov. 13, 2009) (disclosing "Curved Cannula"), which claims the benefit of provisional. U.S. Patent Application No. 61/245,171 (filed Sep. 23, 2009) (disclosing "Curved Cannula"), both of which are incorporated herein by reference.

This application may be related to the following applications: U.S. patent application Ser. No. 12/618,583 (filed Nov. 13, 2009) (disclosing "Curved Cannula Surgical System"), U.S. patent application Ser. No. 12/618,598 (filed Nov. 13, 2009) (disclosing "Curved Cannula Surgical System Control"), U.S. patent application Ser. No. 12/618,608 (filed Nov. 13, 2009) (disclosing "Curved Cannula Instrument"), and U.S. patent application Ser. No. 12/618,631 (filed Nov. 13, 2009) (disclosing "Cannula Mounting Fixture"), all of which are incorporated herein by reference.

BACKGROUND

1. Field of Invention

Inventive aspects pertain to minimally invasive surgery, more particularly to minimally invasive robotic surgical systems, and still more particularly to minimally invasive robotic surgical systems that work through a single entry point into the patient's body.

2. Art

Benefits of minimally invasive surgery are well known, and they include less patient trauma, less blood loss, and faster recovery times when compared to traditional, open incision surgery. In addition, the use of robotic surgical systems (e.g., teleoperated robotic systems that provide telepresence), such as the da Vinci® Surgical System manufactured by Intuitive Surgical, Inc. of Sunnyvale, Calif. is known. Such robotic surgical systems may allow a surgeon to operate with intuitive control and increased precision when compared to manual minimally invasive surgeries.

To further reduce patient trauma and to retain the benefits of robotic surgical systems, surgeons have begun to carry out a surgical procedure to investigate or treat a patient's condition through a single incision through the skin. In some instances, such "single port access" surgeries have been performed with manual instruments or with existing surgical robotic systems. What is desired, therefore, are improved equipment and methods that enable surgeons to more effectively perform single port access surgeries, as compared with the use of existing equipment and methods. It is also desired to be able to easily modify existing robotic surgical systems that are typically used for multiple incision (multi-port) surgeries to perform such single port access surgeries.

SUMMARY

In one aspect, a surgical system includes a robotic manipulator, a curved cannula, and an instrument with a passively flexible shaft that extends through the curved cannula. The robotic manipulator moves the curved cannula around a remote center of motion that is placed at an opening into a patient's body (e.g., an incision, a natural orifice) so that the curved cannula provides a triangulation angle for the surgical instrument at the surgical site. In one implementation, an endoscope and two such curved cannulas with distal ends oriented towards a surgical site from different angles are used so that effective instrument triangulation is achieved, which allows the surgeon to effectively work at and view the surgical site.

In another aspect, the curved cannula includes a straight section and an adjacent curved section. A robotic manipulator mounting bracket is coupled to the straight section. A second straight section may be coupled to the opposite end of the curved section to facilitate alignment of a passively flexible surgical instrument that extends out of the cannula's distal end towards a surgical site.

In another aspect, a surgical instrument includes a passively flexible shaft and a surgical end effector coupled to the distal end of the shaft. The flexible shaft extends through a curved cannula, and a distal section of the flexible shaft extends cantilevered beyond a distal end of the curved cannula. The distal section of the flexible shaft is sufficiently stiff to provide effective surgical action at the surgical site, yet it is sufficiently flexible to allow it to be inserted and withdrawn through the curved cannula. In some aspects, the stiffness of the distal section of the instrument shaft is larger than the stiffness of the section of the shaft that remains in the curved section of the cannula during a surgical procedure.

In another aspect, a surgical port feature is a single body that includes channels between its top and bottom surfaces. The channels are angled in opposite directions to hold the straight sections of the curved cannulas at a desired angle. The body is sufficiently flexible to allow the curved cannulas to move around remote centers of motion that are generally located within the channels. In some aspects the port feature also includes a channel for an endoscope cannula and/or one or more auxiliary channels. The channels may include various seals.

In another aspect, a second port feature that includes an upper funnel portion and a lower tongue is disclosed. Channels for surgical instruments, such as the curved cannulas, are defined in a waist section that joins the funnel portion and the tongue. In one aspect, this second port feature is used for surgeries that require instruments to enter the patient's body at a relatively small (acute) angle, because the port feature helps prevent unnecessary stress between the instruments and the patient's body and vice versa.

In another aspect, cannula mounting fixtures are disclosed. These fixtures support the cannulas for insertion and for docking to their associated robotic manipulators. In one aspect, a fixture includes arms that hold an endoscope cannula and a curved instrument cannula. In another aspect, a fixture is configured as a cap that holds distal ends of an endoscope and a curved cannula. The cap is pointed to facilitate insertion into the opening into the patient.

In another aspect, a control system for a robotic surgical system with a curved cannula is disclosed. The control system uses kinematic data associated with the curved cannula. To provide an intuitive control experience for the surgeon, the control system commands a robotic manipulator to move the curved cannula and its instrument in response to the surgeon's inputs at a master manipulator as if the instrument were positioned along a straight axis that extends from the distal end of the curved cannula, generally tangent to the distal end of the cannula's curved section.

BRIEF DESCRIPTION OF THE DRAWINGS

FIG. 9C is a diagrammatic view of a pull/pull type end effector.

FIG. 9D is an exploded perspective view of the distal end of another flexible shaft instrument.

FIG. 9E is a diagrammatic view of a push/pull type end effector.

FIG. 14A is a diagrammatic plan view of a port feature.

FIG. 14B is a diagrammatic perspective view of a port feature.

FIG. 15A is a diagrammatic cross-sectional view taken at a cut line in FIG. 14A.

FIG. 15B shows a detail of a seal depicted in FIG. 15A.

FIG. 15C is a diagrammatic cross-sectional view taken at another cut line in FIG. 14A.

DETAILED DESCRIPTION

Figure 1A:
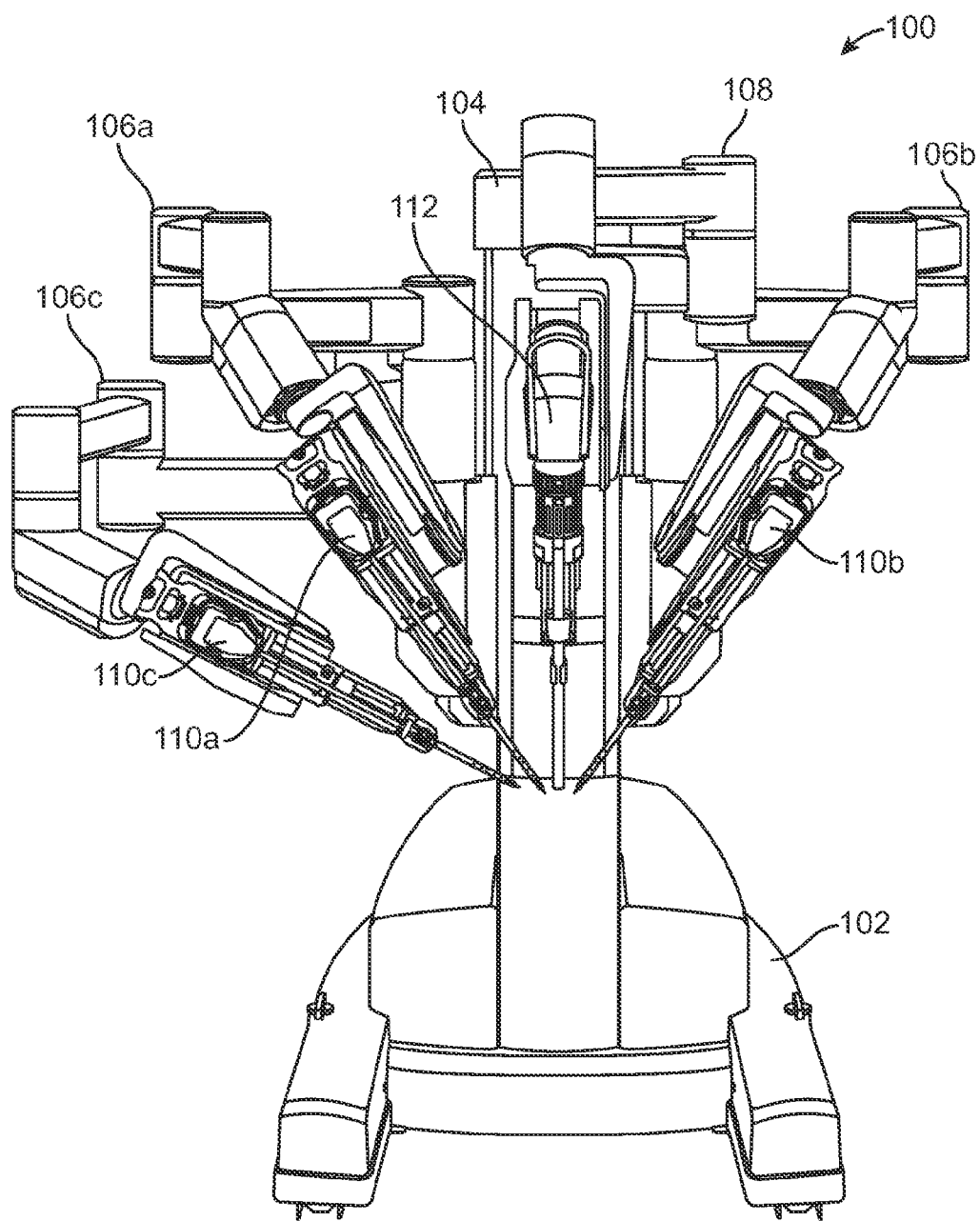
FIG. 1A is a front elevation view of a patient side cart in a robotic surgical system.

This description and the accompanying drawings that illustrate inventive aspects and embodiments should not be taken as limiting—the claims define the protected invention. Various mechanical, compositional, structural, electrical, and operational changes may be made without departing from the spirit and scope of this description and the claims. In some instances, well-known circuits, structures, and techniques have not been shown or described in detail in order not to obscure the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

The term "flexible" in association with a mechanical structure or component should be broadly construed. In essence, the term means the structure or component can be repeatedly bent and restored to an original shape without harm. Many "rigid" objects have a slight inherent resilient "bendiness" due to material properties, although such objects are not considered "flexible" as the term is used herein. A flexible mechanical structure may have infinite degrees of freedom (DOF's). Examples of such structures include closed, bendable tubes (made from, e.g., NITINOL, polymer, soft rubber, and the like), helical coil springs, etc. that can be bent into various simple and compound curves, often without significant cross-sectional deformation. Other flexible mechanical structures may approximate such an infinite-DOF piece by using a series of closely spaced components that are similar to "vertebrae" in a snake-like arrangement. In such a vertebral arrangement, each component is a short link in a kinematic chain, and movable mechanical constraints (e.g., pin hinge, cup and ball, live hinge, and the like) between each link may allow one (e.g., pitch) or two (e.g., pitch and yaw) DOF's of relative movement between the links. A short, flexible structure may serve as, and be modeled as, a single mechanical constraint (joint) that provides one or more DOF's between two links in a kinematic chain, even though the flexible structure itself may be a kinematic chain made of several coupled links. Knowledgeable persons will understand that a component's flexibility may be expressed in terms of its stiffness.

In this description, a flexible mechanical structure or component may be either actively or passively flexible. An actively flexible piece may be bent by using forces inherently associated with the piece itself. For example, one or more tendons may be routed lengthwise along the piece and offset from the piece's longitudinal axis, so that tension on the one or more tendons causes the piece to bend. Other ways of actively bending an actively flexible piece include, without limitation, the use of pneumatic or hydraulic power, gears, electroactive polymer, and the like. A passively flexible piece is bent by using a force external to the piece. An example of a passively flexible piece with inherent stiffness is a plastic rod or a resilient rubber tube. An actively flexible piece, when not actuated by its inherently associated forces, may be passively flexible. A single component may be made of one or more actively and passively flexible portions in series.

Aspects of the invention are described primarily in terms of an implementation using a da Vinci® Surgical System (specifically, a Model IS3000, marketed as the da Vinci® Si™ HD™ Surgical System), manufactured by Intuitive Surgical, Inc. of Sunnyvale, Calif. Knowledgeable persons will understand, however, that inventive aspects disclosed herein may be embodied and implemented in various ways, including robotic and non-robotic embodiments and implementations. Implementations on da Vinci® Surgical Systems (e.g., the Model IS3000; the Model IS2000, marketed as the da Vinci® S™ HD™ Surgical System) are merely exemplary and are not to be considered as limiting the scope of the inventive aspects disclosed herein.

Figure 1B:
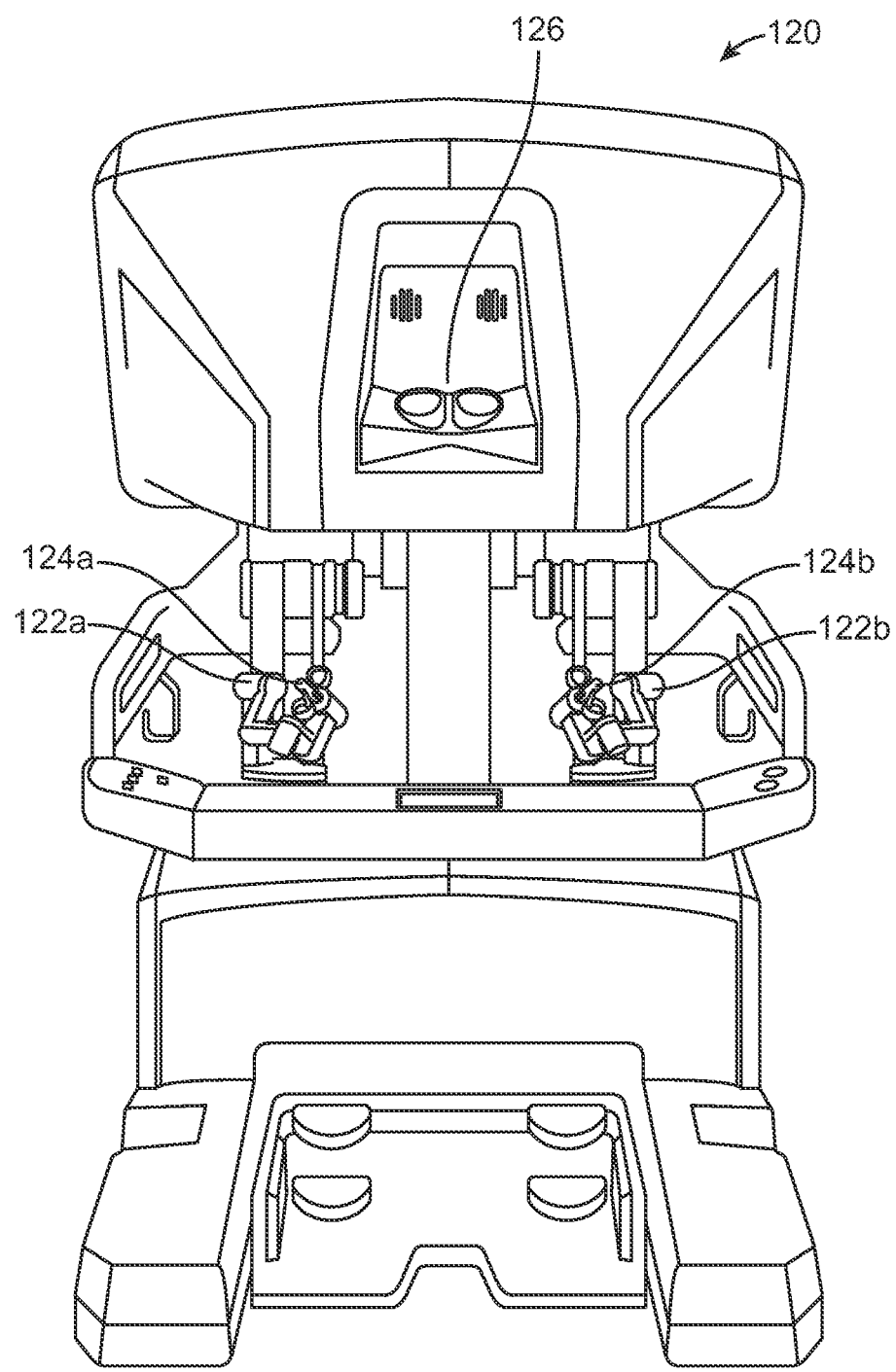
FIG. 1B is a front elevation view of a surgeon's console in a robotic surgical system.
Figure 1C:
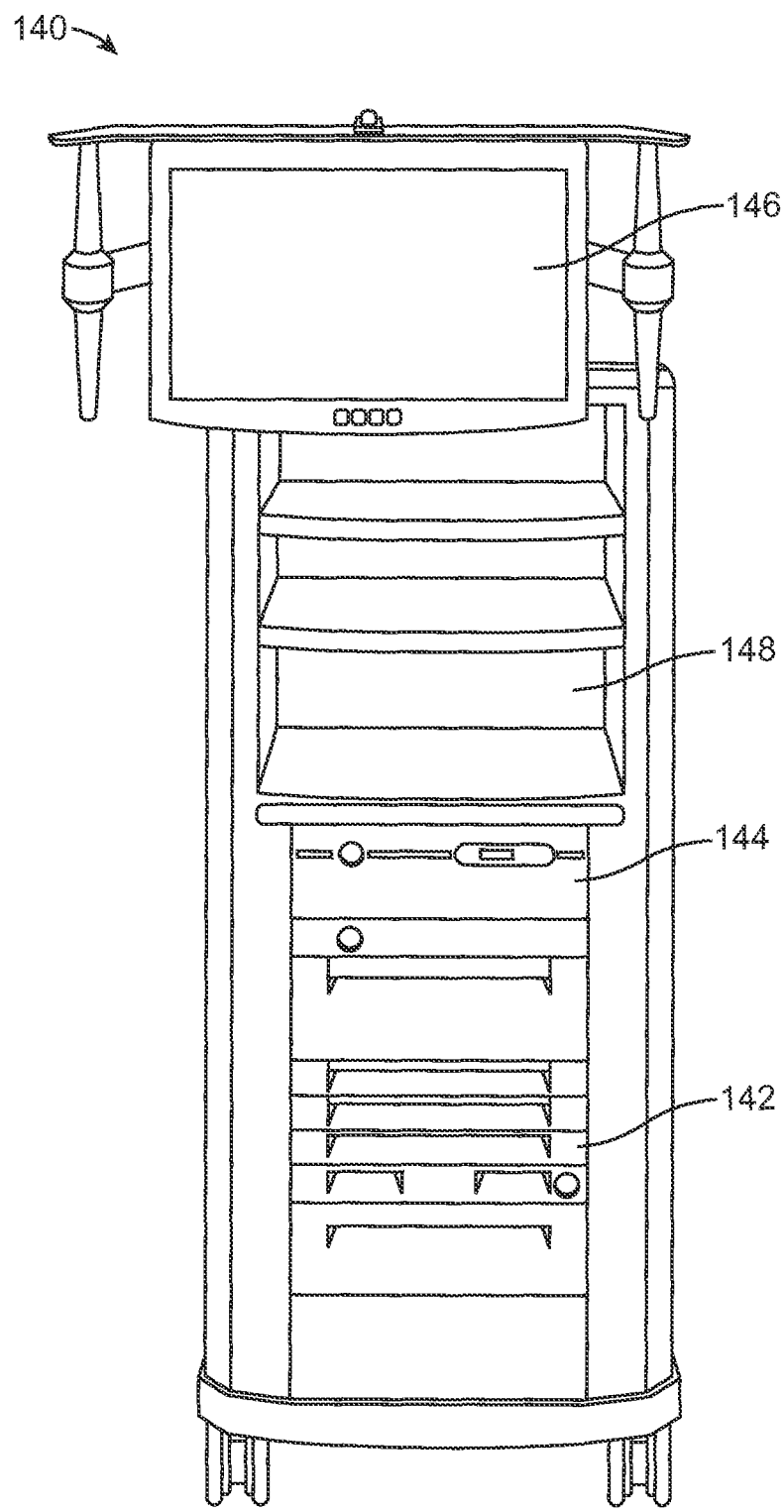
FIG. 1C is a front elevation view of a vision cart in a robotic surgical system.

FIGS. 1A, 1B, and 1C are front elevation views of three main components of a teleoperated robotic surgical system for minimally invasive surgery. These three components are interconnected so as to allow a surgeon, with the assistance of a surgical team, perform diagnostic and corrective surgical procedures on a patient.

FIG. 1A is a front elevation view of the patient side cart component 100 of the da Vinci® Surgical System. The patient side cart includes a base 102 that rests on the floor, a support tower 104 that is mounted on the base 102, and several arms that support surgical tools (which include a stereoscopic endoscope). As shown in FIG. 1A, arms 106a,106b are instrument arms that support and move the surgical instruments used to manipulate tissue, and arm 108 is a camera arm that supports and moves the endoscope. FIG. 1A also shows an optional third instrument arm 106c that is supported on the back side of support tower 104 and that can be positioned to either the left or right side of the patient side cart as necessary to conduct a surgical procedure. FIG. 1A further shows interchangeable surgical instruments 110a,110b,110c mounted on the instrument arms 106a,106b,106c, and it shows endoscope 112 mounted on the camera arm 108. The arms are discussed in more detail below. Knowledgeable persons will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm).

FIG. 1B is a front elevation view of a surgeon's console 120 component of the da Vinci® Surgical System. The surgeon's console is equipped with left and right multiple DOF master tool manipulators (MTM's) 122a,122b, which are kinematic chains that are used to control the surgical tools (which include the endoscope and various cannulas). The surgeon grasps a pincher assembly 124a,124b on each MTM 122, typically with the thumb and forefinger, and can move the pincher assembly to various positions and orientations. When a tool control mode is selected, each MTM 122 is coupled to control a corresponding instrument arm 106 for the patient side cart 100. For example, left MTM 122a may be coupled to control instrument arm 106b and instrument 110a, and right MTM 122b may be coupled to control instrument arm 106b and instrument 110b. If the third instrument arm 106c is used during a surgical procedure and is positioned on the left side, then left MTM 122a can be switched between controlling arm 106a and instrument 110a to controlling arm 106c and instrument 110c. Likewise, if the third instrument arm 106c is used during a surgical procedure and is positioned on the right side, then right MTM 122a can be switched between controlling arm 106b and instrument 110b to controlling arm 106c and instrument 110c. In some instances, control assignments between MTM's 122a,122b and arm 106a/instrument 110a combination and arm 106b/instrument 110b combination may also be exchanged. This may be done, for example, if the endoscope is rolled 180 degrees, so that the instrument moving in the endoscope's field of view appears to be on the same side as the MTM the surgeon is moving. The pincher assembly is typically used to operate a jawed surgical end effector (e.g., scissors, grasping retractor, needle driver, and the like) at the distal end of an instrument 110.

Surgeon's console 120 also includes a stereoscopic image display system 126. Left side and right side images captured by the stereoscopic endoscope 112 are output on corresponding left and right displays, which the surgeon perceives as a three-dimensional image on display system 126. In an advantageous configuration, the MTM's 122 are positioned below display system 126 so that the images of the surgical tools shown in the display appear to be co-located with the surgeon's hands below the display. This feature allows the surgeon to intuitively control the various surgical tools in the three-dimensional display as if watching the hands directly. Accordingly, the MTM servo control of the associated instrument arm and instrument is based on the endoscopic image reference frame.

The endoscopic image reference frame is also used if the MTM's are switched to a camera control mode. In the da Vinci® Surgical System, if the camera control mode is selected, the surgeon may move the distal end of the endoscope by moving one or both of the MTM's together (portions of the two MTM's may be servomechanically coupled so that the two MTM portions appear to move together as a unit). The surgeon may then intuitively move (e.g., pan, tilt, zoom) the displayed stereoscopic image by moving the MTM's as if holding the image in the hands.

The surgeon's console 120 is typically located in the same operating room as the patient side cart 100, although it is positioned so that the surgeon operating the console is outside the sterile field. One or more assistants typically assist the surgeon by working within the sterile surgical field (e.g., to change tools on the patient side cart, to perform manual retraction, etc.). Accordingly, the surgeon operates remote from the sterile field, and so the console may be located in a separate room or building from the operating room. In some implementations, two consoles 120 (either co-located or remote from one another) may be networked together so that two surgeons can simultaneously view and control tools at the surgical site.

FIG. 1C is a front elevation view of a vision cart component 140 of the da Vinci® Surgical System. The vision cart 140 houses the surgical system's central electronic data processing unit 142 and vision equipment 144. The central electronic data processing unit includes much of the data processing used to operate the surgical system. In various other implementations, however, the electronic data processing may be distributed in the surgeon console and patient side cart. The vision equipment includes camera control units for the left and right image capture functions of the stereoscopic endoscope 112. The vision equipment also includes illumination equipment (e.g., Xenon lamp) that provides illumination for imaging the surgical site. As shown in FIG. 1C, the vision cart includes an optional 24-inch touch screen monitor 146, which may be mounted elsewhere, such as on the patient side cart 100. The vision cart 140 further includes space 148 for optional auxiliary surgical equipment, such as electrosurgical units and insufflators. The patient side cart and the surgeon's console are coupled via optical fiber communications links to the vision cart so that the three components together act as a single teleoperated minimally invasive surgical system that provides an intuitive telepresence for the surgeon. And, as mentioned above, a second surgeon's console may be included so that a second surgeon can, e.g., proctor the first surgeon's work.

Figure 2A:
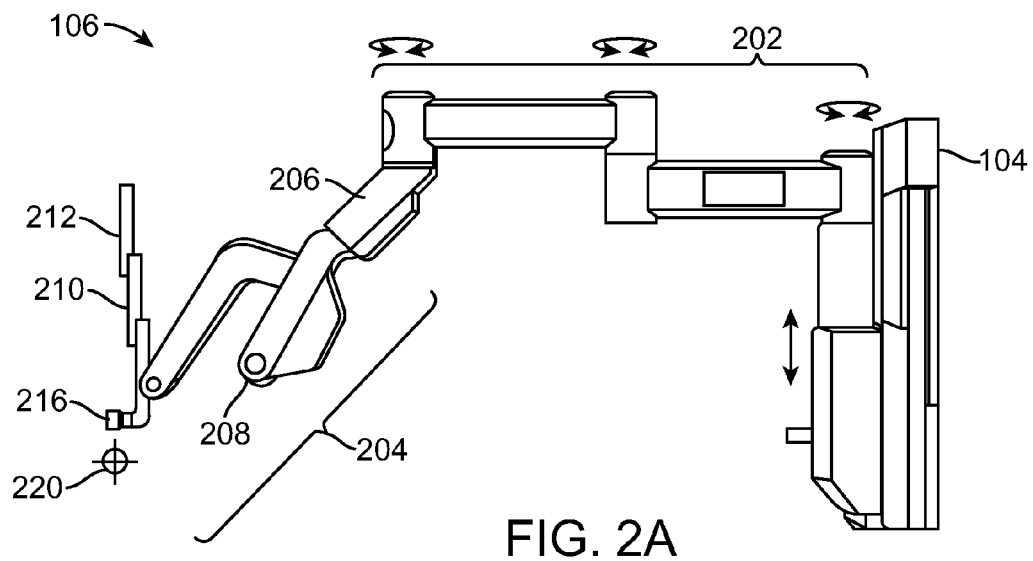
FIG. 2A is a side elevation view of an instrument arm.

FIG. 2A is a side elevation view of an illustrative instrument arm 106. Sterile drapes and associated mechanisms that are normally used during surgery are omitted for clarity. The arm is made of a series of links and joints that couple the links together. The arm is divided into two portions. The first portion is the "set-up" portion 202, in which unpowered joints couple the links. The second portion is powered, robotic manipulator portion 204 (patient side manipulator; "PSM") that supports and moves the surgical instrument. During use, the set-up portion 202 is moved to place the manipulator portion 204 in the proper position to carry out the desired surgical task. The set-up portion joints are then locked (e.g., with brake mechanisms) to prevent this portion of the arm from moving.

Figure 2B:
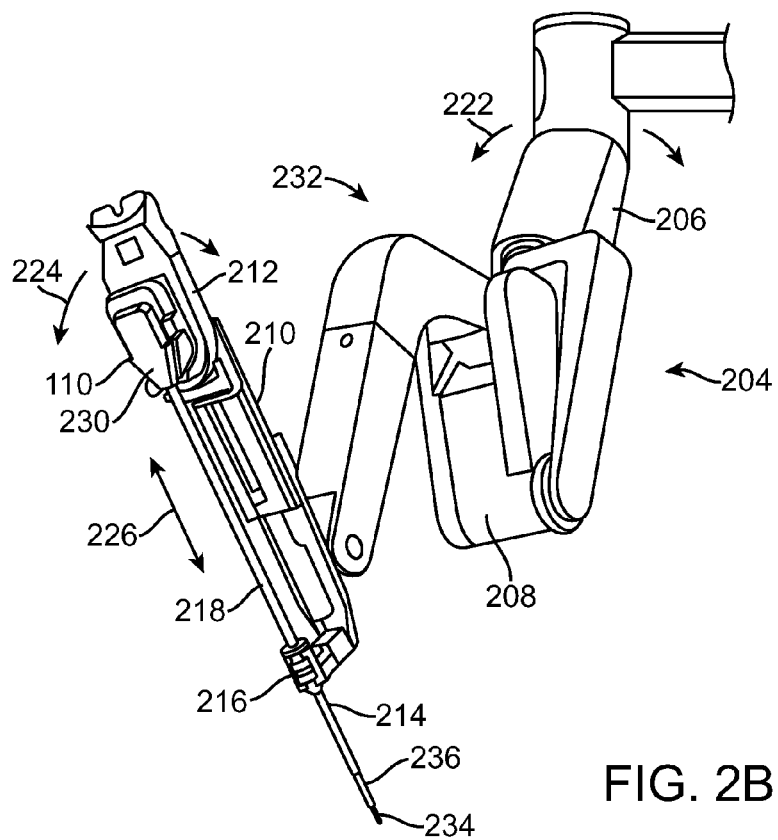
FIG. 2B is a perspective view of a manipulator with an instrument mounted.

FIG. 2B is a perspective view of the PSM 204 with an illustrative instrument 110 mounted. The PSM 204 includes a yaw servo actuator 206, a pitch servo actuator 208, and an insertion and withdrawal ("I/O") actuator 210. An illustrative surgical instrument 110 is shown mounted at an instrument mounting carriage 212. An illustrative straight cannula 214 is shown mounted to cannula mount 216. Shaft 218 of instrument 110 extends through cannula 214. PSM 204 is mechanically constrained so that it moves instrument 110 around a stationary remote center of motion 220 located along the instrument shaft. Yaw actuator 206 provides yaw motion 222 around remote center 220, pitch actuator 208 provides pitch motion 224 around remote center 220, and I/O actuator 210 provides insertion and withdrawal motion 226 through remote center 220. The set up portion 202 is typically positioned to place remote center of motion 220 at the incision in the patient's body wall during surgery and to allow for sufficient yaw and pitch motion to be available to carry out the intended surgical task. Knowledgeable persons will understand that motion around a remote center of motion may also be constrained solely by the use of software, rather than by a physical constraint defined by a mechanical assembly.

Matching force transmission disks in mounting carriage 212 and instrument force transmission assembly 230 couple actuation forces from actuators 232 in PSM 204 to move various parts of instrument 110 in order to position, orient, and operate instrument end effector 234. Such actuation forces may typically roll instrument shaft 218 (thus providing another DOF through the remote center), operate a wrist 236 that provides yaw and pitch DOF's, and operate a movable piece or grasping jaws of various end effectors (e.g., scissors (cautery or non-cautery capable), dissectors, graspers, needle drivers, electrocautery hooks, retractors, clip appliers, etc.).

Figure 2C:
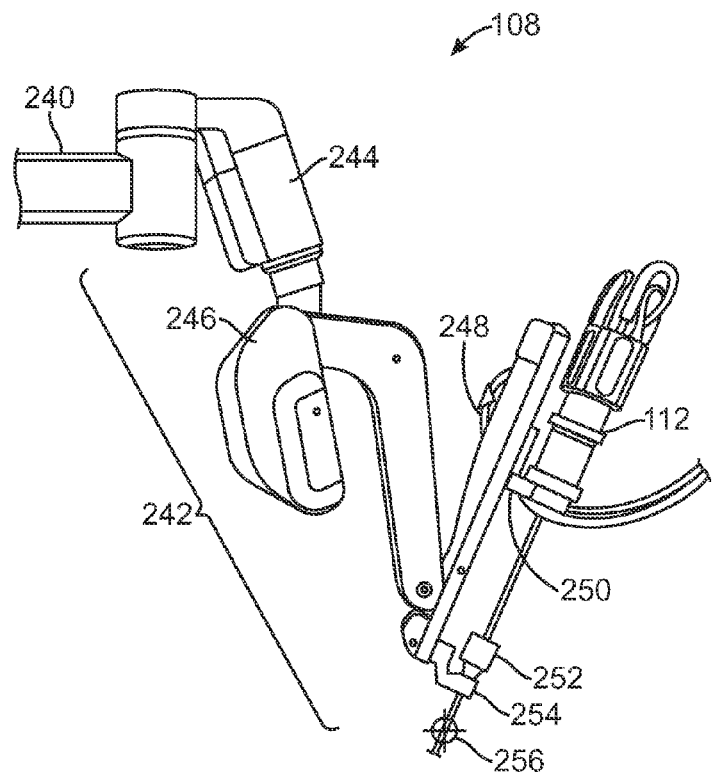
FIG. 2C is a side elevation view of a portion of a camera arm with a camera mounted.

FIG. 2C is a side elevation view of a portion of a camera arm 108 with an illustrative camera 112 mounted. Similar to the instrument arm 106, the camera arm 108 includes a set-up portion 240 and a manipulator portion 242 (endoscopic camera manipulator; "ECM"). ECM 242 is configured similarly to PSM 204 and includes a yaw motion actuator 244, a pitch motion actuator 246, and an I/O motion actuator 248. Endoscope 112 is mounted on carriage assembly 250, and endoscope cannula 252 is mounted on camera cannula mount 254. ECM 242 moves endoscope 112 around and through remote center of motion 256.

During a typical surgical procedure with the robotic surgical system described with reference to FIGS. 1A-2C, at least two incisions are made into the patient's body (usually with the use of a trocar to place the associated cannula). One incision is for the endoscope camera instrument, and the other incisions are for the necessary surgical instruments. Such incisions are sometimes referred to as "ports", a term which may also mean a piece of equipment that is used within such an incision, as described in detail below. In some surgical procedures, several instrument and/or camera ports are necessary in order to provide the needed access and imaging for a surgical site. Although the incisions are relatively small in comparison to larger incisions used for traditional open surgery, there is the need and desire to further reduce the number of incisions to further reduce patient trauma and for improved cosmesis.

Single port surgery is a technique in which all instruments used for minimally invasive surgery are passed through a single incision in the patient's body wall, or in some instances through a single natural orifice. Such methods may be referred to by various terms, such as Single Port Access (SPA), Laparo Endoscopic Single-site Surgery (LESS), Single Incision Laparoscopic Surgery (SILS), One Port Umbilical Surgery (OPUS), Single Port Incisionless Conventional Equipment-utilizing Surgery (SPICES), Single Access Site Surgical Endoscope (SASSE), or Natural Orifice TransUmbilical Surgery (NOTUS). The use of a single port may done using either manual instruments or a robotic surgical system, such as the one described above. A difficulty arises with such a technique, however, because the single port constrains the angle at which a surgical instrument can access the surgical site. Two instruments, for example, are positioned nearly side-by-side, and so it is difficult to achieve advantageous triangulation angles at the surgical site (triangulation being the ability for the distal ends of two surgical instruments to be positioned along two legs of a triangle to work effectively at a surgical site at the apex of the triangle). Further, since the instruments and endoscope enter via the same incision, straight instrument shafts tend to obscure a large part of the endoscope's field of view. And in addition, if a robotic surgical system is used, then the multiple manipulators may interfere with one another, due to both their size and their motions, which also limits the amount of end effector movement available to the surgeon.

Figure 3:
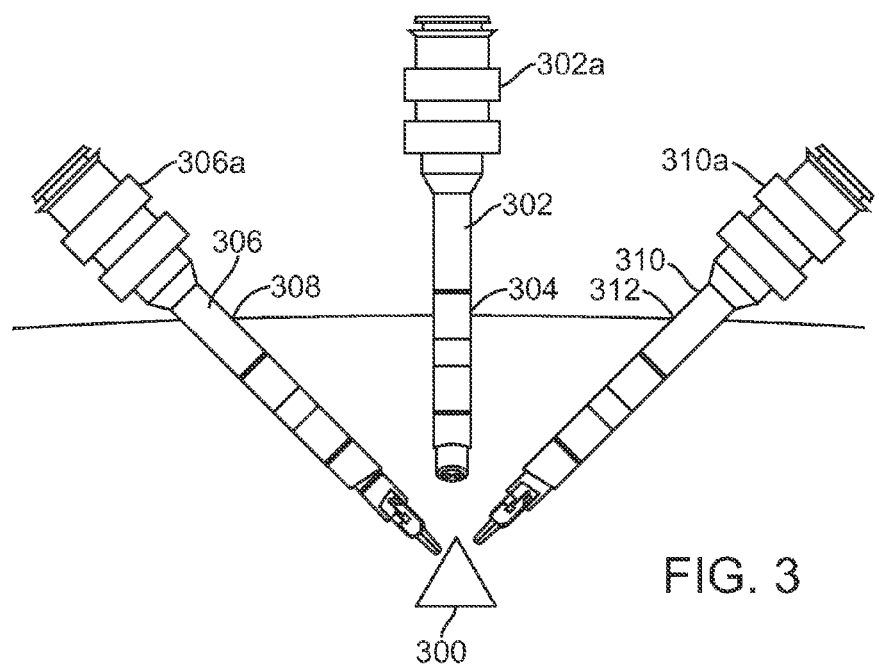
FIG. 3 is a diagrammatic view of multiple cannulas and associated instruments inserted through a body wall so as to reach a surgical site.

FIG. 3 illustrates the difficulty of using a multi-arm robotic surgical system for single port surgery. FIG. 3 is a diagrammatic view of multiple cannulas and associated instruments inserted through a body wall so as to reach a surgical site 300. As depicted in FIG. 3, a camera cannula 302 extends through a camera incision 304, a first instrument cannula 306 extends through a first instrument incision 308, and a second instrument cannula 310 extends through a second instrument incision 312. It can be seen that if each of these cannulas 302, 306,310 were to extend through the same (slightly enlarged) port 304, due to the requirement that each move around a remote center of motion and also due to the bulk and movement of the manipulators described above that hold the cannulas at mounting fittings 302a,306a,310a, then very little movement of the instrument end effectors is possible, and the cannulas and instrument shafts can obscure the surgical site in the endoscope's field of view. In order to regain some triangulation of the instruments at the surgical site, attempts have been made to cross the instrument shafts and use the instrument wrists to provide some limited triangulation, but this configuration results in a "backwards" control scheme (right side master controls left side slave instrument in the endoscope's view, and vice-versa), which is non-intuitive and so loses some of the strong benefit of intuitive telerobotic control. Straight shaft wristed manual instruments likewise require a surgeon to move instruments in either a crossed-hands or cross-visual "backwards" way. And in addition, for laparoscopic surgery, there is a difficulty of maintaining a proper pneumoperitoneum due to the multiple instruments/cannulas placed through a single incision.

For single port surgery using manual instruments, an attempt has been made to use rigid, curved instrument shafts to improve triangulation. Such curved shafts typically have a compound "S" bend that inside the body allows them to curve away from the incision and then back to the surgical site, and outside the body to curve away from the incision to provide clearance for the instrument handles and the surgeon's hands. These curved instruments appear to be even more difficult to use than straight shaft manual instruments, because the curved shafts further limit a surgeon's ability to precisely move the instruments end effector either by moving the shaft or by using a manually operated wrist mechanism. Suturing, for example, appears to be extremely difficult with such rigid curved shaft instruments. In addition, the surgeon's ability to insert and withdraw such curved shaft instruments directly between the incision and the surgical site is limited because of their shape. And, due to their shape, rolling a rigid curved instrument may cause a portion of the instrument shaft to contact, and possibly damage, tissue without the surgeon's knowledge.

For single port surgery using robotic surgical systems, methods are proposed to provide increased controllable degrees of freedom to surgical instruments. For example, the use of telerobotically controlled "snake-like" instruments and associated controllable guide tubes has been proposed as a way to access a surgical site though a single incision. Similarly, the use of instruments with a miniature mechanical parallel motion mechanism has been proposed. See e.g., U.S. Patent Application Pub. No. US 2008/0065105 A1 (filed Jun. 13, 2007) (describing a minimally invasive surgical system). While such instruments may ultimately be effective, they are often mechanically complex. And, due to their increased DOF actuation requirements, such instruments may not be compatible with existing robotic surgical systems.

Curved Cannula System

Figure 4A:
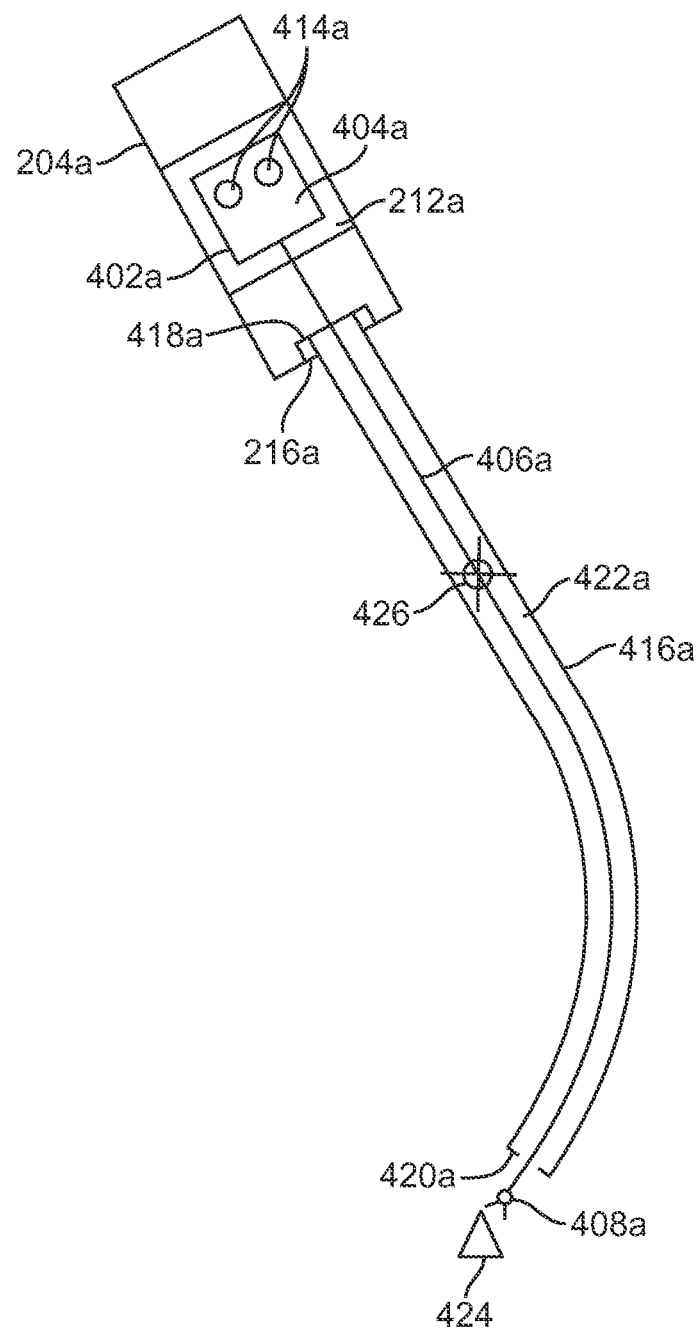
FIG. 4A is a schematic view of a portion of a patient side robotic manipulator that supports and moves a combination of a curved cannula and a passively flexible surgical instrument.

FIG. 4A is a schematic view of a portion of a patient side robotic manipulator that supports and moves a combination of a curved cannula and a passively flexible surgical instrument. As depicted in FIG. 4A, a telerobotically operated surgical instrument 402a includes a force transmission mechanism 404a, a passively flexible shaft 406a, and an end effector 408a. Instrument 402a is mounted on an instrument carriage assembly 212a of a PSM 204a (previously described components are schematically depicted for clarity). Interface discs 414a couple actuation forces from servo actuators in PSM 204a to move instrument 402a components. End effector 408a illustratively operates with a single DOF (e.g., closing jaws). A wrist to provide one or more end effector DOF's (e.g., pitch, yaw; see e.g., U.S. Pat. No. 6,817,974 (filed Jun. 28, 2002) (disclosing "Surgical Tool Having Positively Positionable Tendon-Actuated Multi-Disk Wrist Joint"), which is incorporated herein by reference) is optional and is not shown. Many instrument implementations do not include such a wrist. Omitting the wrist simplifies the number of actuation force interfaces between PSM 204a and instrument 402a, and the omission also reduces the number of force transmission elements (and hence, instrument complexity and dimensions) that would be necessary between the proximal force transmission mechanism 404a and the distally actuated piece.

FIG. 4A further shows a curved cannula 416a, which has a proximal end 418a, a distal end 420a, and a central channel 422a that extends between proximal end 418a and distal end 420a. Curved cannula 416a is, in one implementation, a rigid, single piece cannula. As depicted in FIG. 4A, proximal end 418a of curved cannula 416a is mounted on PSM 204a's cannula mount 216a. During use, instrument 402a's flexible shaft 406a extends through curved cannula 416a's central channel 422a so that a distal portion of flexible shaft 406a and end effector 408a extend beyond cannula 416a's distal end 420a in order to reach surgical site 424. As described above, PSM 204a's mechanical constraints (or, alternatively, preprogrammed software constraints in the control system for PSM 204*a*) cause instrument 402*a* and curved cannula 416*a* to move in pitch and yaw around remote center of motion 426 located along cannula 416*a*, which is typically placed at an incision in the patient's body wall. PSM 204*a*'s I/O actuation, provided by carriage 212*a*, inserts and withdraws instrument 402*a* through cannula 416*a* to move end effector 408*a* in and out. Details of instrument 402*a*, cannula 416*a*, and the control of these two components is described below.

Figure 4B:
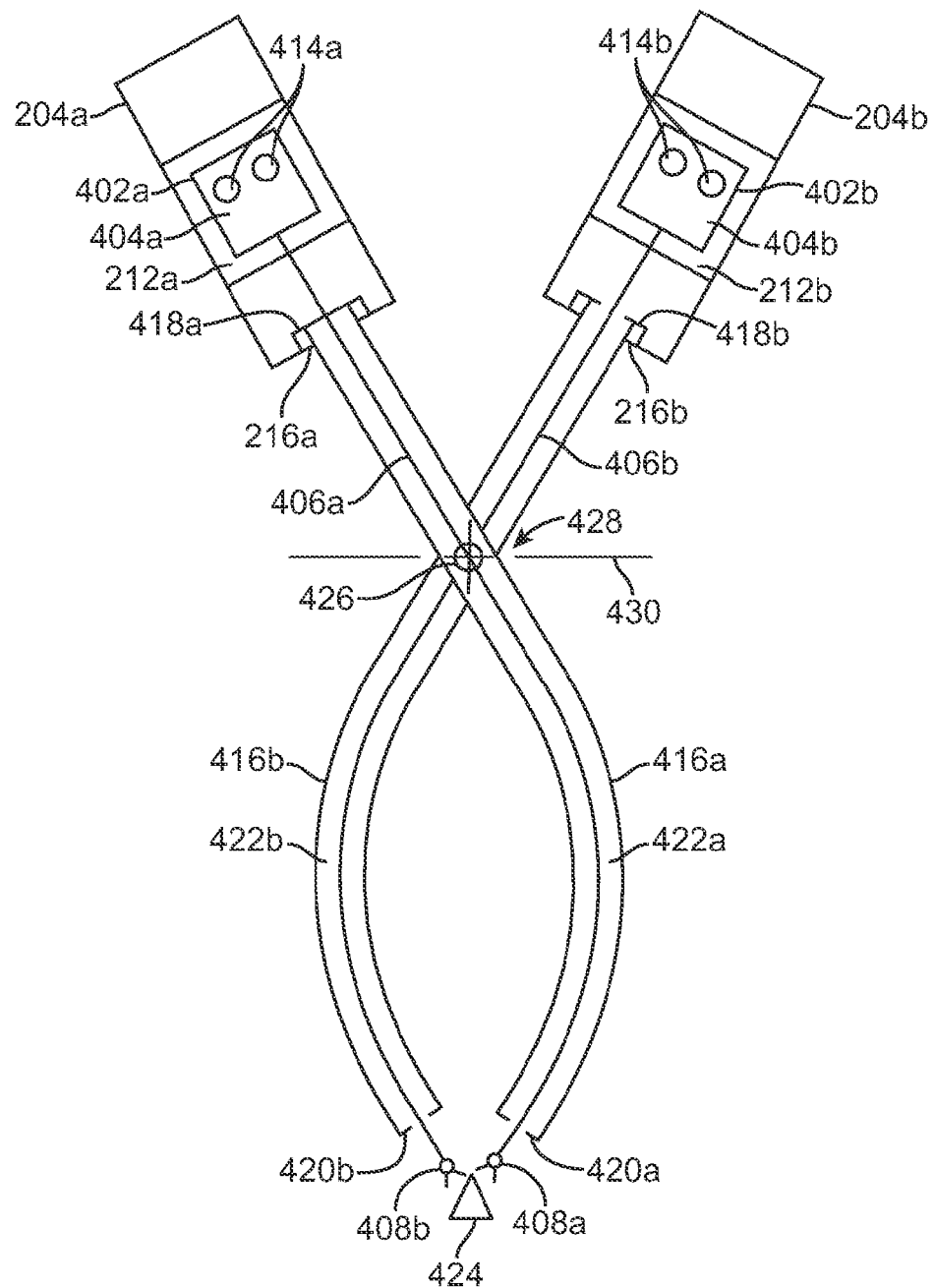
FIG. 4B is a schematic view that shows a second patient side robotic manipulator that supports and moves a second curved cannula and passively flexible surgical instrument combination, added to the FIG. 4A view.

FIG. 4B is a schematic view that shows a second patient side robotic manipulator that supports and moves a second curved cannula and passively flexible surgical instrument combination, added to the FIG. 4A view. Components of the second PSM 204*b*, instrument 402*b*, and curved cannula 416*b* are substantially similar to, and function in a substantially similar manner to, those described in FIG. 4A. Curved cannula 416*b*, however, curves in a direction opposite to the direction in which curved cannula 416*a* curves. FIG. 4B thus illustrates that two curved cannulas and associated instruments, curving in opposite directions, are positioned to extend through a single incision 428 in the patient's body wall 430 to reach surgical site 424. Each curved cannula initially angles away from a straight line between the incision and the surgical site and then curves back towards the line to direct the extended instruments to the surgical site. By operating PSM's 204*a* and 204*b* in pitch in yaw, the distal ends 420*a*,420*b* of the curved cannulas move accordingly, and therefore instrument end effectors 404*a* and 404*b* are moved with reference to the surgical site (and consequently, with reference to the endoscope's field of view). It can be seen that although the remote centers of motion for the two curved cannula and flexible instrument combinations are not identical, they are sufficiently close enough (proximate) to one another so that they can both be positioned at the single incision 428.

Figure 4C:
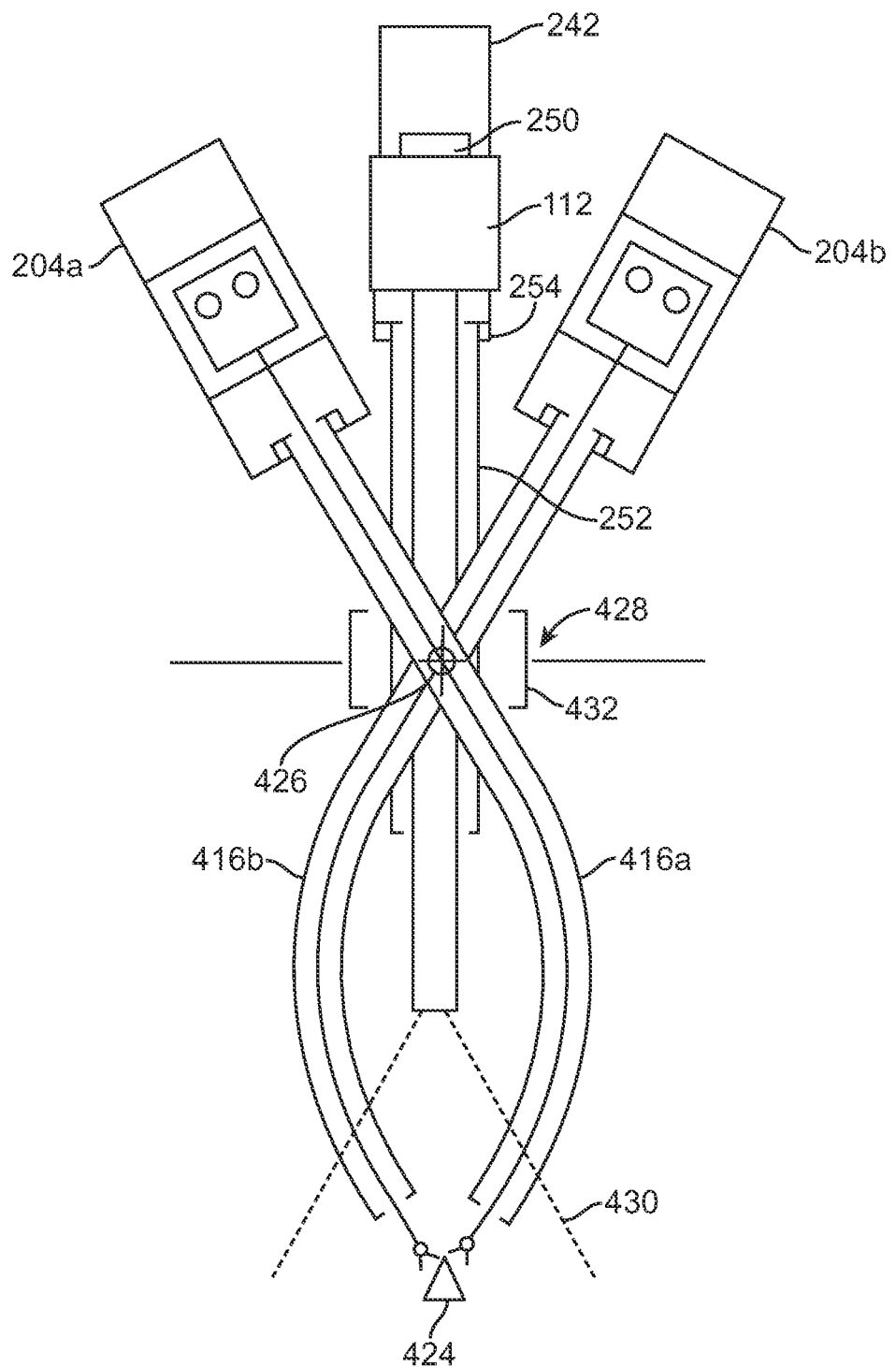
FIG. 4C is a schematic view that shows an endoscopic camera manipulator that supports an endoscope, added to the FIG. 4B view.

FIG. 4C is a schematic view that shows an endoscopic camera manipulator that supports an endoscope, added to the FIG. 4B view. Some previously used reference numbers are omitted for clarity. As shown in FIG. 4C, ECM 242 holds endoscope 112 such that it extends through single incision 428, along with the two curved cannula and flexible instrument combinations. Endoscope 112 extends through a conventional cannula 252 supported by cannula mount 254. In some implementations, cannula 252 provides insufflation to a body cavity. ECM 242 is positioned to place the endoscope 112's remote center of motion at incision 428. As above, it can be seen that the remote centers of motion for the two curved cannula and instrument combinations and the endoscope 112 are not identical, but they may be positioned sufficiently close to allow all to extend through the single incision 428 without the incision being made unduly large. In an example implementation, the three remote centers may be positioned on approximately a straight line, as illustrated in FIG. 4C. In other implementations, such as ones described below, the remote centers are not linearly aligned, yet are grouped sufficiently close.

FIG. 4C also schematically illustrates that the PSM's 204*a*, 204*b* and the ECM 242 may be positioned so that each has a significantly improved volume in which to move in pitch and yaw without interfering with each other. That is, if straight-shaft instruments are used, then the PSM's must in general remain in positions near one another to keep the shafts in a near parallel relation for effective work through a single incision. But with the curved cannulas, however, the PSM's can be placed farther from one another, and so each PSM can in general move within a relatively larger volume than with the straight-shaft instruments. In addition, FIG. 4C illustrates how the curved cannulas 416 provide an improved triangulation for the surgical instruments, so that the surgical site 426 is relatively unobstructed in endoscope 112's field of view 430.

FIG. 4C further illustrates that a port feature 432 may be placed in incision 428. Cannulas 416*a*, 416*b*, and 252 each extend through port feature 432. Such a port feature may have various configurations, as described in detail below.

Figure 5:
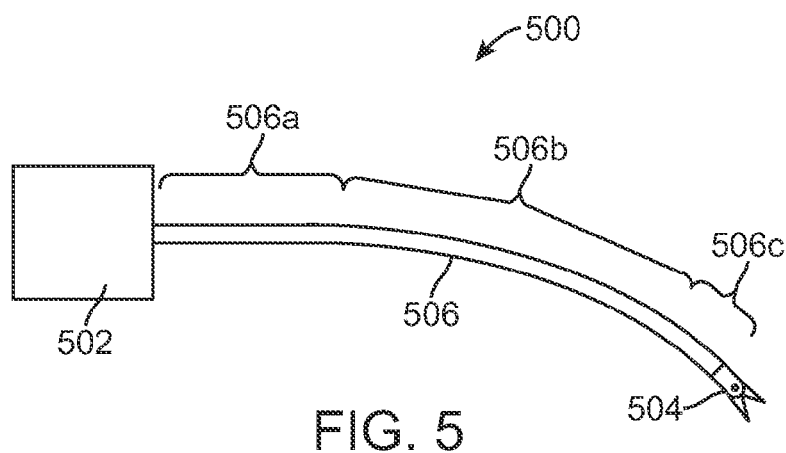
FIG. 5 is a diagrammatic view of a flexible instrument.

FIG. 5 is a diagrammatic view of an illustrative flexible instrument 500 used with a curved cannula. Instrument 500 includes a proximal end force transmission mechanism 502, a distal end surgical end effector 504, and a shaft 506 that couples force transmission mechanism 502 and end effector 504. In one implementation, shaft 506 is about 43 cm long. In some implementations, shaft 506 is passively flexible and includes three sections—a proximal section 506*a*, a distal section 506*c*, and a middle section 506*b* that is between proximal and distal sections 506*a*,506*c*.

In some implementations, the sections 506*a*,506*b*,506*c* may be each characterized by their different stiffnesses. Section 506*a* is the portion of shaft 506 that extends from force transmission mechanism 502 towards the curved cannula through which the other sections of shaft 506 extend. Consequently, section 506*a* is relatively stiff in comparison to the other sections 506*b*,506*c*. In some implementations, section 506*a* may be effectively rigid. Section 506*b* is relatively more flexible than the other two sections 506*a*,506*c*. The majority of section 506*b* is within the curved cannula during a surgical procedure, and so section 506*b* is made relatively flexible to reduce friction with the inner wall of the curved cannula, yet it is not made so flexible so that it buckles during insertion under manual or servocontrolled operation. Section 506*c* is relatively more stiff than section 506*b*, because section 506*c* extends from the distal end of the curved cannula. Accordingly, section 506*c* is made flexible enough so that it may be inserted through the bend of the curved cannula, yet it is made rigid enough to provide adequate cantilever support for end effector 504.

In some implementations, however, shaft sections 506*a*-506*c* each have the same physical structure—each being composed of the same material(s), and the material(s) chosen to have a bending stiffness acceptable for each section—so the sections thus have the same stiffness. Such instrument shafts are generally lower cost because, e.g., they have fewer parts and are easier to assemble.

For instruments that require an end effector roll DOF via shaft roll, all three sections 506*a*-506*c* are torsionally rigid enough to transmit roll motion from the proximal end of the instrument to distal surgical end effector 504. Examples are described in reference to FIGS. 8A-8D, below.

In some implementations, the stiffness of the instrument shaft (or at least the portion of the shaft that moves within the cannula), with an outer material selected to reasonably minimize shaft friction within the cannula, is close to the maximum that the robot can insert and roll. Such insertion and roll forces are substantially more than forces that can be reasonably controlled by a human, and so the stiffness of the instrument's distal section that extends from the distal end of the cannula can be made substantially higher than hand-operated instrument shaft stiffness would be for a similar but manually actuated curved cannula system. This characteristic enables the use of a curved cannula robotic surgical system in situations in which hand-operated instruments acting through curved cannulas may be marginally functional or non-functional (e.g., the hand-operated shaft stiffness is too low to enable the instrument to effectively work at the surgical site). And so, in some implementations, the instrument shaft is "tuned" (e.g., by selecting one or more particular materials and/or by various shaft constructions using the selected material(s)) to (i) make effective use of the robot's insertion and roll drive capabilities with reasonably stiff shafts while (ii) not allowing the friction between such reasonably stiff shafts and a particular cannula curve dimension to offset the robot's drive capability benefits. Thus certain instruments may have flexible shafts of one stiffness for use with cannulas with one curve radius and/or inner diameter, and other instruments may have shafts of another stiffness for use with cannulas with another curve radius and/or inner diameter. For example, for a particular shaft diameter and assuming cannula curve radius and cannula-shaft friction vary inversely, shaft stiffness for an instrument designed for use with a cannula having a relatively larger curve radius may be larger than shaft stiffness for an instrument designed for use with a cannula having a relatively smaller curve radius. In various aspects, the shaft's lateral (bending) stiffness is in a range from about 1 lb-in$^2$ (PSI×in$^4$) to about 4 lb-in$^2$, and in one implementation the shaft's lateral stiffness is about 2.0 lb-in$^2$. In various aspects, the shaft's rotational stiffness is larger than about 11 lb-in$^2$, and in one implementation the shaft's rotational stiffness is about 22.0 lb-in$^2$. For shaft implementations with a lateral stiffness in the ~1-4 lb-in$^2$ range, a practical range of rotational stiffness is in the range of about 11 lb-in$^2$ to about 66 lb-in$^2$.

Primarily due to friction, as the bend radius of a curved cannula decreases, instrument shaft stiffness must also decrease. If an isotropic material is used for the instrument shaft, such as is illustrated in association with FIGS. 8C and 8D, then the stiffness of the shaft portion that extends from the cannula's distal end is also reduced. At some point, either the stiffness of the shaft's extended distal end or the stiffness of the shaft portion between the transmission mechanism and the cannula may become unacceptably low. Therefore, as described above, a range of stiffnesses may be defined for an isotropic material shaft of fixed dimensions, depending on a cannula's bend radius and inner diameter.

Surgical instrument end effectors placed at the distal end of the flexible shaft instruments are of two general types. The first type of end effector has no moving parts. Such non-moving end effectors may include, for example, suction/irrigation tips, electrocautery hooks or blades, probes, blunt dissectors, cameras, retractors, etc. The second type of end effector has at least one moving component that is actuated under robotic control. Such moving component end effectors include, for example, graspers, needle drivers, moving cautery hooks, clip appliers, shears (both non-cautery and cautery), etc.

The one or more moving end effector components may be actuated in various ways. In one aspect, two tension elements may be used to actuate an end effector component. In such a "pull/pull" design, one tension element moves the end effector component in one direction, and the second tension element moves the component in the opposite direction. In another aspect, a single compression/tension element is used to move the end effector component. In such a "push/pull" design, pulling (tension) is used to move the component in one direction, and pushing (compression) is used to move the component in the opposite direction. In some implementations, the tension force is used to actuate the end effector component in the direction that requires the highest force (e.g., closing jaws).

Figure 6A:
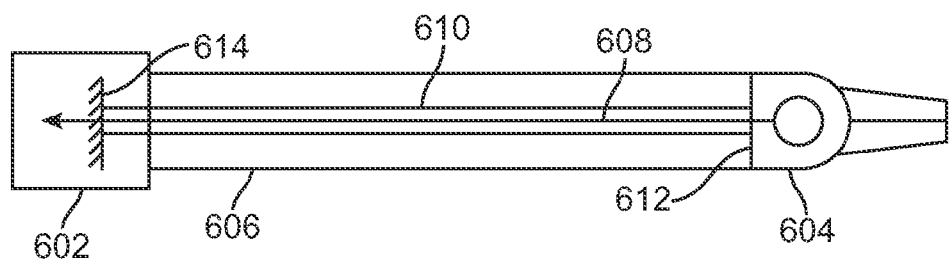
FIG. 6A is a diagrammatic view of a pull/pull instrument design.

FIG. 6A is a diagrammatic view that illustrates aspects of a pull/pull instrument design. As shown in FIG. 6A, an instrument force transmission mechanism 602 is coupled to a grip-type end effector 604 by a flexible shaft body 606. A tension element 608 is routed through shaft body 606 and couples a movable component in end effector 604 to a component (not shown; see below) in transmission mechanism 602 that receives a robotic actuation force. Tension element 608 is routed through a force isolation component 610 that is coupled between the base 612 of the end effector and backing plate 614 in transmission mechanism 602. In one implementation, shaft body 606 is a plastic tube (e.g., polyaryletheretherketone (PEEK)), tension element 608 is a hypotube (e.g., 316 Stainless Steel (face hardened), 0.028-inch OD×0.020 ID, with polytetrafluoroethylene (PTFE) dip coating) with cables (e.g., 0.018-inch tungsten) at each end that are coupled to the transmission mechanism and end effector components, and force isolation component 610 is a coil tube (e.g., 300 series stainless steel). In one implementation 304V (vacuum arc remelt) stainless steel is used, because its surface finish is relatively smoother than other 300 series stainless steels, which results in a lower friction for the interior of the coil tube. It can be seen that shaft body 606 does not experience the tension load on tension element 608 that moves the end effector component, because the tension force is offset by an equal and opposite reaction force in isolation component 610. Consequently, two such tension element and force isolation component pairs within shaft body tube 606 can be used for a pull/pull end effector actuation design, the instrument shaft remains flexible with no effective change in its designed stiffness or bend during pull/pull actuation, and the tension load on tension element 608 is effectively independent of shaft body 606 bending.

Figure 6B:
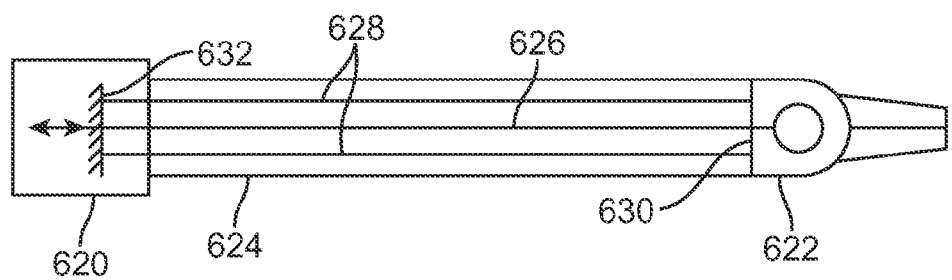
FIG. 6B is a diagrammatic view of a push/pull instrument design.

FIG. 6B is a diagrammatic view that illustrates aspects of a push/pull instrument design. As shown in FIG. 6B, an instrument force transmission mechanism 620 is coupled to a grip-type end effector 622 by a flexible shaft body 624. A compression/tension drive element 626 is routed through shaft body 624 and couples a movable component in end effector 622 to a component (not shown; see below) in transmission mechanism 620 that receives a robotic actuation force. One or more force isolation components 628 (an illustrative two are shown) are also routed through shaft body 624 and are coupled to the base 630 of the end effector and to a backing plate 632 in the force transmission mechanism. In one implementation, shaft body 624 is a plastic tube (e.g., PEEK), drive element 626 is a solid rod (e.g., 304V Stainless Steel, 0.032-inch OD with PTFE spray coating), and force isolation components 628 are also solid rods (e.g., 304V Stainless Steel, 0.032-inch OD with PTFE spray coating). It can be seen that shaft body 624 does not experience either the compression or tension loads on drive element 626 that moves the end effector component, because the drive forces are offset by equal and opposite reaction forces in isolation components 628. Consequently, the instrument shaft remains flexible with no effective change in its designed stiffness or bend during push/pull actuation, and the drive loads on drive element 626 are effectively independent of shaft body 624 bending. In addition to stiffening the instrument shaft along its longitudinal axis to isolate the push/pull drive loads, the force isolation components 628 can act to effectively increase the instrument shaft's bending stiffness a desired value.

Figure 7A:
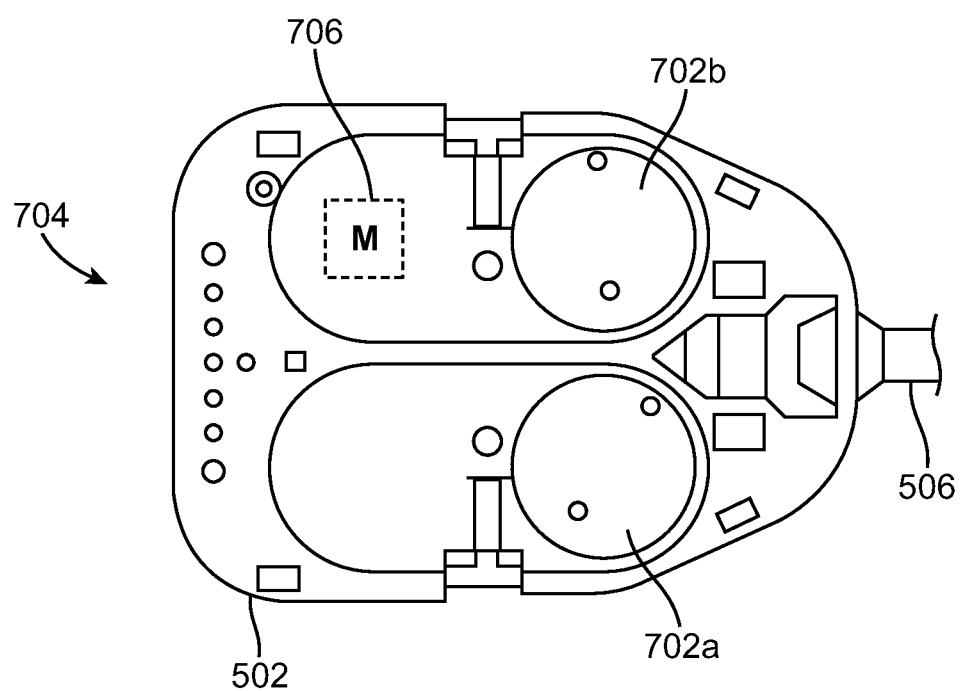
FIG. 7A is a bottom view of a force transmission mechanism.

FIG. 7A is a bottom view of an implementation of force transmission mechanism 502. As shown in FIG. 7A, the force transmission mechanism of a surgical instrument used in a da Vinci® Surgical System has been modified to eliminate the mechanisms used to control a wrist mechanism on the instrument and to control the jaw of an end effector (or other moveable part) using only a single interface disk. Thus in one illustrative implementation, one interface disk 702a rolls shaft 506 so as to provide a roll DOF for end effector 504, and a second interface disk 702b operates end effector 504's jaw mechanism. As described above, in one implementation a bulkhead in transmission mechanism 502 supports coil tubes that run through the instrument shaft, as described in detail above and below. Force transmission mechanism 502 may be coupled to PSM 204 without any mechanical modifications required to the PSM, a feature that minimizes implementation costs of curved cannula aspects in existing robotic surgical systems.

FIG. 7A also shows that implementations of force transmission mechanism 502 may include electrically conductive interface pins 704 and an electronic data memory 706 that is electrically coupled to interface pins 704. Parameters relevant to instrument 500 and its operation (e.g., number of times the instrument has been used, Denavit-Hartenberg parameters for control (described below), etc.) may be stored in memory 706 and accessed by the robotic surgical system during operation to properly use the instrument (see e.g., U.S. Pat. No. 6,331,181 (filed Oct. 15, 1999) (disclosing surgical robotic tools, data architecture, and use), which is incorporated herein by reference). In one implementation, kinematic data specific to the curved cannula through which the instrument extends may also be stored in memory 706, so that if the system detects that a curved cannula is mounted (see e.g., FIG. 10 and associated text below), the system may access and use the stored cannula data. If more than one curved cannula kinematic configuration (e.g., different lengths, bend radii, bend angles, etc.) is used, then data specific to each allowable configuration may be stored in the associated instrument's memory, and the system may access and use data for the specific cannula configuration that is mounted. In addition, in some instances if the robotic surgical system senses that a flexible instrument has been coupled to a manipulator that holds a straight, rather than curved, cannula, then the system may declare this situation to be an illegal state and prevent operation.

Figure 7B:
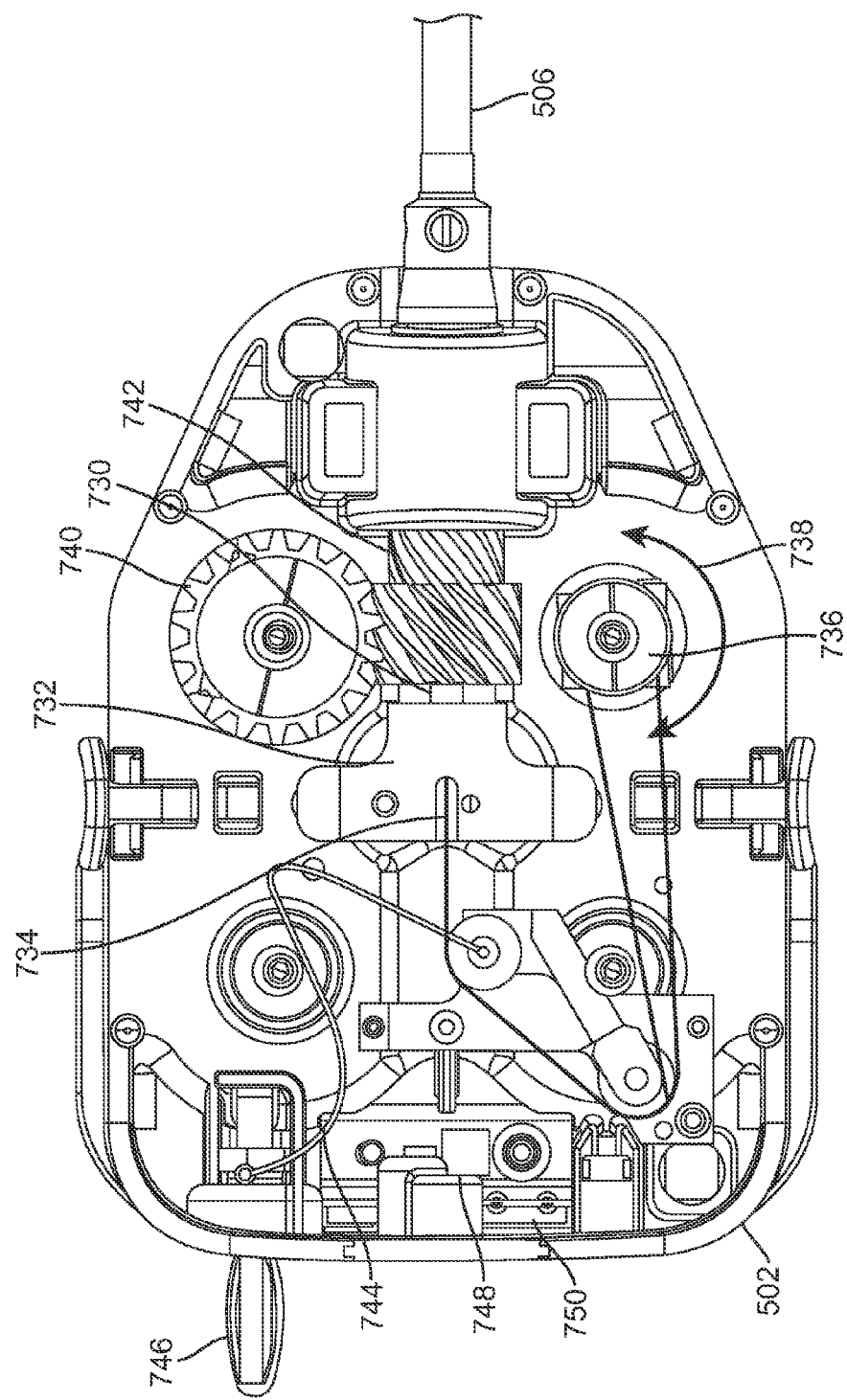
FIG. 7B is a plan view of a force transmission mechanism used in a pull/pull instrument design.

FIG. 7B is a plan view of an illustrative implementation of a force transmission mechanism used in a pull/pull instrument design. As shown in FIG. 7B, two coil tubes 730 are positioned against backing plate 732. Two tension elements 734 extend from the coil tubes, through the backing plate, and are routed to open/close capstan 736, which rotates as indicated by arrows 738 to pull on one or the other of the tension elements. FIG. 7B also depicts an illustrative implementation of shaft roll—cross-connected helical drive gear 740 and shaft roll gear 742. Roll gear 742 is coupled (e.g., laser welded) to a stainless steel adaptor swaged over the proximal end of the flexible shaft's body tube. FIG. 7B further depicts an illustrative monopolar electrocautery energy connection 744 between plug 746 and electrically conductive tension elements 734. And, FIG. 7B depicts an illustrative positioning of a memory chip 748 that contains instrument and/or associated cannula data, as described herein, and the chip's associated electrical contacts 750 that connect with the surgical system through mating contacts on the PSM.

Figure 7C:
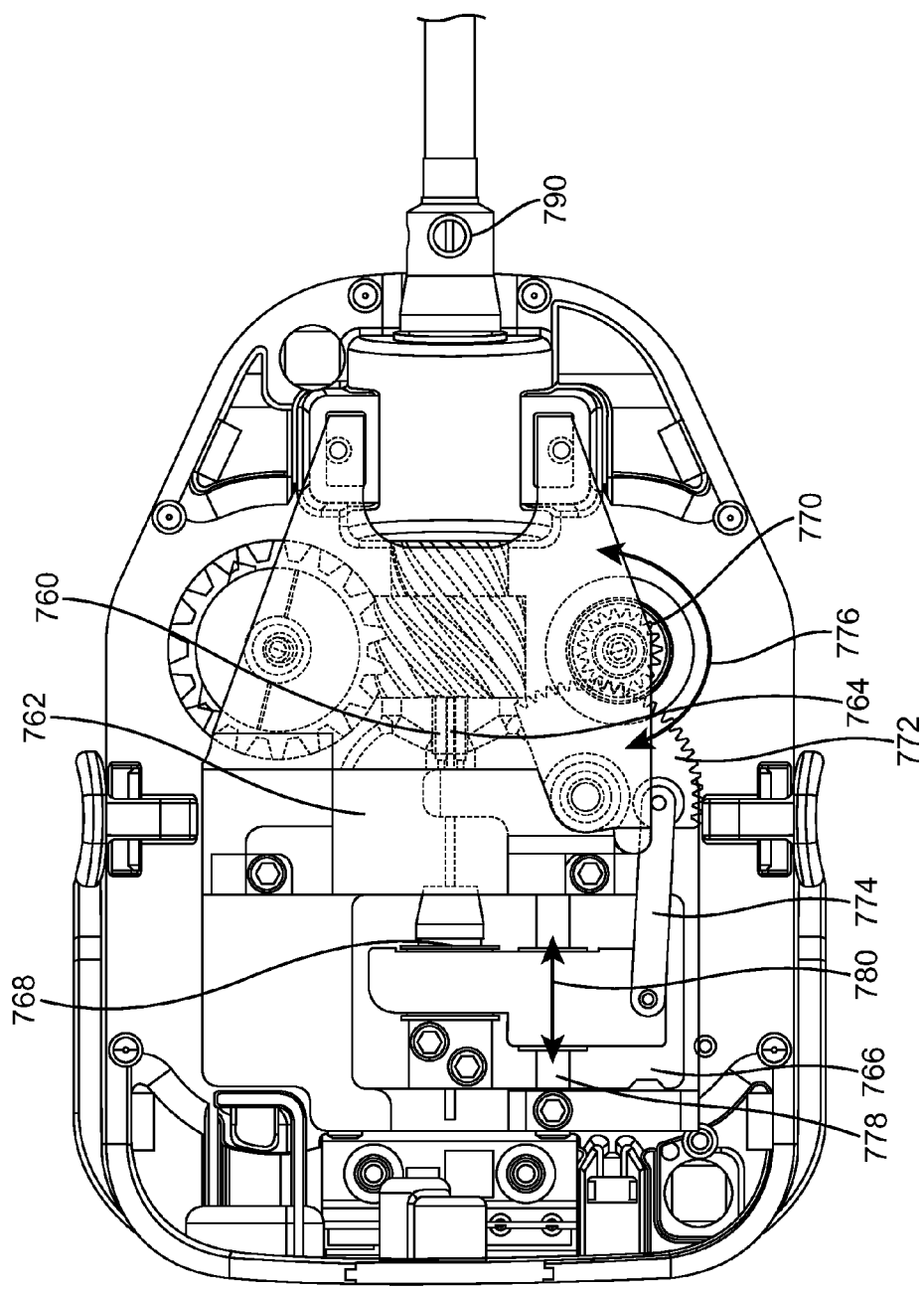
FIG. 7C is a plan view of a force transmission mechanism used in a push/pull instrument design.

FIG. 7C is a plan view of an illustrative implementation of a force transmission mechanism used in a push/pull instrument design. As shown in FIG. 7C, force isolation rods 760 extend out of the proximal end of the flexible instrument shaft and are joined with backing plate 762. Push/pull drive element rod 764 also extends out of the proximal end of the instrument shaft, and further extends through backing plate 762 to be coupled with slider 766. In this implementation, drive element rod 764 is coupled with linear slider 766 using a free rolling bearing 768. This free rolling bearing prevents the drive rod from twisting when the instrument shaft is rolled (i.e., provides an unconstrained roll DOF). Push/pull drive gear 770 is engaged with lever gear 772. Lever gear 772 is coupled to slider 766 with link (offset crank) 774. As drive gear 770 turns back and forth as indicated by arrows 776, slider 766 slides along shaft 778 as indicated by arrows 780, thus moving drive element 764 along the instrument shaft's longitudinal axis. The FIG. 7C shaft roll implementation is substantially similar to the implementation described above with reference to FIG. 7B.

FIG. 7C also shows an illustrative flush fluid entry port 790 at the proximal end of the instrument shaft. In the depicted implementation, the flush fluid port is made part of the assembly that couples the shaft body tube to the roll gear. Flush fluid may be directed into the port to clean components inside the shaft. For example, even though an actuating drive rod or cable may extend through a wipe seal at the distal end of the shaft, a small amount of body fluid may pass the seal and enter the inside of the shaft body.

Figure 7D:
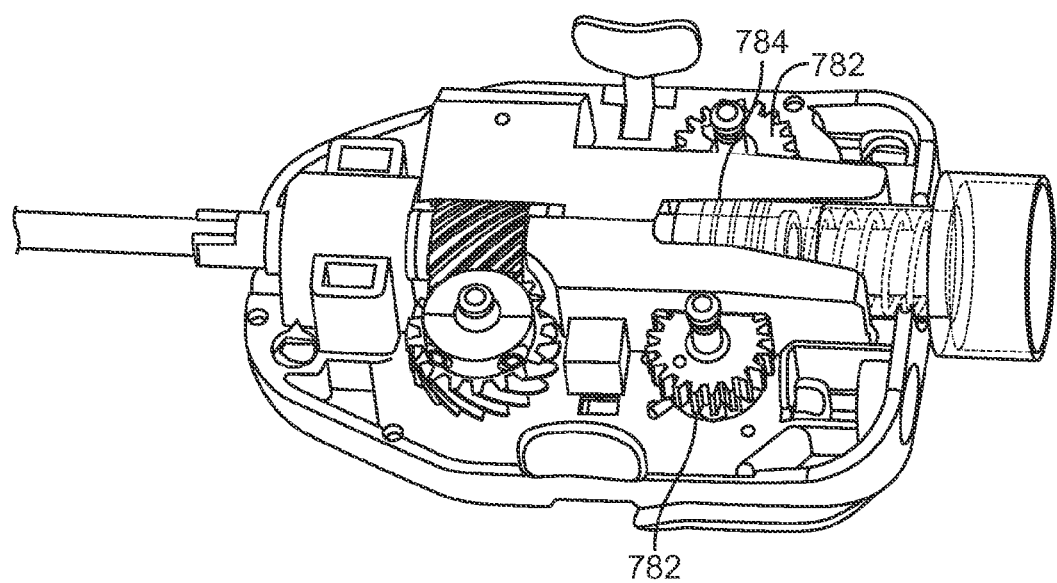
FIG. 7D is a perspective view of another force transmission mechanism used in a push/pull instrument design.

FIG. 7D is a perspective view of another illustrative implementation of a force transmission mechanism used in a push/pull instrument design. As shown in FIG. 7D, two pinion drive gears 782 engage a rack gear 784 between them. As depicted, the rack is round, and a flat rack may be used instead. The push/pull drive element rod is coupled to the rack (e.g., with a free rolling bearing as described above). The implementation depicted in FIG. 7D uses two extra drive elements and associated interface disks (not shown; see e.g., FIG. 7A) positioned towards the rear of the force transmission mechanism, and the drive elements rotate in opposite directions to move the rack along the instrument shaft's longitudinal axis. This implementation design uses fewer parts, and so is less expensive and simpler to manufacture than the implementation shown in FIG. 7C, although this FIG. 7D implementation does use an extra drive element in the force transmission mechanism's interface to the robotic manipulator. An advantage of using more than one drive element, however, is that the mechanism can exert more force in comparison to using only a single, comparable drive element (e.g., effectively two times as much if two drive elements are used).

It should be understood that principles described for moving an end effector component may be adapted for use in instruments that include a movable wrist mechanism or other mechanism at the distal end of the instrument shaft. Such a wrist mechanism allows an end effector orientation to be changed without changing shaft position.

Various design aspects may be used for the flexible instrument shafts. The following descriptions disclose example implementations of flexible shafts used for instruments with a movable end effector component, and it should be understood that the principles described (e.g., ways of stiffening) may be adapted for shafts that do not have an end effector with a moving component. It should also be understood that the principles may be adapted to instrument aspects that include a movable wrist mechanism or other mechanism at the distal end of the instrument shaft.

Figure 8A:
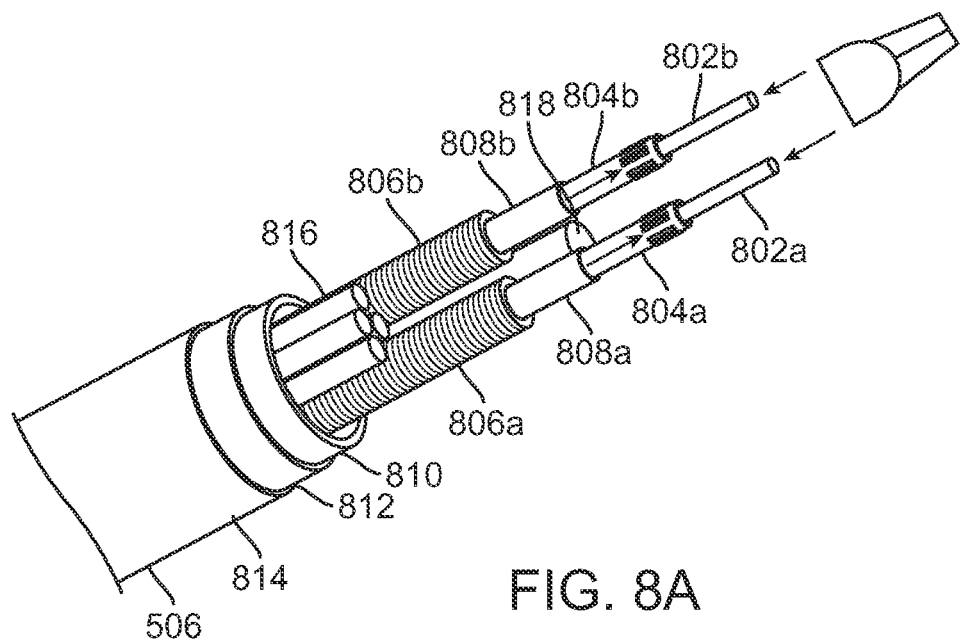
FIG. 8A is a cutaway perspective view of a portion of an instrument shaft.

FIG. 8A is a cutaway perspective view that shows an illustrative structure of a portion of instrument shaft 506. Two tension elements 802a,802b extend through a distal portion of shaft 506 and are coupled to operate the end effector (shown diagrammatically; e.g., a 5 mm diameter class surgical end effector used in da Vinci® Surgical System instruments). Tension elements 802a,802b may be separate, or they may be parts of the same element that, for example, wraps around a pulley in the end effector. In one implementation, tension elements 802a,802b are 0.018-inch tungsten wire. As shown in FIG. 8A, proximal ends of tension elements 802a,802b are coupled (e.g., crimped, etc.) to distal ends of second tension elements 804a,804b that further extend proximally through most of shaft 506. In one implementation, tension elements 804a,804b are 0.032-inch stainless steel hypotubes. At the proximal end (not shown) tension elements 804a,804b are coupled to transmission mechanism 502 using wires coupled in a similar manner, as described above.

As shown in FIG. 8A, tension elements 804a,804b extend through support tubes 806a,806b respectively, which guide tension elements 804a,804b and keep them from buckling or kinking within shaft 506. In one implementation, support tubes 806a,806b are stainless steel (e.g., 304V (vacuum melt that reduces friction)) coil tubes (0.035-inch inner diameter; 0.065-inch outer diameter), and other materials and structures may be used. To reduce friction as each tension element slides inside its support tube, a friction reducing sheath 808a,808b is placed between the tension element and the inner wall of the support tube. In one implementation, sheaths 808a,808b are PTFE, and other materials may be used. Both support tubes 806a,806b are placed within a single inner shaft tube 810. In one implementation, a flat-spiral stainless steel wire is used for inner shaft tube 810 to provide torsional stiffness during roll. An outer shaft tube 812 (e.g., braided stainless steel mesh or other material suitable to protect the shaft components) surrounds inner shaft tube 810. An elastomer skin 814 (e.g., Pellothane®, or other suitable material) surrounds the outer shaft tube 812. Skin 814 protects the inner components of shaft 506 from direct contamination by, e.g., body fluids during surgery, and the skin facilitates shaft 506 sliding within the curved cannula. In some implementations shaft 506 is approximately 5.5 mm (0.220 inches) outer diameter.

In one example implementation, the support tube and tension element assemblies may be dip coated in PTFE to provide a "sheath" that reduces friction. The space between the coils is filled in by the dip coating material to form a tube. In another example implementation, wire is pre-coated before the coil is wound, and the coil is then baked to remelt the coating and form the solid tube. The ends of the tube may be sealed around the tension elements to prevent contamination (e.g., body fluids) from entering between the tension element and the coil tube.

Shaft 506 may include additional components. As shown in FIG. 8, for example, in some implementations one or more stiffening rods 816 run through various portions of shaft 506. The number, size, and composition of rods 816 may be varied to provide the various stiffnesses of portions 506a-506c, as described above. For example, in some implementations rods 816 are stainless steel. In addition, some implementations one or more additional rods 818 of another material may run through one or more portions of shaft 506. For example, FIG. 8A shows a second rod of PEEK that in one implementation runs through distal section 506c to provide stiffness in addition to the stiffness from rods 516. In addition, one or more supplemental tubes to provide, e.g., suction and/or irrigation or flushing for cleaning may be included in shaft 506, either in addition to or in place of the stiffening rods. And, additional tension elements may be included to operate, e.g., an optional multi-DOF wrist mechanism at the distal end of the instrument shaft.

Figure 8B:
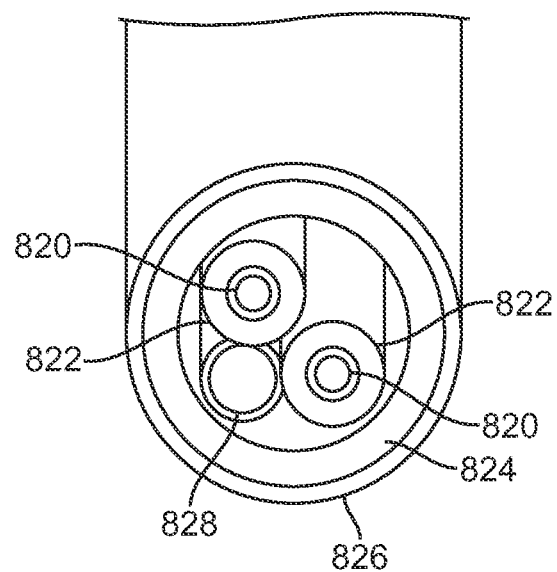
FIG. 8B is a cross-sectional diagrammatic perspective view of another instrument shaft design.

FIG. 8B is a cross-sectional diagrammatic perspective view of another implementation of an instrument shaft design. As shown in FIG. 8B, two hypotube tension elements 820 with PTFE coating are positioned within force isolation coil tubes 822. An optional fluorinated ethylene propylene (FEP) insulation layer may surround the coil tubes. A PEEK body tube 824 surrounds the tension elements and coil tubes, and an FEP heat shrink skin 826 surrounds the body tube. An optional flush tube 828 may be placed inside body tube 824, and it is configured so that cleaning fluid from the proximal end of the shaft travels through the cleaning tube to the distal end of the shaft, and then back through the body tube to flush out, e.g., contaminating body fluids. The instrument materials are selected, nevertheless, to allow the instrument to be autoclavable for sterilization.

Figure 8C:
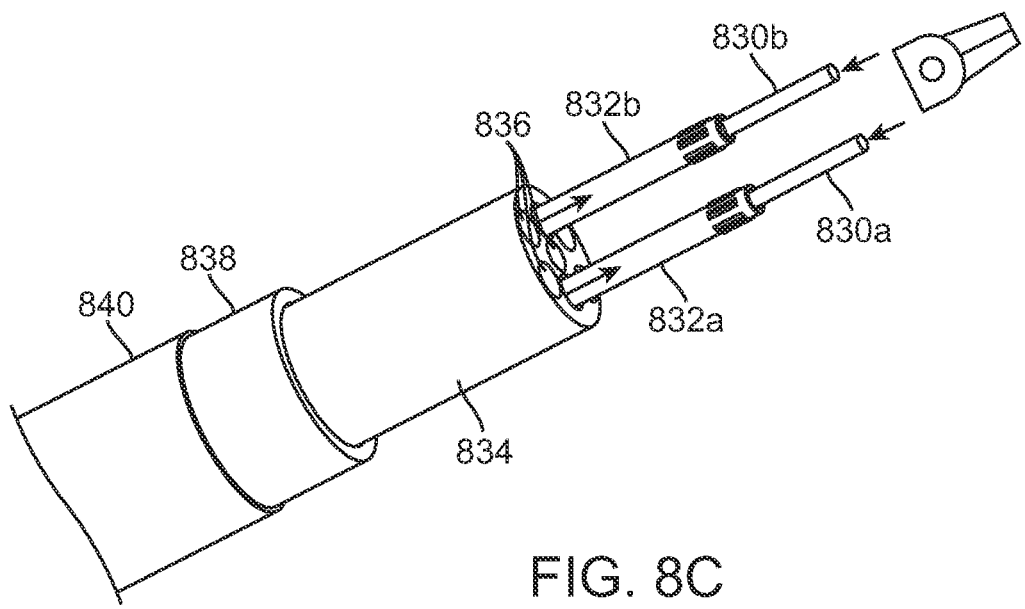
FIG. 8C is a cutaway perspective view of a portion of another instrument shaft.

FIG. 8C is a cutaway perspective view that shows another illustrative structure of a portion of instrument shaft 506. Tension elements 830a, 830b, 832a, and 832b are similar to tension elements 802a, 802b, 804a, and 804d described above. The tension elements are each routed through individual channels in multi-channel support tube 834. In one implementation, tube 834 is a FEP extrusion with multiple channels 836, and other materials may be used. FEP provides a low-friction surface against which the tension elements slide. One or more stiffening rods (not shown) similar to those disclosed above may be routed through various other channels 836 in support tube 834 to provide desired stiffnesses for each of the instrument shaft sections 506a-506c. A seven-channel tube 834 (six channels arranged around a central channel) is shown in FIG. 8C, and a stiffening rod or other element may be inserted into the center channel. Additional cables, e.g., to operate an optional multi-DOF wrist mechanism at the distal end of shaft 506, may be routed through other channels in tube 834. Alternatively, other functions, such as suction and/or irrigation, may be provided through the channels.

FIG. 8C further shows a shaft body tube 838 (e.g., extruded PEEK or other suitable material) surrounding support tube 834 to provide axial and torsional stiffness to shaft 506. An outer skin or coating 840 surrounds body tube 838 to reduce friction as shaft 506 slides inside the curved cannula and to protect the shaft components. In one implementation, skin 840 is a 0.005-inch layer of FEP that is heat shrunk around body tube 838, and other suitable materials may be used. In one implementation of the structure shown in FIG. 8C, the shaft 506 outer diameter is approximately 5.5 mm (0.220 inches), with a single extrusion PEEK body tube having an outer diameter of approximately 5.0 mm and an inner diameter of about 3.5 mm. PEEK is used because its stiffness (modulus of elasticity, or Young's modulus) is low enough to allow bending with low enough radial force to limit friction inside the curved cannula so that instrument I/O is not affected in a meaningful way, but its modulus of elasticity is high enough to provide good cantilever beam stiffness for the shaft distal portion 506c that extends beyond the distal end of the curved cannula, to resist buckling of any portion of the shaft between the transmission mechanism and the proximal end of the cannula, and to transmit roll motion and torque along the length of the instrument shaft with adequate stiffness and precision.

Figure 8D:
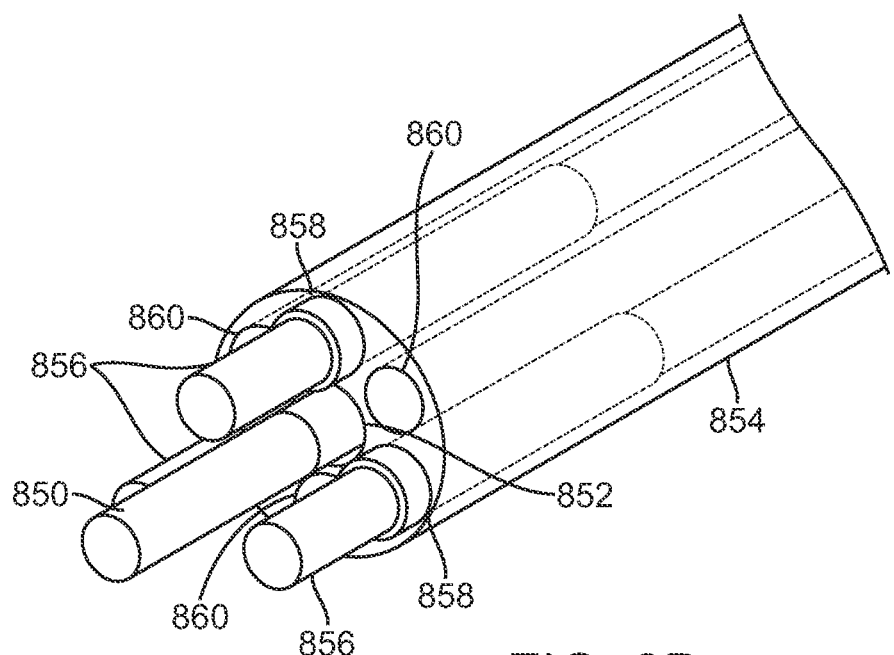
FIG. 8D is a diagrammatic perspective view of yet another instrument shaft design.

FIG. 8D is a diagrammatic transparent perspective view that shows yet another implementation a flexible instrument shaft design. As shown in FIG. 8D, a push/pull drive element 850 extends through a center channel 852 in a multi-channel tube 854, which is similar to tube 834 described above. Three force isolation/stiffening rods 856 as described above extend through three of the channels 858 surrounding the center channel. As shown in FIG. 8D, the distal ends of the rods 856 include stainless steel plugs that fit into the channels. In the depicted implementation, the remaining three channels 860 surrounding the center channel are left open and are used as flush fluid channels. In other implementations, however, other elements may be routed through one or more of the channels 860. The surrounding instrument shaft body tube and skin are omitted from the drawing for clarity.

Figure 9A:
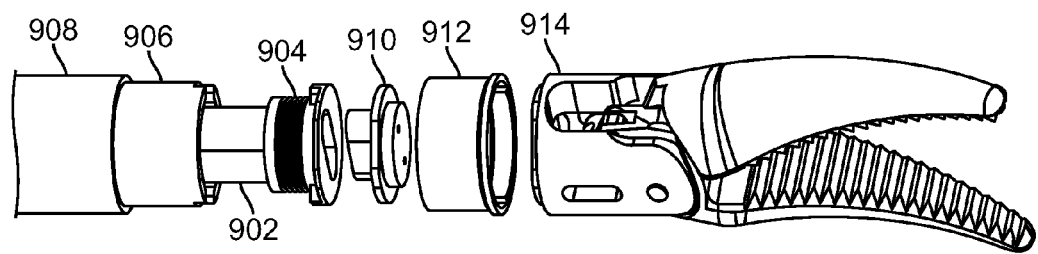
FIG. 9A is an exploded perspective view of the distal end of a flexible shaft instrument.

FIG. 9A is an exploded perspective view of an implementation of the distal end of a flexible shaft instrument. As shown in FIG. 9A, two coil tubes 902 are coupled to distal end cap 904. The coil tubes are positioned inside body tube 906 with outer skin 908 as described above (the tension elements are not shown). A tension element seal 910 is fitted into end cap 904, and the tension elements extend through seal 910, which keeps fluids from entering into the coil tubes. In one illustrative implementation, seal 910 is a molded silicone wipe seal. Adaptor cap 912 is positioned over the distal end of the body tube, and the end effector clevis 914 is coupled to the adaptor cap.

Figure 9B:
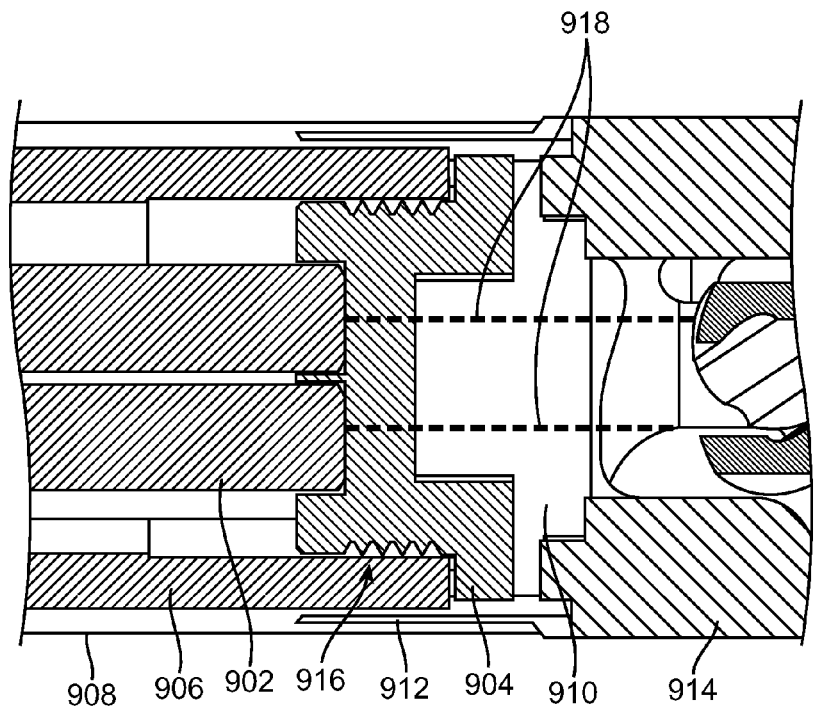
FIG. 9B is a cross-sectional view of the implementation depicted in FIG. 9A.

FIG. 9B is a cross-sectional view of the implementation depicted in FIG. 9A. In FIG. 9B it can be seen that end cap 904 includes ridges 916 that enable the cap to be swaged inside body tube 906. Coil tubes 902 are positioned against cap 904, and tension element cables 918 are routed through cap 904 and seal 910. Adaptor cap 912 is swaged over body tube 906, and in the illustrative implementation is tapered to allow FEP heatshrink skin 908 to cover a portion of cap 912. End effector clevis 914 is coupled (e.g., laser welded) to adaptor cap 912. Although not shown, a single clevis and adapter cap piece (not shown) may be substituted for the cap 912 and clevis 914. The single piece reduces manufacturing cost and complexity by eliminating the laser weld.

FIG. 9C is a diagrammatic view that illustrates a pull/pull type end effector that may be at the distal end of the flexible shaft instruments. As depicted in FIG. 9C, pulling on one cable opens the end effector jaws, and pulling on the other cable closes the end effector jaws.

FIG. 9D is an exploded perspective view of another implementation of the distal end of a flexible shaft instrument. As shown in FIG. 9D, end cap 920 fits inside the distal end of shaft body tube 922. Wipe seal 924 covers the opening in end cap 920, and push/pull drive rod connector 926 extends through end cap 920 and seal 924 to couple with the movable component of the end effector. End effector clevis and attachment cap assembly 928 fits over the end of shaft body tube 922. The components are assembled in a manner similar to that described in relation to FIG. 9B (e.g., the use of swaging, etc.). The opening in seal 924 for the drive rod connector is slightly undersized, and compressing the seal before swaging assembly 928 to the shaft body tube further closes the seal around the drive rod connector.

FIG. 9E is a diagrammatic view that illustrates a push/pull type end effector that may be at the distal end of the flexible shaft instruments (an illustrative clip applier end effector is shown). As depicted in FIG. 9E, pushing on the drive rod closes the end effector jaws, and pulling on the drive rod opens the end effector jaws.

Figure 9F:
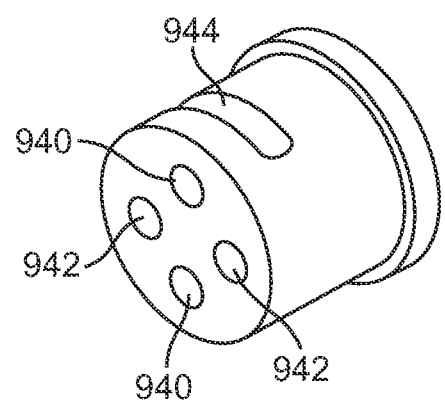
FIG. 9F is a diagrammatic perspective view of an instrument shaft end cap.

FIG. 9F is a diagrammatic perspective view of an implementation of an end cap designed to facilitate cleaning. Two coil tubes as described above are joined with the end cap at openings 940. Two flush fluid tubes as described above are joined with the end cap at openings 942. An elongate bore 944 is placed in the end cap to intersect each of the openings 940,942. The ends of the bore are sealed by the swage connection between the end cap and the body tube, and so a chamber is formed (the swage ridges are omitted from the drawing for clarity). Fluid for cleaning travels distally through the instrument shaft via the flush tubes, enters the chamber, and is redirected proximally through the interiors of the coil tubes for cleaning. Similarly, in a push/pull type instrument implementation, a distal end chamber receives cleaning fluid through one or more channels in a multi-channel support tube and redirects the fluid through the center channel to flush away contaminates for cleaning.

Figure 10:
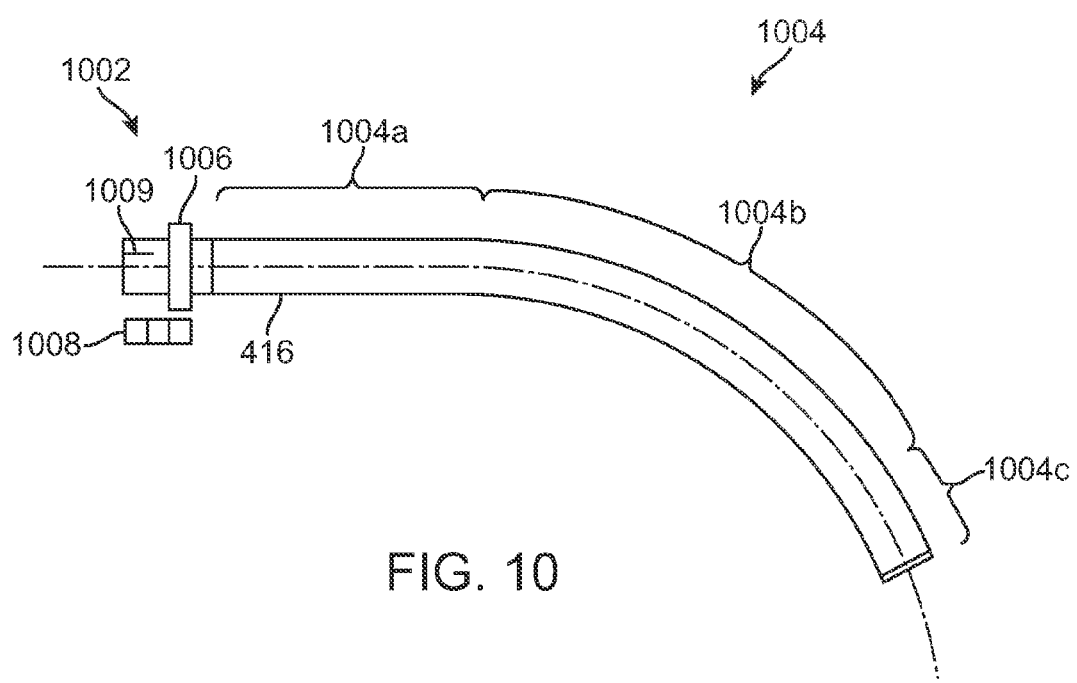
FIG. 10 is a diagrammatic view of a curved cannula.

FIG. 10 is a diagrammatic view of an illustrative curved cannula 416. As shown in FIG. 10, cannula 416 includes a mounting section 1002 and cannula body section 1004. The mounting section 1002 is configured to be mounted on a robotic system manipulator (e.g., PSM 204). In some implementations, one or more features 1006 are placed on the mounting section 1002 to be sensed by sensors 1008 in the manipulator's cannula mount. The presence of a feature 1006 as sensed by the sensors 1008 may indicate, e.g., that the cannula is properly mounted and the type of cannula (e.g., straight or curved, cannula length, curve radius, etc.). In one implementation the features 1006 are raised annular metal rings and the corresponding sensors 1008 are Hall effect sensors.

Figure 10A:
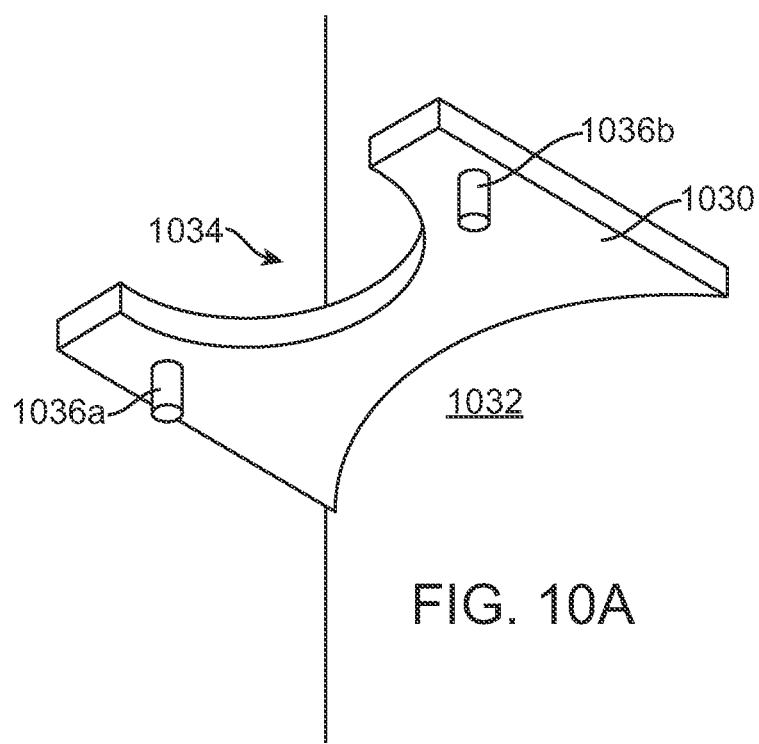
FIG. 10A is a diagrammatic view of an aligning key feature.

Mounting section 1002 may also include a mechanical key feature 1009 that mates with a corresponding feature on the manipulator to ensure that the cannula is mounted with the proper orientation with reference to the manipulator's insertion axis. In this way, for example, "left" and "right" curving cannulas may be made. In addition, to distinguishing left versus right curve orientation, the keyed feature may be used to ensure that the cannula is rolled at the proper angle in the manipulator mount so that instruments approach the surgical site at a desired angle. Knowledgeable persons will understand that many various mechanical key features may be used (e.g., mating pins/holes, tabs/grooves, balls/detents, and the like). FIG. 10A illustrates one example key feature. As shown in FIG. 10A, key feature 1030 is attached (e.g., welded) to the side of a mounting bracket 1032 for a curved cannula. Key feature 1030 includes a recess 1034 that receives a portion of a robotic manipulator's cannula mounting bracket and two vertical alignment pins 1036a and 1036b. Alignment pins 1036a and 1036b mate with corresponding alignment holes in the manipulator's mounting bracket to ensure the cannula's proper roll orientation with reference to the manipulator.

Figure 11A:
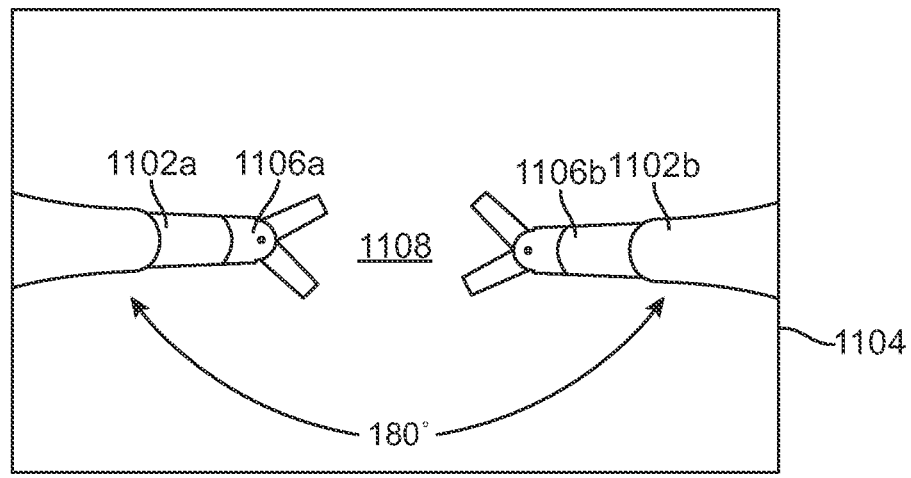
FIGS. 11A and 11B illustrate cannula orientations.
Figure 11B:
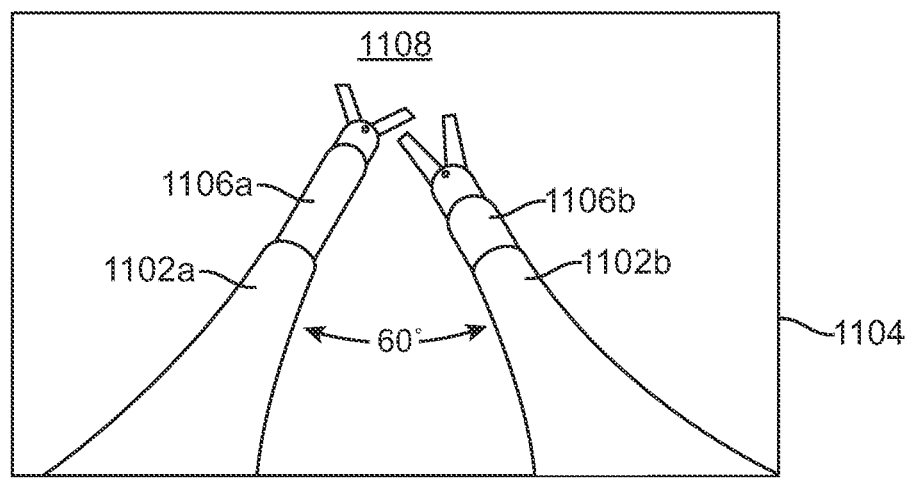

FIGS. 11A and 11B are diagrammatic views of the distal ends 1102a and 1102b of two curved cannulas as a surgeon might see them in the surgeon's console's 3-D display 1104, which outputs images captured in the endoscope's field of view. In the display, the curved cannulas extend away from the endoscope to enable the instruments 1106a and 1106b to reach tissue 1108 at the surgical site. The cannulas may be mounted on the manipulators at various roll angles, or the manipulators may be oriented during surgery, so that the instruments approach the surgical site at various angles. Accordingly, the cannula roll orientations may described in several ways. For example, the cannula roll angles may be described in relation to each other. FIG. 11A shows that in one implementation the cannulas may be oriented with their distal curves lying approximately in a single common plane, so that the instruments extend from directly opposite angles towards the surgical site. FIG. 11B shows that in one implementation the cannulas may be oriented with their distal curves lying in planes that are angled with reference to each other, e.g., approximately 60 degrees as shown, so that the instruments extend from offset angles towards the surgical site. Many cannula curve plane relation angles are possible (e.g., 120, 90, 45, 30, or zero degrees). Another way to express the cannula roll orientation is to define it as the angle between the plane that includes the cannula's curve and a plane of motion for one of the manipulator's degrees of freedom (e.g., pitch). For example, a cannula may be mounted so that its curve lies in a plane that is angled at 30 degrees to the manipulator's pitch DOF.

Figure 11C:
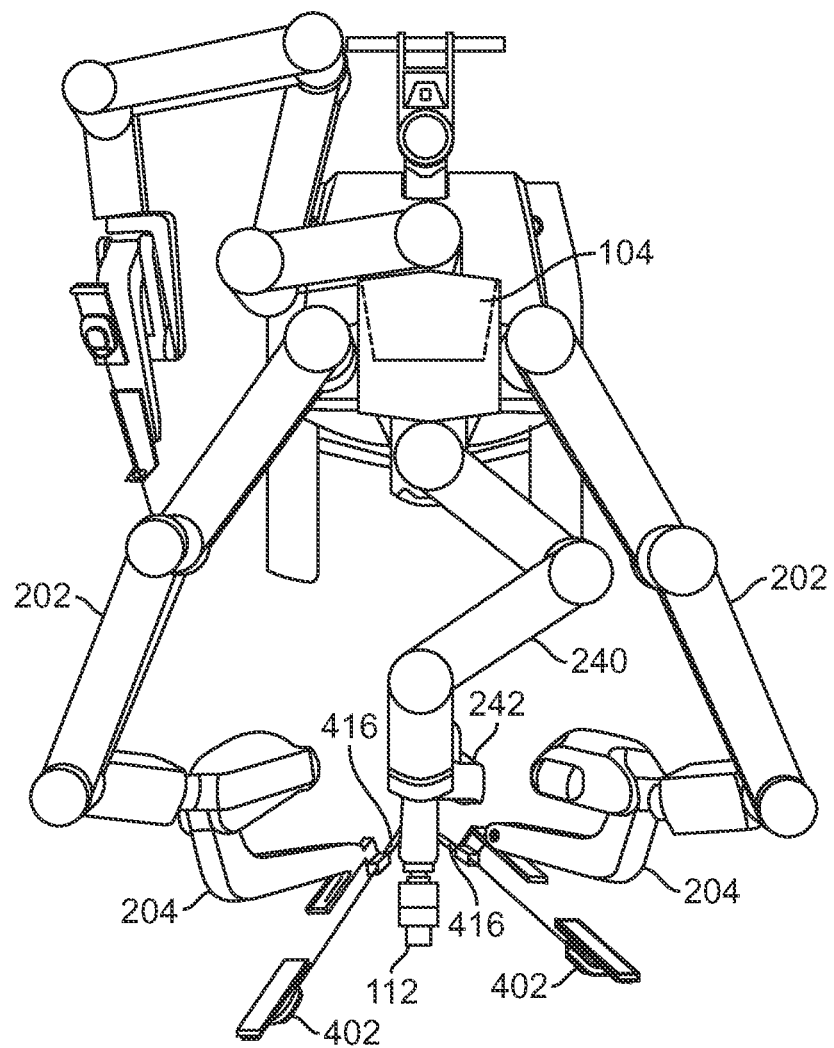
FIG. 11C is a plan view of a robotic surgical system with manipulators in an example pose to position curved cannulas.

Accordingly, one illustrative way to obtain the position of the instrument cannulas as shown in FIG. 11B is to position the two PSM's facing one another with their pitch motion planes approximately parallel (the planes will be slightly offset so that the two cannulas do not intersect at their centers of motion). Then, each curved cannula is oriented at approximately 30 degrees with reference its corresponding PSM's pitch motion plane. FIG. 11C is a plan view of a da Vinci® Surgical System in an illustrative configuration in which two PSM's 204 and the ECM 242 are posed to place curved cannulas 416 as described above with reference to FIG. 11B. It can be seen in FIG. 11C that, in contrast to the use of straight cannulas and instruments in a single body opening, the PSM's with curved cannulas have a reasonably large volume in which they can move without collision, which provides a correspondingly larger volume in which the instruments can move at the surgical site.

Referring again to FIG. 10, cannula body section 1004 is in some implementations divided into a proximal section 1004a, a middle section 1004b, and a distal section 1004c. Proximal section 1004a is straight, and its length is made sufficient to provide adequate movement clearance for the supporting PSM. Middle section 1004b is curved to provide the necessary instrument triangulation to the surgical site from a manipulator position that provides sufficient range of motion to complete the surgical task without significant collisions. In one implementation, middle section 1004b is curved 60 degrees with a 5-inch bend radius. Other curve angles and bend radii may be used for particular surgical procedures. For example, one cannula length, curve angle, and bend radius may be best suited for reaching from a particular incision point (e.g., at the umbilicus) towards one particular anatomical structure (e.g., the gall bladder) while another cannula length, bend angle, and/or bend radius may be best suited for reaching from the particular incision point towards a second particular anatomical structure (e.g., the appendix). And, in some implementations two cannulas each having different lengths and/or bend radii may be used.

The relatively tight clearance between the curved section's inner wall and the flexible instrument that slides inside requires that the curved section's cross-section be circular or near-circular shape throughout its length. In some implementations the curved cannula is made of 304 stainless steel (work hardened), and the curved section 1004b is bent using, e.g., a bending fixture or a computer numerical controlled (CNC) tube bender. For a 5.5 mm (0.220-inch) outer diameter instrument, in some implementations the curved cannula's inner diameter is made to be approximately 0.239 inches, which provides an acceptable tolerance for inner diameter manufacturing variations that will still provide good sliding performance for the instrument shaft.

Figure 12A:
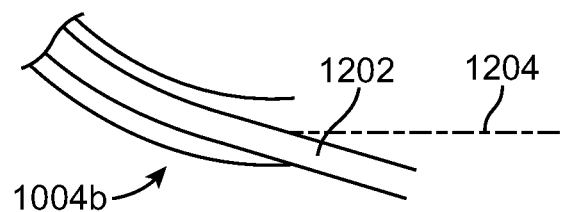
FIGS. 12A, 12B, and 12C are diagrammatic views that show an instrument shaft running through and extending from various cannula configurations.
Figure 12B:
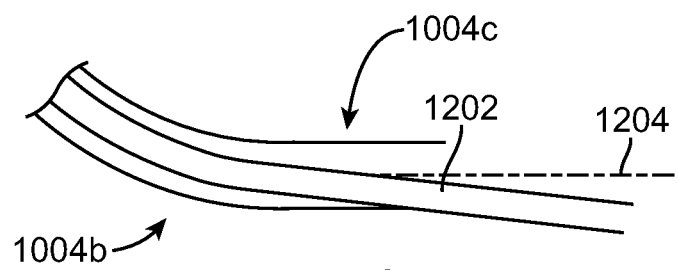

Distal section 1004c is a short, straight section of the cannula body. Referring to FIG. 12A, it can be seen that due to the small space (shown exaggerated for emphasis) between the instrument shaft outer diameter and the cannula inner diameter, and due to the instrument shaft's resiliency (although passively flexible, it may retain a tendency towards becoming straight), the distal section 1202 of the instrument shaft contacts the outer lip of the cannula's distal end. Consequently, if the curved cannula ends at curved section 1004b, the distal section 1202 of the instrument extends out of the cannula at a relatively larger angle (again, shown exaggerated) with reference to the cannula's extended centerline 1204. In addition, the angle between the instrument shaft and the outer lip causes increased friction (e.g., scraping) during instrument withdrawal. As shown in FIG. 12B, however, adding distal section 1004c to the cannula lessens the angle between the distal section 1202 and the cannula's extended centerline 1204 and also lessens the friction between the outer lip and the instrument shaft.

Figure 12C:
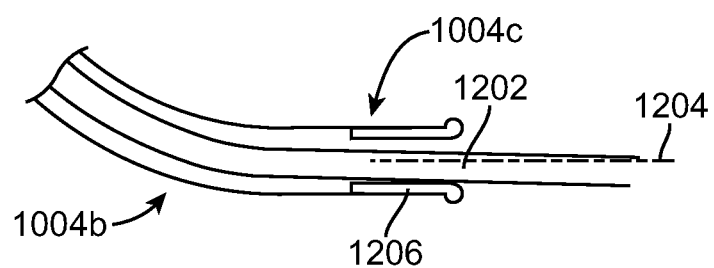

As shown in FIG. 12C, in some implementations, a sleeve 1206 is inserted into the distal end of distal section 1004c. Sleeve 1206 necks down the curved cannula's inner diameter at the distal end, and so further assists extending the distal section 1202 of the instrument shaft near the cannula's extended centerline 1204. In some implementations sleeve 1206's outer lip is rounded, and sleeve 1206's inner diameter is relatively close to the instrument shaft's outer diameter. This helps reduce possible tissue damage by preventing tissue from being pinched between the instrument shaft and the cannula during instrument withdrawal. In some implementations sleeve 1206 is made of 304 stainless steel and is approximately 0.5 inches long with an inner diameter of approximately 0.225 inches. Sleeve 1206 may also be made of a friction reducing material, such as PTFE. In an alternate implementation, rather than using a separate sleeve 1206, the distal end of the curved cannula may be swaged to reduce the cannula's inner diameter so as to produce a similar effect. Other ways of necking down distal section 1004c include, for example, drawing down the cannula tube or welding a smaller diameter tube to the end of the cannula tube.

Various lengths of the straight distal section may be used to provide support for flexible instruments at various working depths. For example, one cannula may have a curved section with a particular bend radius and a relatively shorter straight distal section, and a second cannula may have a curved section with the same particular bend radius but with a relatively longer straight distal section. The cannula with the relatively longer straight distal section may be used to position its associated instrument to reach a surgical site relatively farther within a patient, and the cannula with the relatively shorter straight distal section may be used to position its associated instrument to reach a surgical site relatively nearer the single port entry location. As described below, control aspects of each of these identically curved cannulas may be effectively the same, and so in some implementations each cannula is clearly labeled (marked, color coded, etc.) to indicate to surgical personnel the length of its straight distal section.

Since various straight distal section lengths may be used for cannulas with identical curved sections, and since these various distal section lengths may not be identified to the system, the system's information about the instrument's insertion depth within the cannula may not correctly identify the instrument's distal end position with reference to a cannula's distal end. This situation may be a problem for situations such as the use of electrocautery instruments, in which for safety the instrument should not be energized until its distal end (i.e., the electrocautery end effector and any associated exposed energized parts) is past the distal end of an electrically conductive curved cannula. Therefore, in some aspects a cannula end clearance detection system is used to determine that a distal part of an instrument is safely beyond the distal end of the cannula.

Figure 10B:
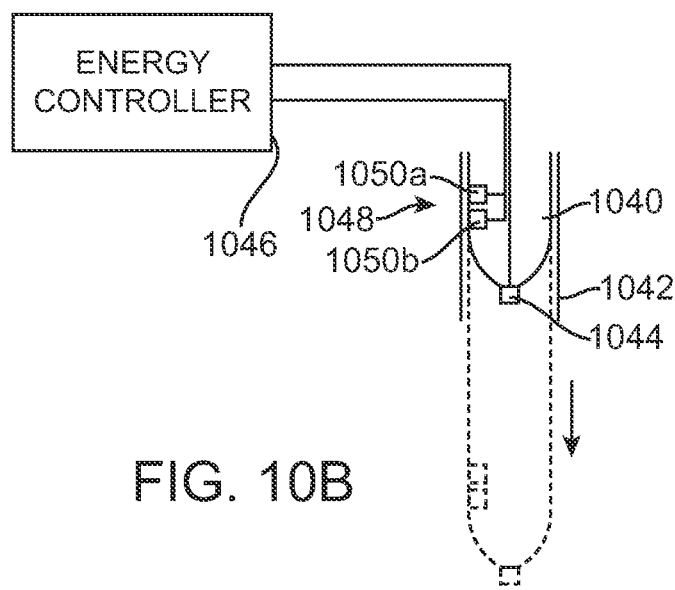
FIG. 10B is a schematic view of a cannula end clearance detection system.

FIG. 10B is a schematic view that illustrates one implementation of a cannula end clearance detection system. As shown in FIG. 10B, a distal part 1040 of an instrument is still within a distal straight section of a cannula 1042. The distal part 1040 includes an electrocautery end effector 1044, which receives electrocautery energy from energy controller 1046. The distal part 1040 also includes a detector assembly 1048, which in FIG. 10B is depicted as, e.g., an optical reflective sensor (various other sensor types may be used, such as a Hall effect sensor). Light generated by sensor component 1050a is reflected from the inner wall of cannula 1042 and is received by sensor component 1050b (there is a small gap between the instrument and the cannula, which provides the reflectance optical path). Energy controller 1046 is coupled to detector assembly 1048, and so the detector assembly indicates if the distal end of the instrument is within or past the distal end of the cannula. As the distal end of the instrument is inserted beyond the distal end of the cannula, as indicated in dashed lines, energy controller 1046 receives an indication from detector assembly 1048 and energizes end effector 1044. Implementations of a clearance detection system may be used for various instruments (e.g., activation safety for laser instruments, automatic positioning of mechanical wrist assembly for instrument withdrawal, etc.), and one or more sensors may be placed instead on the cannula or on both the instrument and cannula.

Figure 13:
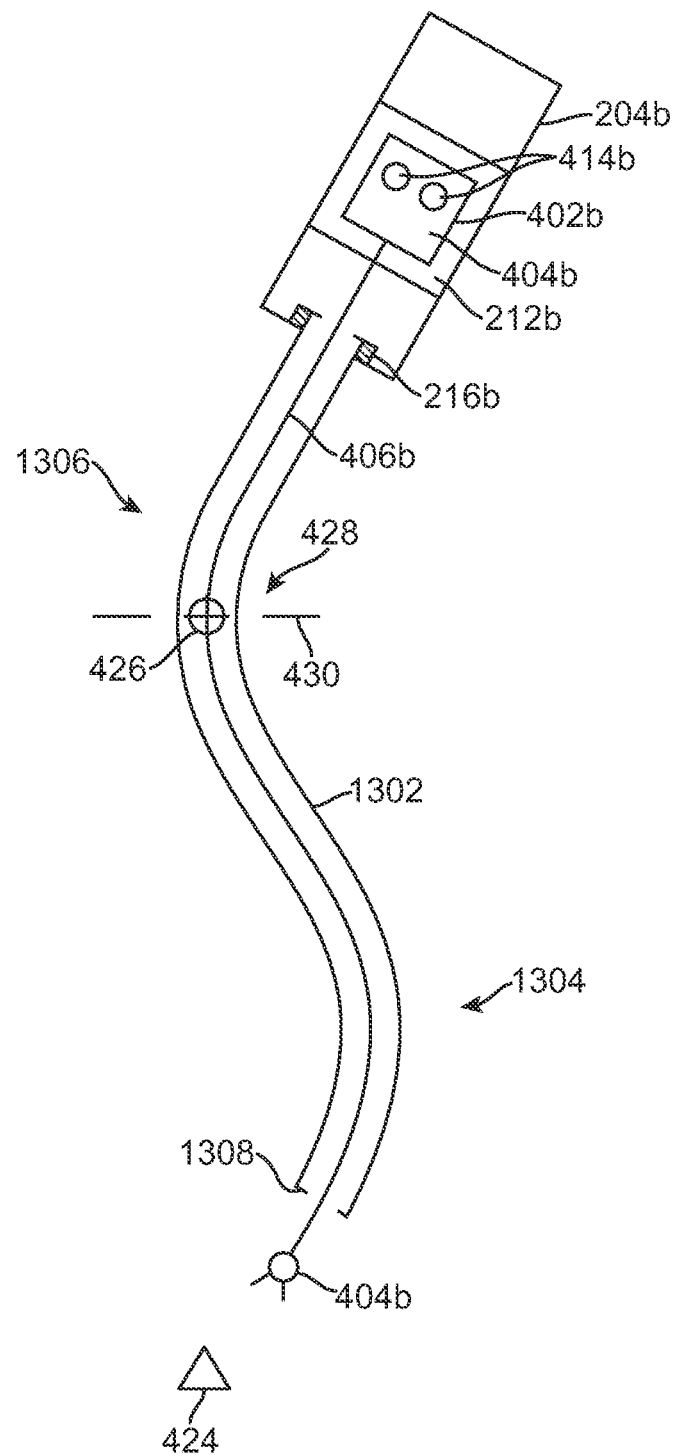
FIG. 13 is a schematic view that illustrates another curved cannula and flexible instrument combination.

FIG. 13 is a schematic view that illustrates an alternate implementation of a curved cannula and flexible instrument combination. Instead of a simple C-shaped bend as described above, curved cannula 1302 has a compound S-shaped bend (either planar or volumetric). In one illustrative implementation, each bend has about a 3-inch bend radius. Distal bend section 1304 provides triangulation for the surgical instrument, and proximal bend 1306 provides clearance for, e.g., PSM 204b (alternatively, in a manual implementation, for the surgical instrument handles and the surgeon's hands). As depicted, passively flexible shaft 404b of robotically controlled surgical instrument 402b extends through curved cannula 1302 and beyond the cannula's distal end 1308. A second curved cannula and flexible instrument combination is omitted from the drawing for clarity. The use of S-shaped curved cannulas is similar to the use of C-shaped curved cannulas as disclosed herein. For an S-shaped cannula, however, in a reference frame defined for the endoscope's field of view, the manipulator that controls the instrument is positioned on the same side of the surgical site as the corresponding end effector. Since the multiple bends in the S-shaped cannula cause contact between the instrument shaft and the cannula wall at more points along the length of the cannula than the C-shaped cannula, with similar normal forces at each point, the I/O and roll friction between the instrument and the cannula is relatively higher with an S-shaped cannula.

The curved cannulas described herein are described as being rigid, which means that they are effectively rigid during use. It is well known that certain materials or mechanisms may be bent into one curve shape and then later bent again into another curve shape. For example, a flexible tube of many short links may be effectively rigidized by compressing the links along the tube's longitudinal axis, so that friction prevents the links from moving with reference to one another. Or, inner and outer tubes may be radially compressed together to prevent them from sliding with reference to one another. See e.g., U.S. Pat. No. 5,251,611 (filed May 7, 1991) (disclosing "Method and Apparatus for Conducting Exploratory Procedures") and U.S. Patent Application Pub. No. US 2008/0091170 A1 (filed Jun. 30, 2006) (disclosing "Cannula System for Free-Space Navigation and Method of Use"), both of which are incorporated herein by reference. And so, in some implementations the curved sections of the curved cannulas as described herein may be re-bendable (repositionable) into various curve shapes. In order to determine the kinematic parameters for the curve shape, the parameters being necessary for control as described below, known sensing technologies may be used. Such technologies include measuring motor positions for tendons (or the displacements of the tendons themselves) used to re-bend the curved section, or the use of optical fiber shape sensing to determine the curve shape. See e.g., U.S. Pat. No. 5,798,521 (filed Feb. 27, 1997) (disclosing "Apparatus and Method for Measuring Strain in Bragg Gratings"), U.S. Patent Application Pub. No. US 2006/0013523 A1 (filed Jul. 13, 2005) (disclosing "Fiber Optic Position and Shape Sensing Device and Method Relating Thereto), U.S. Patent Application Pub. No. US 2007/0156019 A1 (filed Jul. 20, 2006) (disclosing "Robotic Surgery System Including Position Sensors Using Fiber Bragg Gratings), and U.S. Patent Application Pub. No. US 2007/0065077 A1 (filed Sep. 26, 2006) (disclosing "Fiber Optic Position and Shape Sensing Device and Method Relating Thereto"), all of which are incorporated herein by reference.

The various aspects and implementations described above have concentrated on the use of two curved cannulas to provide triangulation at the surgical site for their associated flexible shaft instruments. In some aspects and implementations, however, a single curved cannula and its associated flexible shaft instrument may be used together with a straight cannula and its associated rigid shaft instrument. Although such an implementation provides less instrument triangulation at the surgical site than, and may block the endoscope's surgical site image to a greater extent than, the double curved cannula implementation, the combination of a curved and straight cannula may be beneficial or even necessary to perform surgery in certain anatomical areas. Referring to FIG. 11C, for example, in one illustrative use of a curved cannula surgical system, the left side PSM 204 and its associated cannula and instrument may be temporarily removed from the single body opening, and the additional left side PSM (shown in a partially stowed position) may be posed to place its associated straight cannula and straight shaft instrument into the single body opening.

Further, aspects and implementations described above have concentrated on the illustrative use of a straight, rigid endoscope. In other aspects and implementations, however, a curved endoscope cannula may be used and a flexible shaft camera instrument may be inserted through the curved endoscope cannula. Such a flexible shaft camera instrument may use, for example, a flexible bundle of optical fibers to carry an image from the endoscope's distal end to a proximal end camera outside the body, or it may have a distal end imaging system (e.g., CMOS image sensor) mounted on the end of a passively flexible shaft. As with the straight, rigid endoscope, a flexible endoscope may be inserted, withdrawn, and rolled inside its associated cannula as described herein. An advantage of using a curved endoscope cannula is that it may provide a triangulated view of the surgical site that is less obstructed by surgical instruments or that provides a move beneficial perspective of a particular tissue structure. A straight shaft endoscope with an angled view (e.g., thirty degrees off axis) may also be used to provide an alternate view perspective.

Port Feature

FIG. 14A is a diagrammatic plan view of an illustrative implementation of a port feature 1402 that may be used with curved cannula and instrument combinations, and with an endoscope and one or more other instruments, as described herein. FIG. 14B is a top perspective view of the implementation shown in FIG. 14A. Port feature 1402 is inserted into a single incision in a patient's body wall. As shown in FIG. 14A, port feature 1402 is a single body that has five channels that extend between a top surface 1404 and a bottom surface 1406. Other implementations may have various numbers of ports in various locations on the port feature. A first channel 1408 serves as an endoscope channel and is sized to accommodate an endoscope cannula. In alternative implementations, channel 1408 may be sized to accommodate an endoscope without a cannula. As shown in FIG. 14A, endoscope channel 1404 is offset from port feature 1402's central axis 1410. If a surgical procedure requires insufflation, it may be provided via well known features on the endoscope cannula.

FIG. 14A shows two more channels 1412a and 1412b that serve as instrument channels and that are each sized to accommodate a curved cannula as described herein. Channels 1412*a*,1412*b* extend through port feature 1402 at opposite angles to accommodate the positioning of the curved cannulas. Thus, in some implementations channels 1412*a*,1412*b* extend across a plane that divides the port feature into left and right sides in an orientation shown in FIG. 14A. As shown in FIG. 14A, the instrument channels 1412*a* and 1412*b* are also offset from central axis 1410. During use, the remote centers of motion for the endoscope and instrument cannulas will be generally at middle vertical positions within their respective channels. By horizontally offsetting the endoscope channel 1408 and the instrument channels 1412*a*,1412*b* from the central axis 1410, a center point of this group of remote centers can be positioned approximately in the center of the port feature (i.e., in the center of the incision). Placing the remote centers close together minimizes patient trauma during surgery (e.g., due to tissue stretching during cannula motion). And, the port feature keeps the cannulas close to one another but resists the tendency for tissue to force the cannulas towards one another, thus preventing the cannulas from interfering with one another. Various channel angles may be used in various implementations in order to accommodate the particular configurations of the curved cannulas being used or to facilitate the required curved cannula placement for a particular surgical procedure.

FIG. 14A also shows two illustrative optional auxiliary channels 1414 and 1416 that extend vertically through port feature 1402 (the number of auxiliary channels may vary). The first auxiliary channel 1414's diameter is relatively larger than the second auxiliary channel 1416's diameter (various sized diameters may be used for each auxiliary channel). First auxiliary channel 1414 may be used to insert another surgical instrument (manual or robotic, such as a retractor or a suction instrument; with or without a cannula) through port feature 1402. As shown in FIG. 14A, endoscope channel 1408, instrument channels 1412*a*,1412*b*, and first auxiliary channel 1414 each include a seal (described below), and second auxiliary channel 1416 does not. And so, second auxiliary channel 1416 may likewise be used to insert another surgical instrument, or it may be used for another purpose better served by not having a seal in the channel, such as to provide a channel for a flexible suction or irrigation tube (or other non-rigid instrument), or to provide a channel for insufflation or evacuation (insufflation may be done using typical features on the endoscope cannula or other cannula).

The channel angles shown in the figures are illustrative, and it should be understood that various angled channels may be used. For example, an endoscope channel may extend at an angle between the port feature's top and bottom surfaces so that an endoscope does not exert a twisting force on the port feature during surgery (e.g., for an endoscope with a thirty-degree offset viewing angle, which may be used to look "down" at the surgical site to provide a field of view that is less obstructed by the curved cannulas and instruments). Likewise, one or more of the auxiliary channels may be angled. And, for implementations in which one or more curved cannulas is used in combination with a straight cannula, the straight cannula instrument channel may extend vertically between the port feature's top and bottom surfaces with the curved cannula instrument channel extending at an angle.

FIG. 14A shows that in some implementations, a port orientation feature 1418 may be positioned on top surface 1404. During use, the surgeon inserts port feature 1402 into the incision and then orients the port feature so that orientation indicator 1418 is generally in the direction of the surgical site. Thus the port feature is oriented to provide the necessary positions for the endoscope and curved cannulas in order to carry out the surgical procedure. Orientation feature 1418 may made in various ways, such as molded into or printed on top surface 1404. Likewise, FIG. 14A shows that in some implementations instrument port identification features 1420*a* and 1420*b* (the circled numerals "1" and "2" are shown) may be each positioned near one of the two instrument ports to identify the instrument channel. A similar identification feature may be placed on cannulas intended to be used on "left" or "right" sides, so that medical personnel may easily place a curved cannula in its proper port channel by matching the cannula and port channel identifications.

In some implementations port feature 1402 is made of a single piece of molded silicone (e.g., injection molded, compression molded, etc.). The port feature may have various durometer values (e.g., in the range of about 40 Shore 00 (3-4 Shore A) to about 15 Shore A), and in one illustrative implementation an injection molded silicone port feature has a durometer value of about 5 Shore A. Other configurations of port feature 1402 may be used, including multi-part port features with secondary cannulas that can accommodate, e.g., both the endoscope and curved cannulas as described herein.

Referring to FIG. 14B, in some instances the top surface 1404 and the bottom surface 1406 (not shown) are made concave. FIG. 14B also shows that in some instances port feature 1402 is waisted. The waist 1422 provides a top flange 1424 and a bottom flange 1426 that help hold port feature 1402 in position within the incision. Since port feature 1402 may be made of a soft, resilient material, the flanges 1424, 1426 formed by waist 1422 and the concave top and bottom surfaces are easily deformed to allow the surgeon to insert the port feature into the incision, and then the flanges return to their original shape to hold the port feature in place.

FIG. 15A is a diagrammatic cross-sectional view taken at cut line A-A in FIG. 14, and it illustrates how channel 1408*b* passes from the top to the bottom surfaces at an acute angle from one side to the other across a vertical midsection through port feature 1402. Channel 1408*a* is similarly routed in the opposite direction. The vertical position at which the two channels cross (in the FIG. 15A orientation, channel 1412*a* (not shown) is closer to the viewer, crossing the port feature from upper right to lower left) is approximately the vertical location of the respective cannula remote centers of motion when properly inserted. As mentioned above, in some implementations a seal may be placed in one or more of the channels through port feature 1402, and FIG. 15A shows an example of such a seal illustratively positioned at or effectively at the vertical location of the cannula remote center of motion.

FIG. 15B is a detailed view of an example implementation of a seal 1502 within instrument channel 1412*b*. As shown in FIG. 15B, seal 1502 includes an integrally molded solid ring 1504 that extends from channel 1412*b*'s inner wall 1506 inwards towards channel 1412*b*'s longitudinal centerline. A small opening 1508 remains in the center of ring 1504 to allow the ring to stretch open around an inserted object, yet the opening is generally small enough to prevent any significant fluid passage (e.g., insufflation gas escape). Thus the seals allow for insufflation (e.g., though an auxiliary channel in the port feature) before any instruments (e.g., cannulas) are inserted. The seals also improve the seal between the port feature and the cannulas when the port feature is flexed, and the channel shapes are consequently distorted, by cannula movement during surgery. In another implementation, a thin membrane is molded to fill the opening in the seal to provide a complete insufflation seal until an instrument is inserted into the channel. Such a membrane may be punctured during first cannula insertion by, e.g., an obturator.

FIG. 15C is a diagrammatic cross-sectional view taken at cut line B-B in FIG. 14A. Cut line B-B is taken through endoscope channel 1408's centerline, and so cut line B-B does not include the auxiliary channel 1414 or 1416 centerlines. FIG. 15C illustrates that in some implementations endoscope channel 1408 includes a seal 1508, and auxiliary channel 1414 includes a seal 1510, but auxiliary channel 1416 has no seal. FIG. 15C further illustrates that seals 1508 and 1510 are similar to seal 1502, although various seals may be used as described above.

Figure 15D:
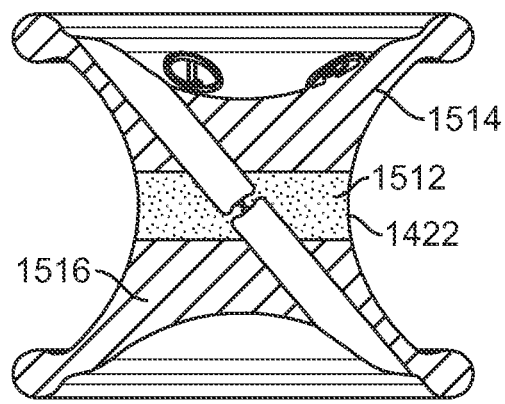
FIG. 15D is a diagrammatic cross-sectional view that illustrates an electrically conductive layer in a port feature.

FIG. 15D is a diagrammatic cross-sectional view taken at cut line A-A in FIG. 14, and it illustrates that in some implementations there is an electrically conductive silicone layer 1512 that extends horizontally across the middle of the port feature (e.g., at waist 1422, as shown). The conductive layer 1512 is shown spaced midway between the port feature's top and bottom surfaces, and so it incorporates seals as described herein. In other implementations the electrically conductive layer may be at another vertical position that does not incorporate the seals, or two or more electrically conductive layers may be used. In some implementations, the interior of the channels are necked down at the conductive layer but not necessarily configured as seals, so as to provide the necessary electrical contact between the conductive layer and the instrument. In one implementation, conductive layer 1512 is integrally molded with upper portion 1514 and lower portion 1516 of the port feature. The electrically conductive silicone may have a higher durometer value than the upper and lower portions due to the necessary additives, but since it is located at approximately the level of the cannula centers of motion, the higher stiffness does not significantly affect cannula movement as compared to a similar port feature without the electrically conductive layer. This electrically conductive layer forms an electrically conductive path between the patient's body wall, which is in contact with the port feature's outer surface, and the cannula and/or instrument that passes through the channel. This electrically conductive path provides a path to electrical ground during electrocautery.

Figure 15E:
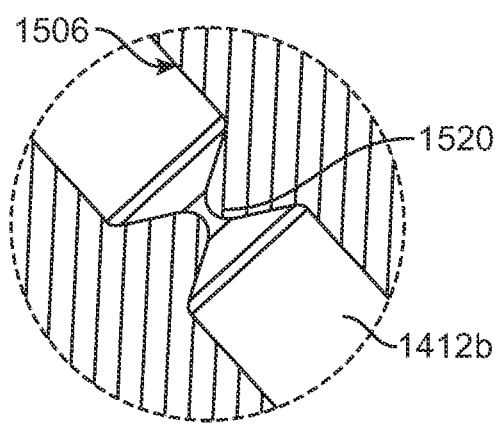
FIG. 15E shows a detail of another seal.

FIG. 15E is a detailed view of another example implementation of a seal that may be positioned within any one of the various channels in the port feature body. As shown in FIG. 15E, an annular projection 1520 is integrally molded with the port feature body and extends from channel 1412b's inner wall 1506 towards the channel's centerline. In the illustrative drawing, the projection's surfaces are at about a sixty degree angle to the channel wall, which allows an instrument to more easily align with and pass through the seal upon insertion. As with the seal implementation described above, the projection presses inwards around a cannula or other surgical instrument to provide an insufflation seal between the port feature body and the instrument. Since the projection's cross section is generally triangular with a rounded sealing surface against the instrument, and since the instrument's remote center of motion is generally positioned at or effectively at the seal, the seal moves with the instrument to provide a robust seal against the instrument as the instrument stretches the port feature body and slightly distorts the channel cross section during movement around the remote center of motion. A small opening (e.g., 0.014 inches for an instrument channel, 0.043 inches for an endoscope channel) remains in the center of the seal, and in some implementations a thin membrane is molded across this opening as described above.

Knowledgeable persons will understand that various other ways to implement an effective seal may be used. For example, in another seal implementation, an integrally molded resilient membrane fully blocks the channel, and the membrane is pierced the first time an object is inserted though the channel. The membrane then forms a seal with the object. In yet other implementations, a seal that is a separate piece may be inserted into the channel. For instance, an annular detent may be molded in channel wall 1506, and then a seal may be positioned and held in the detent.

Figure 16A:
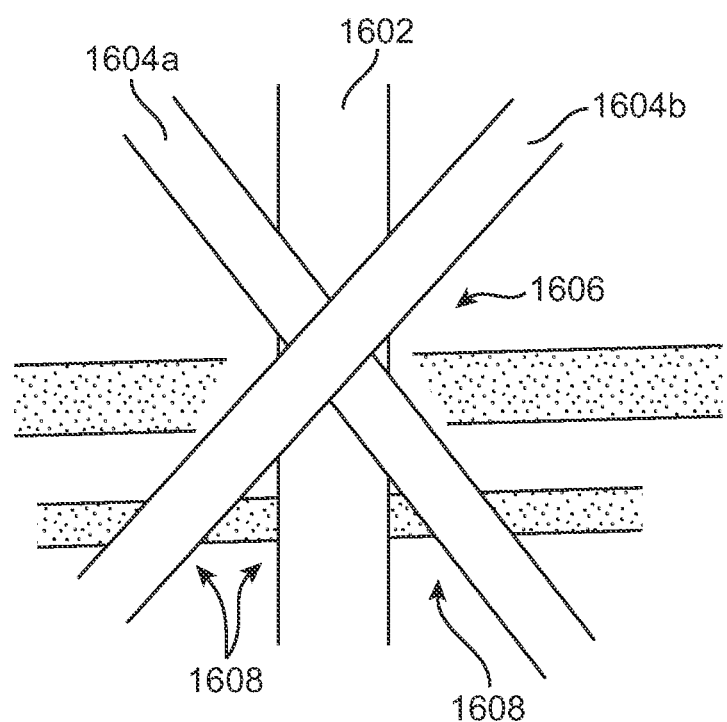
FIG. 16A is a diagrammatic view of various skin and fascia incisions.

As described above, in some cases port feature 1402 may be inserted through the entire body wall. In other cases, however, a single incision may not be made through the entire body wall. For example, a single incision may include a single percutaneous incision made at the umbilicus (e.g., in a Z shape) and multiple incisions in the underlying fascia. Accordingly, in some cases the port feature may be eliminated, and while each of the endoscope cannula and curved cannulas extend through the single percutaneous incision, the cannulas each pass through, and may be supported by, separate incisions in the fascia. FIG. 16A is a diagrammatic view that illustrates portions of endoscope cannula 1602, and left and right curved cannulas 1604a and 1604b passing though a single skin incision 1606, and then each through separate fascia incisions 1608. In some instances, operating room personnel may desire additional support for the cannulas in such a single percutaneous/multiple facial incision (e.g., while docking the inserted cannulas to their associated robotic manipulators). In such instances, a port configured similar to top portion 1514 (FIG. 15D) or to a combined top portion 1514 and conductive layer 1512 may be used.

Figure 16B:
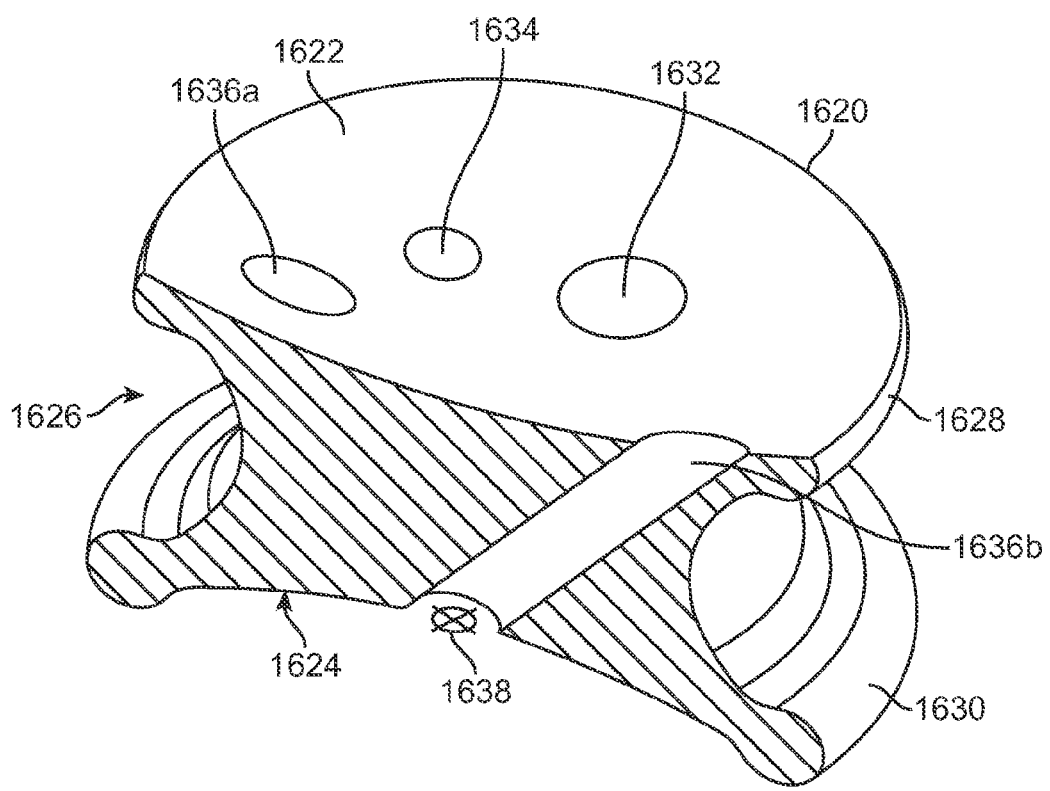
FIG. 16B is a diagrammatic perspective cross-sectional view of another port feature.

FIG. 16B is a diagrammatic perspective cross-sectional view of another port feature that may be used with a single skin incision/multiple fascia incisions procedure. Port feature 1620 is similar in configuration to port feature 1402, and features described above (e.g., orientation and port indicators, seals where applicable, soft resilient material, etc.) may apply to port feature 1620 as well. Port feature 1620 has a body with a generally cylindrical shape that includes a top surface 1622, a bottom surface 1624, and a narrowed sidewall waist 1626 between the top and bottom surfaces. Consequently, a top flange 1628 and a bottom flange 1630 are formed between the sidewalls and the top and bottom surfaces. During use, the skin is held in the waist 1626 between the upper and lower flanges, and the bottom surface 1624 and bottom flange 1630 rest on the fascia layer underlying the skin.

FIG. 16B further shows four illustrative ports that extend between the port feature's top and bottom surfaces. Channel 1632 is an endoscope channel, and channel 1634 is an auxiliary channel, similar to such channels described above with reference to port feature 1402. Likewise, channels 1636a and 1636b are angled instrument channels that are similar to such channels described above, channel 1636b angling from top right towards bottom left as shown, and channel 1636a angling from top left towards bottom right (hidden from view). Unlike port feature 1402's instrument channels, however, the centerlines of port feature 1620's instrument channels 1636a and 1636b do not extend across the port feature's vertical midline. Instead, the angled instrument channels stop at port feature 1620's midline, so that the remote centers of motion of the cannulas and instruments are positioned at the underlying fascia incisions (an illustrative center of motion position 1638 is illustrated). Thus it can be seen that the instrument channels' exit locations on the port feature's bottom surface may be varied so as to place the centers of motion at a desired location with reference to a patient's tissue.

Figure 17A:
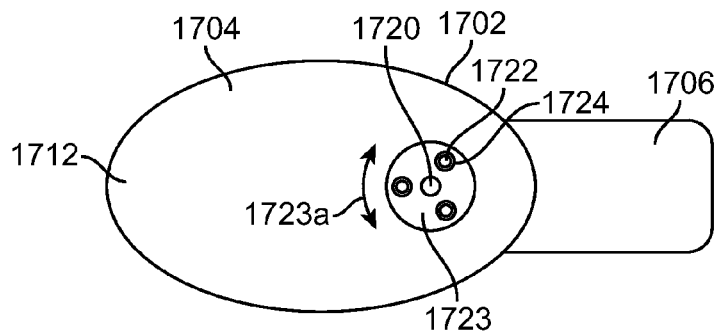
FIGS. 17A and 17B are diagrammatic views of yet another port feature.
Figure 17B:
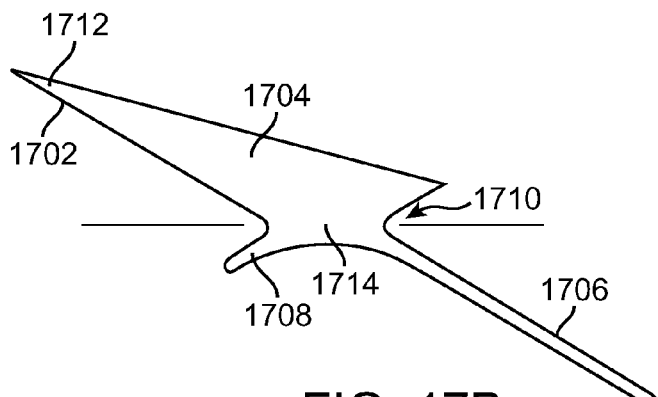

For some surgical procedures, the straight line between a single incision and a surgical site (e.g., between the umbilicus and the gall bladder) begins to approach being at an acute angle relative to the patient's coronal (frontal) plane. Consequently, the cannulas enter the single incision at a relatively small (acute) angle with reference to the skin surface, and the body wall twists and exerts a torsion on the cannulas/instruments or on the port. FIG. 17A is a diagrammatic top view, and FIG. 17B is a diagrammatic side view, of yet another port feature 1702 that may be used to guide and support two or more cannulas entering through a single incision. As shown in FIGS. 17A and 17B, port feature 1702 includes an upper funnel section 1704, a lower front tongue 1706, and a lower back tongue 1708. In some implementations, the funnel section and tongues are a single piece. Port feature 1702 may be formed of for example, relatively stiff molded plastic such as PEEK, polyetherimide (e.g., Ultem® products), polyethylene, polypropylene, and the like, so that port feature 1702 generally holds its shape during use. When positioned in an incision 1710, the lower tongues 1706,1708 are inside the body, and the funnel section 1704 remains outside the body. As shown in the figures, in some implementations funnel section 1704 is shaped as an oblique circular or elliptical cone, which reduces interference with equipment positioned over the funnel section when the port feature is twisted in the incision as described below. It can be seen that once in position, the distal end 1712 of funnel section 1704 may be pressed towards the skin surface. This action causes the waist section 1714 between the upper funnel portion and the lower tongues to twist in the incision, which effectively reorients the incision, and so it provides a more resistance free path to the surgical site. The front tongue prevents port feature 1702 from coming out of the incision during this twisting. In addition, pushing down on distal end 1712 of the funnel section raises the distal end 1716 of the front tongue. In some implementations, the front tongue may be sized and shaped to retract tissue as the distal end of the tongue is raised. The back tongue 1708 also helps keep port feature 1702 in the incision.

Port feature 1702 also includes at least two access channels to accommodate endoscope and instrument cannulas. As illustrated in FIG. 17A, in some implementations four example channels are within waist portion 1714. An endoscope cannula channel 1720 is placed in the middle of waist portion 1714, and three instrument cannula channels 1722 are positioned around endoscope cannula channel 1720. In some implementations the channels are formed in the same single piece as the funnel section and the tongues. In other implementations, the channels are formed in a cylindrical piece 1723 that is mounted to rotate as indicated by arrows 1723a in waist section 1714. In some implementations, instrument cannula channels 1722 are each formed in a ball joint 1724, which is positioned in waist section 1714 (e.g., directly, or in the cylindrical piece). The remote centers of motion of the cannulas are positioned in the ball joints, which then allow the cannulas to easily pivot within port feature 1702. In other implementations, the channels are configured to receive a ball that is affixed (e.g. press fit) to a cannula at the remote center of motion, and the cannula ball then pivots in the channel socket as a ball joint. In some implementations, the top and bottom surfaces of the waist section (e.g., the top and bottom surfaces of the cylindrical piece) may be beveled to allow for increased range of motion of the cannula moving in the ball joint. In some implementations, the endoscope cannula channel 1720 does not include a ball joint. In some implementations, an endoscope and/or instruments with rigid shafts may be routed through their respective channels without cannulas, with or without the use of ball joints as described above. In some implementations, seals may be positioned within one or more of the channels, as described above.

Figure 18A:
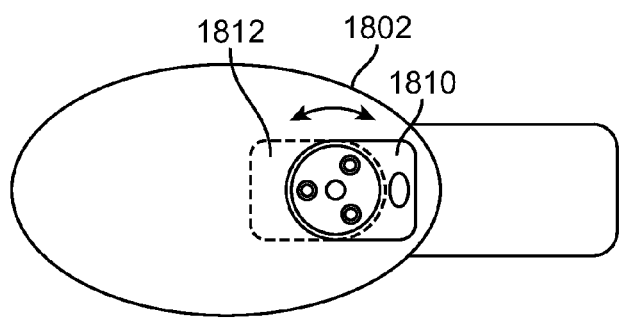
FIGS. 18A and 18B are diagrammatic views of yet another port feature.
Figure 18B:
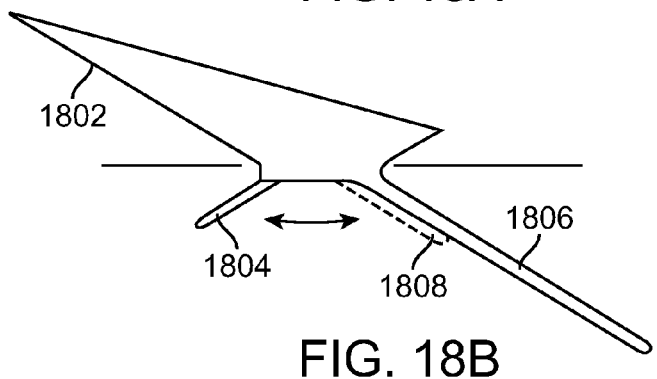

FIG. 18A is a diagrammatic top view, and FIG. 18B is a diagrammatic side view, of still another port feature 1802 that may be used to guide and support two or more cannulas entering through a single incision. Port feature 1802's basic configuration is similar to that of port feature 1702—e.g., the funnel section, front tongue, and channels are generally similar. In port feature 1802, however, back tongue 1804 may be rotated from a position aligned with front tongue 1806, as indicated by alternate position 1808, to a position opposite the front tongue, as shown in FIG. 18B. Therefore, back tongue 1804 may be made relatively longer than back tongue 1708 (FIG. 17B), and port feature 1802 can still be inserted into a single small incision. Back tongue 1804 is aligned with front tongue 1806 when port feature 1802 is positioned in the incision, and then it is rotated to the back position when the port feature is in place. In one implementation, back tongue 1804 is coupled to the rotating cylinder that contains the channels, as described above, and a tab 1810, located inside the funnel section, on the cylinder piece is rotated as indicated by the arrows from its alternate insertion position 1812 towards the front to position the back tongue for surgical use.

Aspects of the port features as described herein are not confined to use with one or more curved cannulas, and such port features may be used, for example, with straight instrument cannulas, rigid instrument shafts (with or without cannulas), and for both robotic and manual surgery.

Insertion Fixture

In multi-port minimally invasive surgery, the endoscope is typically the first surgical instrument to be inserted. Once inserted, the endoscope can be positioned to view other cannula and instrument insertions so that an instrument does not inadvertently contact and damage tissue. With a single incision, however, once an endoscope is inserted, the other cannulas and instruments are inserted at least initially outside the endoscope's field of view. And, for curved cannulas, it is difficult to ensure that a cannula tip will be moved directly into the endoscope's field of view without contacting other tissue. In addition, keeping the cannulas properly positioned and oriented as the robotic manipulators are adjusted and then coupled (docked) to the cannulas may require considerable manual dexterity involving more than one person. Therefore, ways of safely and easily inserting multiple instruments through a single incision are needed. During some surgical procedures, port features such as those described above may provide adequate ways of safely inserting multiple instruments. For example, a port feature (full or half-height) may be positioned in or on a body wall. The port feature's channels act as guides for cannula insertion, and once the cannulas are inserted, the port feature supports the cannulas for coupling to their associated robotic manipulators. Thus the port features as described above may act as insertion and stabilizing fixtures during the early stages of a surgical procedure, as described below. During other surgical procedures, or due to surgeon preference, other ways to safely insert and support multiple instruments may be used.

Figure 19A:
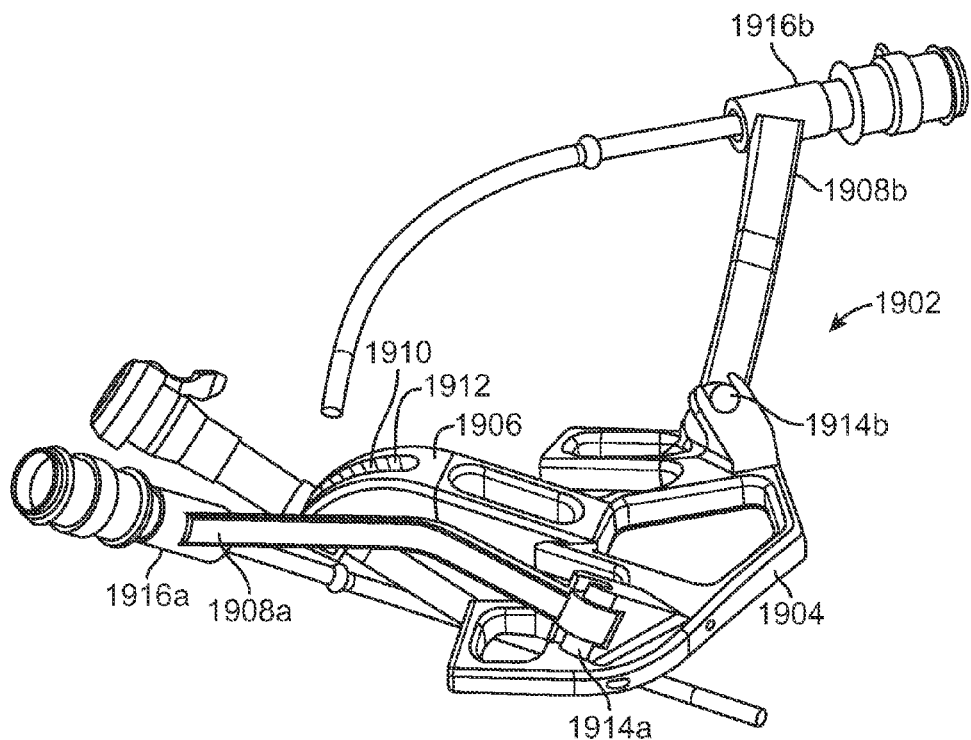
FIG. 19A is a perspective view of a cannula insertion/stabilizing fixture.

FIG. 19A is a perspective view of an example of a cannula insertion fixture 1902. As shown in FIG. 19A, insertion fixture 1902 is capable of guiding an endoscope cannula and two curved instrument cannulas into a single incision. Other implementations may guide more or fewer cannulas. Insertion fixture 1902 includes a base 1904, an endoscope cannula support arm 1906, and two instrument cannula support arms 1908a and 1908b. As shown in FIG. 19A, endoscope cannula support arm 1906 is rigidly mounted on base 1904, although in other implementations it may be pivotally mounted. The distal end of endoscope cannula support arm 1906 is curved downwards toward the plane of the base and contains an endoscope cannula support slot 1910 that functions as a mounting bracket for a cannula. Detents 1912 in support slot 1910 allow the endoscope cannula to be positioned and held at various angles.

FIG. 19A also shows that one instrument cannula support arm 1908a is pivotally mounted on base 1904 at hinge 1914a. An instrument cannula mount 1916a is at the distal end of cannula support arm 1908a and holds an illustrative instrument cannula (e.g., a curved cannula as described above). Cannula mount 1916a may include one or more mechanical key features to ensure that the cannula is held at a desired roll orientation, as described above. FIG. 19A shows the position of support arm 1908a with its associated cannula in an inserted position.

Figure 19B:
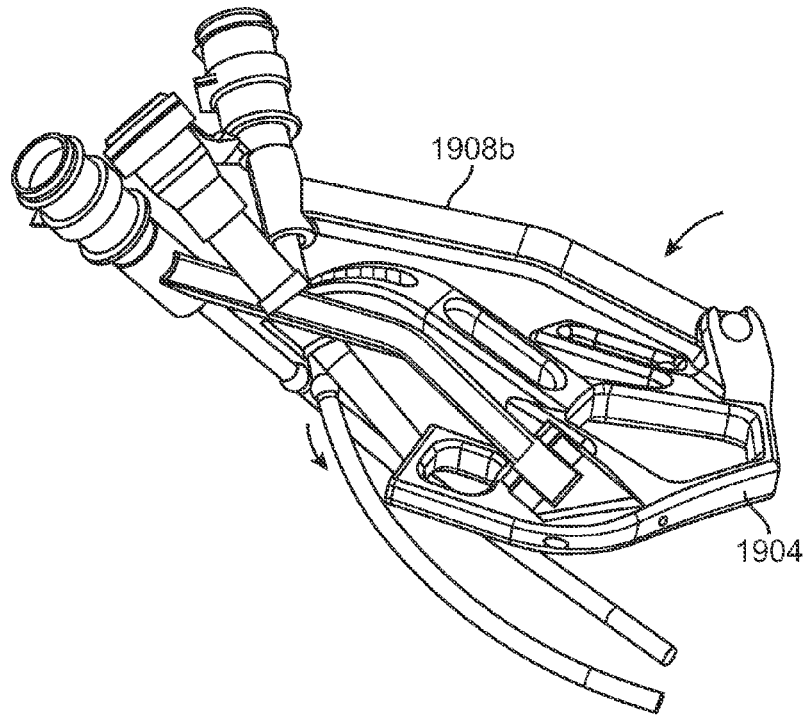
FIG. 19B is another perspective view of a cannula insertion/stabilizing fixture.

FIG. 19A further shows that another instrument cannula support arm 1908b is pivotally mounted on base 1904 at hinge 1914b, on a side opposite from support arm 1908a. Support arm 1908b includes an instrument cannula mount 1916b that is similar to cannula mount 1916a. FIG. 19A shows the position of support arm 1908b with its associated cannula before the cannula is inserted though the incision. The cannulas are held by the cannula mounts 1916a,1916b such that the axes of rotation for the hinges 1914a,1914b are at approximately the axes of curvature for the curved cannulas. Thus, as the support arms rotate at the hinges, the curved cannulas travel through approximately the same small area, which is aligned with a single incision or other entry port into the body. Referring to FIG. 19B, it can be seen that support arm 1908b has been moved to insert its associated cannula, which travels in an arc through the incision. In addition, the hinges 1914a,1914b may be oriented such that the two cannulas travel through slightly different areas in the incision in order to establish a desired clearance and arrangement among the various cannulas in the incision.

An illustrative use of the cannula insertion fixture is with the single percutaneous/multi-fascial incision, such as one described above. The surgeon first makes the single percutaneous incision. Next, the surgeon inserts a dissecting (e.g., sharp) obturator into an endoscope cannula and couples the endoscope cannula to the insertion fixture at a desired angle. At this time the surgeon may insert an endoscope through the endoscope cannula to observe further insertions, either mounting the endoscope cannula and endoscope to a robotic manipulator or temporarily supporting the endoscope by hand. The surgeon then many move the cannulas along their arc of insertion until they contact the body wall. Using a dissecting obturator, the surgeon may then insert each cannula through the fascia. The surgeon may then optionally remove the dissecting obturators from the cannulas and either leave the cannulas empty or insert blunt obturators. Then, the surgeon may continue to move the instrument cannulas to their fully inserted positions, with their distal ends positioned to appear in the endoscope's field of view. Once the cannulas are inserted, the robotic manipulators may be moved into position, and the instrument cannulas may then be mounted (docked) to their robotic manipulators. The insertion fixture is then removed, and flexible shaft instruments are inserted through the cannulas towards the surgical site under endoscopic vision. This illustrative insertion procedure is an example of many possible variations for using the insertion fixture to insert and support any number of cannulas through various incisions and body openings.

In some cases, an implementation of an insertion fixture may be used to support the cannulas while one or more manually operated instruments are inserted through the cannula(s) and used at the surgical site.

In some alternate implementations the insertion fixture may be simplified to only provide a way of holding the cannulas in a fixed position during docking to their associated manipulators. For example, this may be accomplished by first inserting the cannulas, then applying the fixture to the camera cannula, and then attaching the fixture to the curved cannulas. Once the inserted cannulas are coupled to the fixture, the patient side robot and its manipulators are moved to appropriate positions with reference to the patient. Then, while the fixture holds the camera cannula and the curved cannulas in place, each cannula is docked to its associated manipulator. Generally, the camera cannula is docked first.

Figure 19C:
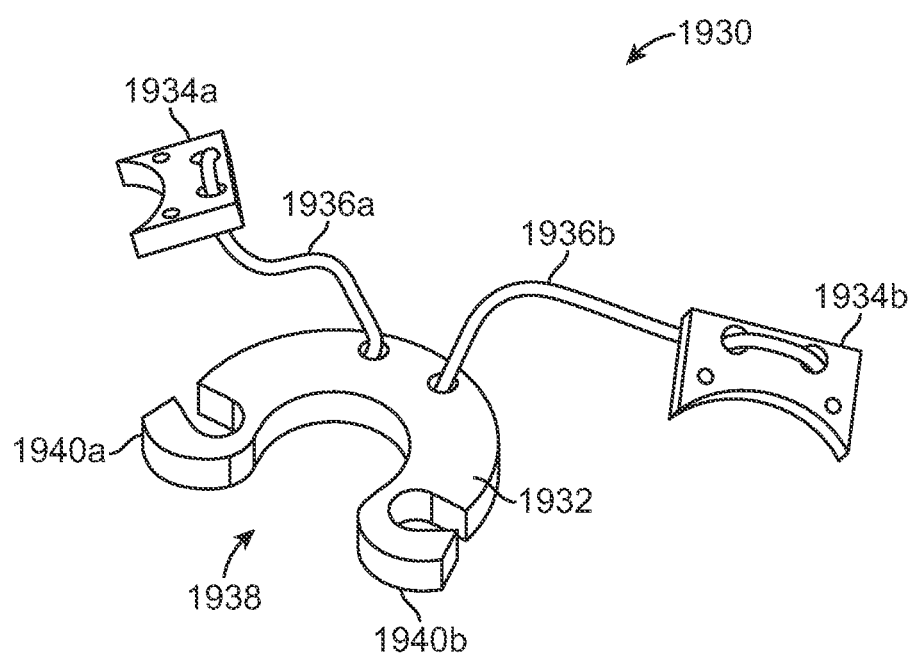
FIG. 19C is a diagrammatic perspective view of a cannula stabilizing fixture.

FIG. 19C is a diagrammatic perspective view of a cannula stabilizing fixture 1930. Fixture 1930 includes a base 1932 and two cannula holders 1934a and 1934b. Arm 1936a couples cannula holder 1934a to base 1932, and arm 1936b couples cannula holder 1934b to base 1932. Base 1932 is coupled to a stationary object, so that the fixture can support cannulas held at the ends of the arms. In one implementation, base 1932 is configured to receive an endoscope cannula in an opening 1938, and two integral spring clips 1940a and 1940b on either side of opening 1938 securely hold the base on the endoscope cannula (the endoscope cannula may be rigidly coupled to its associated ECM). Each cannula holder 1934a, 1934b is configured to hold an instrument cannula by receiving a key feature similar to the key feature described above with reference to FIG. 10A. Holes in the cannula holders receive pins 1036 as shown in FIG. 10A. Arms 1936a,1936b are in one illustrative implementation heavy, bendable aluminum wire covered by silicone tubing for corrosion resistance, and so the arms may be positioned and repositioned as desired. In other implementations, other materials such as stainless steel (without the need for a corrosion resistant cover or coating) and various rebendable/repositionable configurations (e.g., a rigidizable series of links as described above, a "gooseneck" type tube, etc.) may be used for the arms to provide sufficient cannula support. Each arm supports its associated cannula holder and instrument cannula so that the instrument cannulas are held stationary with reference to the endoscope cannula when all are positioned within a single skin incision. Knowledgeable persons will understand that many variations of this fixture are possible to hold the various cannulas effectively as a single unit in position during insertion and during docking to a robotic manipulator. For example, a single arm with cannula holders at either end may be used to support two cannulas with reference to one another.

Figure 20A:
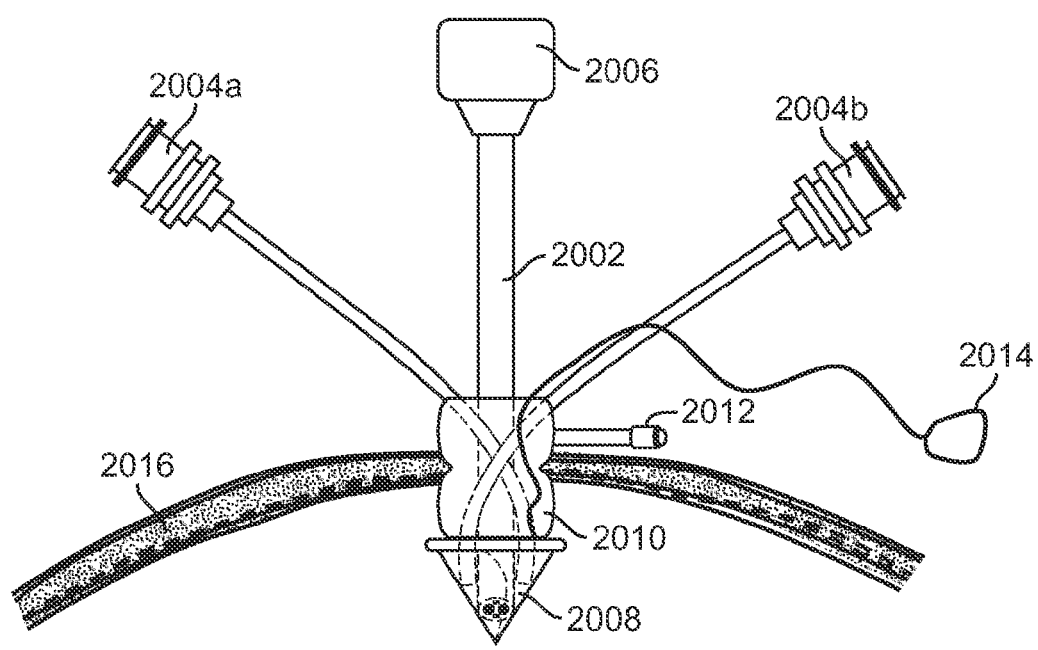
FIGS. 20A-20D are diagrammatic views that illustrate another way of inserting cannulas.

FIGS. 20A-20D are diagrammatic views that illustrate another way of inserting cannulas into a single incision. FIG. 20A shows for example an endoscope cannula 2002 and two curved cannulas 2004a and 2004b. In some instances, an endoscope 2006 may be inserted in endoscope cannula 2002. The distal ends of the cannulas, and if applicable the imaging end of an endoscope, are grouped together inside a cap 2008. In some implementations the cap 2008 may be a right circular cone made of a material sufficiently rigid to function as an obturator to penetrate a body wall. In some implementations, a surgeon first makes an incision, and then cap 2008 with the cannulas grouped behind it is inserted through the incision. In some instances the cap may be made of a transparent material that allows the endoscope to image the insertion path in front of the cap. In some implementations, cap 2008 may be grouped together with a port feature 2010, such as one described above or other suitable port feature. Thus in some instances the port feature may function as one or more of the cannulas for the endoscope and/or instruments. (As shown, port feature 2010 also illustrates that insufflation via an insufflation channel 2012 in any port feature may be provided in some implementations, although as described above insufflation may be provided in other ways, such as via one of the cannulas.) A tether 2014 is attached to cap 2008, and the tether extends to outside the body.

Figure 20B:
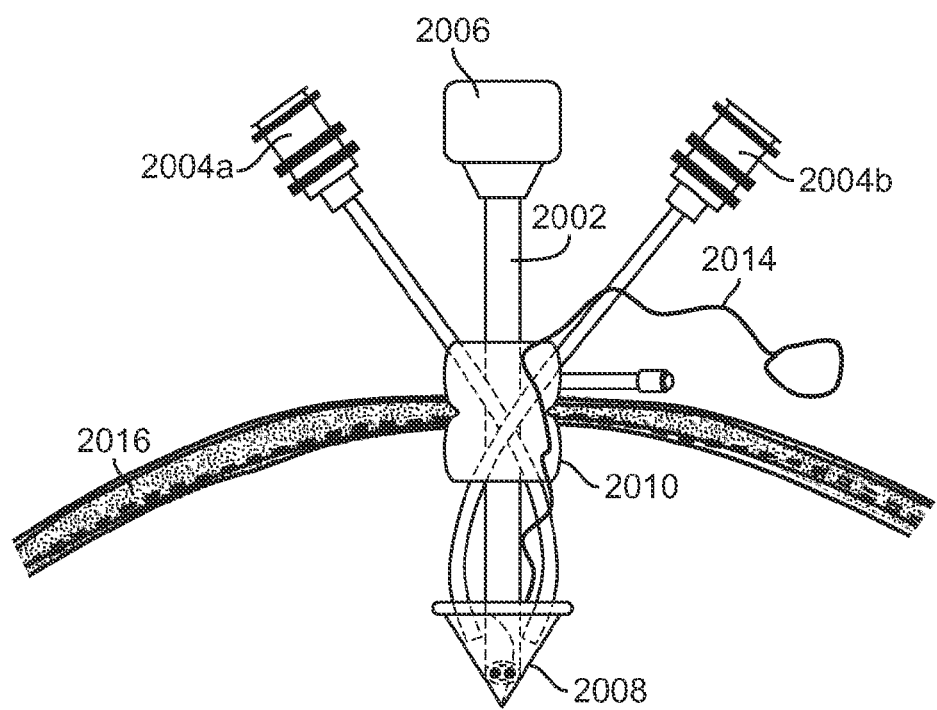

FIG. 20B shows that the distal ends of the cannulas (or instruments, as applicable) remain grouped in cap 2008 as it is inserted farther into the patient. As port feature 2010 remains secure in body wall 2016, the cannulas (or instruments, as applicable) slide through it in order to stay within cap 2008. In some instances the cap is moved farther inwards by pressing on one or more of the cannulas (or instruments, as applicable). For example, the endoscope cannula and/or cannula may be mounted on a robotic camera manipulator, and the manipulator may be used to insert the cap farther inwards.

Figure 20C:
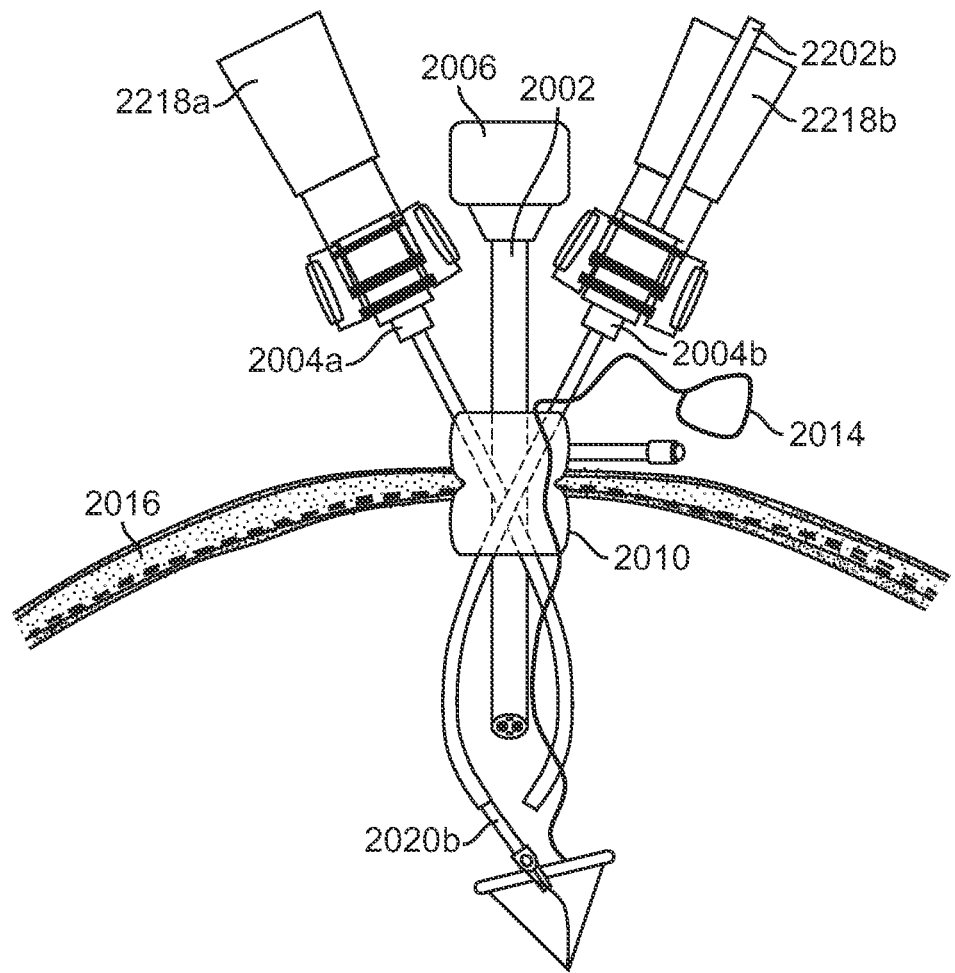
Figure 20D:
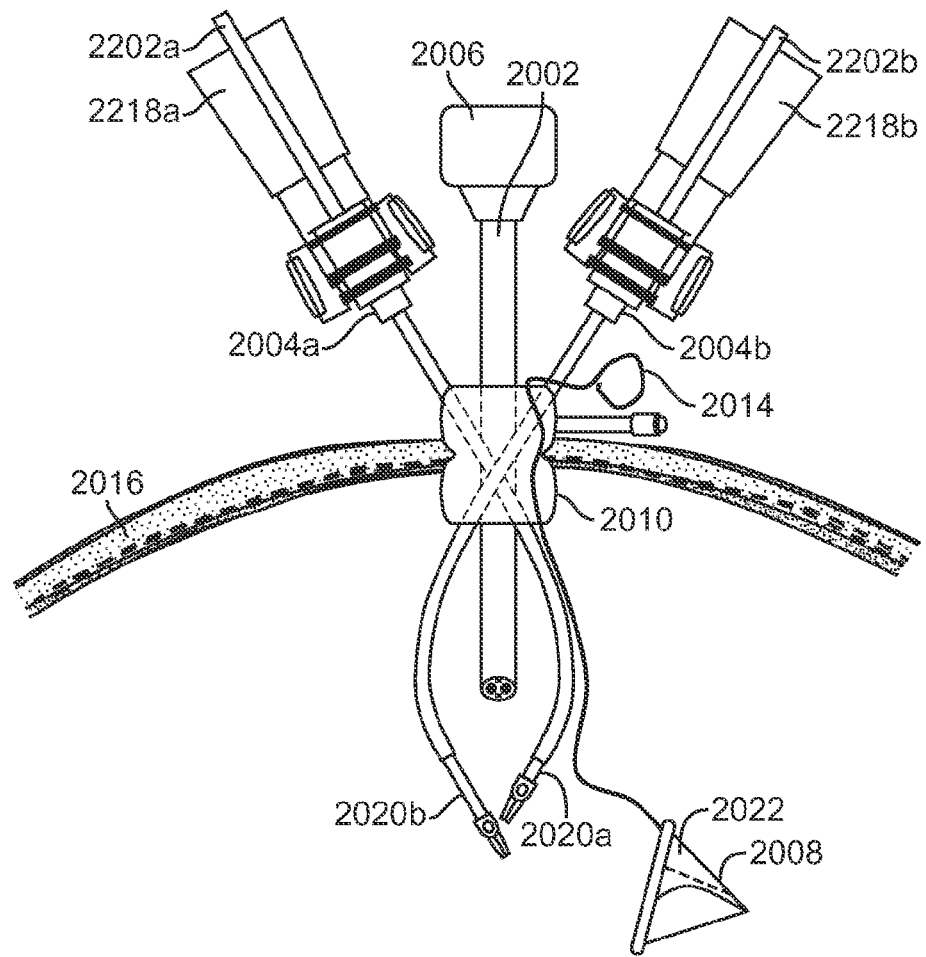

FIG. 20C shows that once the distal ends of the cannulas (or instruments, as applicable) have reached a desired depth, the cannulas may be coupled to their associated robotic manipulators (e.g., cannula 2004*a* to manipulator 2018*a* and cannula 2004*b* to manipulator 2018*b*). A surgical instrument may then be inserted through one of the instrument cannulas (e.g., surgical instrument 2020*b* through cannula 2004*b*, as shown) and mounted to an associated manipulator (e.g., manipulator 2018*b*). The surgical instrument may then be used to remove the cap from the distal ends of the cannulas (or other instruments, as applicable). FIG. 20D shows that the cap 2008 may be placed away from the surgical site inside the patient during a surgical procedure using the endoscope and both robotically controlled instruments 2020*a* and 2020*b*. Cap 2008 may optionally incorporate a specimen bag 2022 for specimen retrieval at the end of the procedure. This specimen bag may optionally incorporate a draw string to close the bag, and the specimen bag draw string may optionally be integral with the cap tether 2014. After surgery is complete and the instruments, cannulas, and port feature are removed, the cap 2008 (and optional bag) may be removed by pulling on tether 2014.

In one aspect, the various mount fixtures described herein are configured to aid insertion of and support a combination of one or more curved instrument cannulas and one or more straight instrument cannulas.

Control Aspects

Control of minimally invasive surgical robotic systems is known (see e.g., U.S. Pat. No. 5,859,934 (filed Jan. 14, 1997) (disclosing method and apparatus for transforming coordinate systems in a telemanipulation system), U.S. Pat. No. 6,223,100 (filed Mar. 25, 1998) (disclosing apparatus and method for performing computer enhanced surgery with articulated instrument), U.S. Pat. No. 7,087,049 (filed Jan. 15, 2002) (disclosing repositioning and reorientation of master/slave relationship in minimally invasive telesurgery), and U.S. Pat. No. 7,155,315 (filed Dec. 12, 2005) (disclosing camera referenced control in a minimally invasive surgical apparatus), and U.S. Patent Application Publication No. US 2006/0178559 (filed Dec. 27, 2005) (disclosing multi-user medical robotic system for collaboration or training in minimally invasive surgical procedures), all of which are incorporated by reference). Control systems to operate a surgical robotic system may be modified as described herein for use with curved cannulas and passively flexible surgical instruments. In one illustrative implementation, the control system of a da Vinci® Surgical System is so modified.

Figure 21:
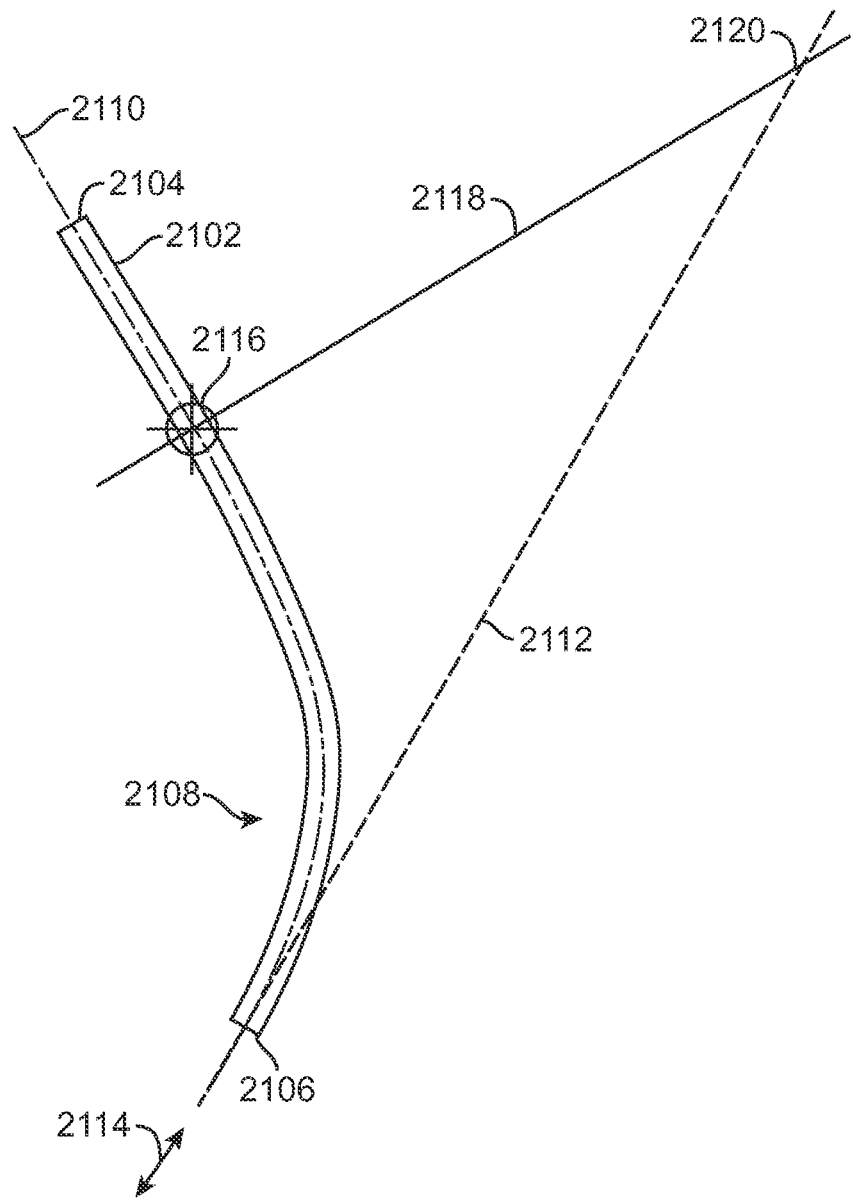
FIG. 21 is a diagrammatic view of a curved cannula and various reference axes.

FIG. 21 is a diagrammatic view of a curved cannula 2102, which has a proximal end 2104 that is mounted to a robotic manipulator, a distal end 2106, and a curved section (e.g., 60 degree bend) between the proximal and distal ends. A longitudinal centerline axis 2110 is defined between the proximal and distal ends of curved cannula 2102. In addition, an insertion and withdrawal axis 2112 is defined to include a centerline that extends along longitudinal axis 2110 in a straight line from the distal end of the curved cannula. Since the distal section (506*c*, FIG. 5) of the passively flexible instrument shaft is relatively stiff, it moves approximately along insertion and withdrawal axis 2112 as it extends out of the distal end of the curved cannula. Therefore the control system is configured to assume that the flexible shaft acts as a straight, rigid shaft having insertion and withdrawal axis 2112. That is, the instrument's I/O axis is taken to be the extended straight longitudinal centerline from the distal end of the curved cannula, and the system determines a virtual location of the instrument tip to be along the I/O axis 2112. This instrument I/O movement at the cannula's distal end is illustrated by double-headed arrow 2114. To prevent excess lateral movement in the section of the flexible shaft that extends beyond the cannula's distal end, in one implementation the extension distance is regulated by the control system software and may depend, e.g., on the stiffness of the flexible shaft's distal section for the particular instrument being used. And in one implementation, the control system will not allow the master manipulator to move the cannula or instrument until the instrument tip extends beyond the cannula's distal end.

The control system is also modified to incorporate kinematic constraints associated with the curved cannula. The motion of the instrument tip extending out of the cannula is described as if produced by a virtual serial kinematic chain of frames of reference, uniquely described by a set of Denavit-Hartenberg (DH) parameters. For example, boundary conditions for the cannula's distal end 2106 are defined as the tip position, tip orientation, and the length along the curved section. As another example, the boundary conditions are defined instead using the physical end of cannula, which includes the distal straight section of the cannula. Such boundary conditions are used to define the appropriate DH parameters. As illustrated in FIG. 21, a reference frame may be defined having an origin at a location along longitudinal axis 2110 (e.g., at the cannula's remote center of motion 2116, as shown). One axis 2118 of such a reference frame may be defined to intersect the extended I/O axis 2112 at a point 2120. A minimum distance can be determined between the reference frame's origin and the cannula's distal end 2106. Various different cannula configurations (e.g., length, bend angle, rotation when mounted on the manipulator, etc.) will have various associated kinematic constraints. For instrument I/O, however, the actual path length along the curved section is used instead of the minimum distance between the remote center of motion and the instrument's distal tip. Skilled persons will understand that various methods may be used to describe the kinematic constraints. For example, an alternate way of solving the problem is to incorporate the homogenous transformation that describes the geometry of the curved cannula into the serial kinematics chain explicitly.

As described above, there may be two or more curved cannulas with identical curvatures but various different lengths of distal straight sections. Since the DH parameters associated with each one of these cannulas are identical, the same intuitive control is maintained regardless of the length of each cannula's distal straight section. Therefore, since each of these cannulas can be treated identically for control purposes, a cannula-type detection feature as described above with reference to FIG. 10 can treat such cannulas as being a single cannula type.

Further modifications to the control system allow the surgeon to receive haptic feedback at the master manipulators (e.g., 122*a*,122*b* as shown in FIG. 1B). In various robotic surgical systems, the surgeon experiences a haptic force from servomotors in the master manipulators. For example, if the system senses (e.g., triggered by an encoder) that a slave side joint limit is reached or almost reached, then the surgeon experiences a force in the master that tends to keep the surgeon from moving the master manipulator in the slave side joint limit direction. As another example, if the system senses that an external force is applied to the instrument at the surgical site (e.g., by sensing excess motor current being used as the system attempts to maintain the instrument in its commanded position), then the surgeon may experience a force in the master manipulator that indicates a direction and magnitude of the external force acting on the slave side.

Haptic feedback in the master manipulators is used in one implementation of a control system used to provide the surgeon an intuitive control experience while using curved cannulas. For flexible instruments that do not have a wrist, the control system provides haptic forces at the master manipulators to prevent the surgeon from moving the multi-DOF master manipulator with a wrist motion. That is, master manipulator servomotors attempt to keep the master manipulator orientation stationary in pitch and yaw orientations as the surgeon changes the master manipulator position. This feature is similar to a feature used in current robotic surgical systems for instruments with straight, rigid shafts and no wrist. The system senses the instrument type (e.g., wristed, non-wristed) and applies the haptic feedback accordingly.

Haptic feedback is also used in one implementation to provide the surgeon a sense of an external force applied to various points in the instrument kinematic chain. Haptic feed back is provided to the surgeon for any sensed external force applied to the manipulator (e.g., as might occur if the manipulator collides with another manipulator) or to the straight proximal portion of the curved cannula. Since the cannula is curved, however, the system cannot provide proper haptic feedback for an external force applied to the cannula's curved section (e.g., by colliding with another curved cannula, either inside or outside the endoscope's field of view), because the system cannot determine the direction and magnitude of the applied force. In order to minimize such non-intuitive haptic feedback for this illustrative implementation, cannula collision is minimized by properly positioning the robotic manipulators and their associated cannulas, e.g., initially with the use of a fixture and/or during surgery with the use of a port feature, as described above. Similarly, the haptic feedback the system provides to the surgeon that is caused by external force applied to the portion of the instrument that extends from the cannula's distal end will not be accurate (unless experienced directly along the I/O axis). In practice, though, such forces on the distal ends of the instrument are low compared to the amount of friction and compliance in the instrument/transmission, and so any generated haptic feedback is negligible.

Figure 22:
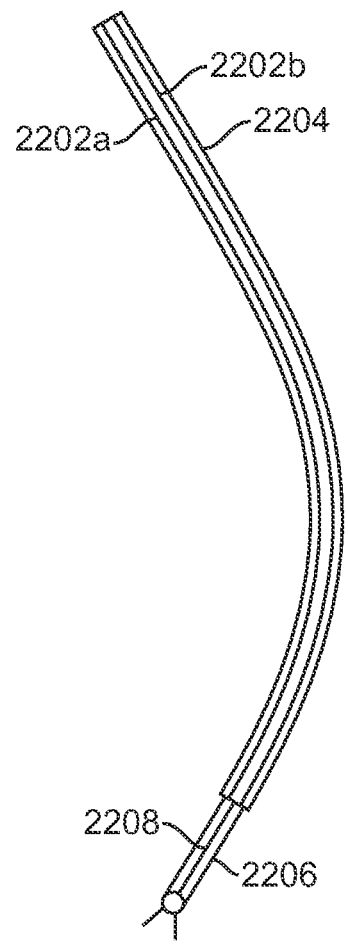
FIG. 22 is a diagrammatic view of a curved cannula and the distal end of a flexible instrument with associated optical fiber strain sensors.

In other implementations, however, force sensors may be used to provide the surgeon an accurate experience of an external force applied to either the cannula's curved section or the instrument's extended distal end. For example, force sensors that use optical fiber strain sensing are known (see e.g., U.S. Patent Application Pubs. No. US 2007/0151390 A1 (filed Sep. 29, 2006) (disclosing force torque sensing for surgical instruments), US 2007/0151391 A1 (filed Oct. 26, 2006) (disclosing modular force sensor), US 2008/0065111 A1 (filed Sep. 29, 2007) (disclosing force sensing for surgical instruments), US 2009/0157092 A1 (filed Dec. 18, 2007) (disclosing ribbed force sensor), and US 2009/0192522 A1 (filed Mar. 30, 2009) (disclosing force sensor temperature compensation), all of which are incorporated herein by reference). FIG. 22 is a diagrammatic view of a curved cannula and the distal portion of a flexible instrument, and it shows that in one illustrative implementation, one or more force sensing optical fibers $2202a,2202b$ may be positioned (e.g., four fibers equally spaced around the outside) on curved cannula 2204 (strain sensing interrogation and strain determination components for the optical fibers are omitted for clarity). Similarly, the distal section 2206 of the flexible instrument may incorporate (e.g., routed internally) one or more strain sensing optical fibers 2208 that sense bend at a location on, or the shape of the distal section, and the amount of displacement and the location with reference to the cannula's distal end may be used to determine the external force on the extended instrument.

Figure 23:
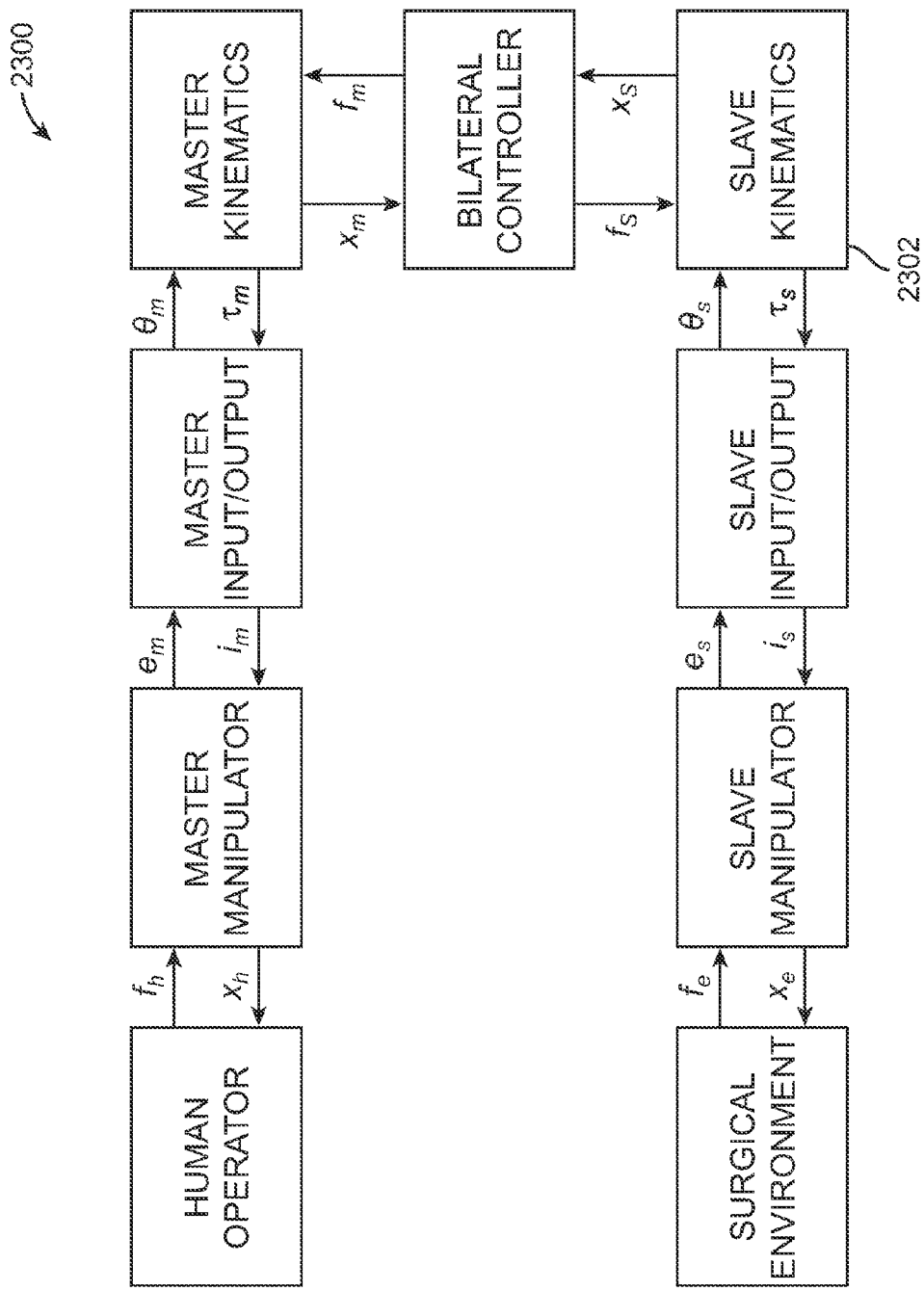
FIG. 23 is a diagrammatic view of a control system architecture.

FIG. 23 is a diagrammatic view of a control system architecture 2300 for a teleoperated robotic surgical system with telepresence. As shown in FIG. 23, $f_h$=human forces
$x_h$=master position
$e_{m,s}$=encoder values (master, slave)
$i_{m,s}$=motor currents (master, slave)
$\theta_{m,x}$=joint positions (master, slave)
$\tau_{m,s}$=joint torques (master, slave)
$f_{m,s}$=Cartesian forces (master, slave)
$x_{m,s}$=Cartesian positions (master, slave)
$f_e$=environmental forces
$x_e$=slave position In one implementation, control system modifications as described above are done in the "Slave Kinematics" portion 2302 of control system architecture 2300. Additional details describing control system architecture 2300 are found, e.g., in the references cited above. Control system 2300 data processing may be implemented in electronic data processing unit 142 (FIG. 1C), or it may be distributed in various processing units throughout the surgical system.

Referring to FIGS. 11A and 11B, together with FIG. 1B and FIG. 4C, it can be seen that in many implementations, the instrument end effector actuated by the "left" robotic manipulator appears in the right side of the endoscope's field of view, and the instrument end effector actuated by the "right" robotic manipulator appears in the left side of the endoscope's field of view. Accordingly, to preserve intuitive control of the end effectors as viewed by a surgeon at the surgeon's console display, the right master manipulator controls the "left" robotic manipulator, and the left master manipulator controls the "right" robotic manipulator. This configuration is opposite the configuration typically used with straight surgical instruments, in which the robotic manipulator and its associated instrument are both positioned on the same side with reference to a vertical division of the endoscope's field of view. During use with curved cannulas, the robotic manipulator and its associated instrument are positioned on opposite sides of the endoscope reference frame. This would not apply, however, to the use of certain compound curve cannulas, such as is illustrated by FIG. 13 and associated text.

Thus various implementations of the control system allow the surgeon to experience intuitive control of the instrument end effectors and the resulting telepresence even without the use of an instrument wrist that provides pitch and yaw movements. Movement of a master manipulator (e.g., 122a, FIG. 1B) results in a corresponding movement of either the distal end of the associated curved cannula (for pitch and yaw movements at the surgical site) or the instrument end effector (for I/O, roll, and grip (or other end effector DOF's)). Accordingly, a surgeon's hand motion at a master control can be reasonably well approximated with a corresponding slave movement at the surgical site without the use of a separate wrist mechanism in the instrument. The instrument tips move in response to master manipulator position changes, not master manipulator orientation changes. The control system does not interpret such surgeon wrist-motion orientation changes.

In some implementations, the control system of a surgical robotic system may be configured to automatically switch between the use of straight cannulas with associated straight shaft instruments, and the use of curved cannulas with associated flexible shaft instruments. For example, the system may sense that both a curved cannula and a flexible shaft instrument are mounted on a manipulator, as described above with reference to FIG. 6 and FIG. 10, and so switch to a control mode associated with the curved cannula and the flexible instrument. If however, the system senses a straight cannula and flexible instrument mounted on the manipulator, then this sensing may trigger an illegal state, and the system will not operate.

In some implementations for surgical robotic systems with multiple robotic manipulators, the control software can allow the surgeon to use a mix of curved cannulas of various different shapes, flexible shaft instruments of various different lengths, together with straight cannulas and rigid straight-shaft instruments. The tip motion of all such instruments will appear alike, and so the surgeon will experience intuitive control because of the automatic handling of the cannula kinematic constraints as described above.

We claim:

1. A surgical port feature comprising:
 a port feature body comprising a top surface, a bottom surface, and an outer sidewall that extends between the top and the bottom surfaces;
 a first channel that extends in a first direction straight from the top surface to the bottom surface;
 a second channel that extends in a second direction straight from the top surface to the bottom surface; and
 an electrically conductive path that extends from the outer sidewall to an inner wall portion of at least one of the first channel and the second channel, wherein the electrically conductive path is disposed relative to less electrically conductive portions of the port feature body to provide a predefined electrically conductive path through the port feature body to an electrical ground;
 wherein the first and second directions are different from one another.

2. The surgical port feature of claim 1:
 wherein the first channel extends at an acute angle from the top surface to the bottom surface; and
 wherein the second channel extends vertically from the top surface to the bottom surface.

3. The surgical port feature of claim 2:
 wherein the first channel extends in the first direction across a vertical midsection of the port feature body.

4. The surgical port feature of claim 2:
 wherein the first channel intersects the bottom surface at about a vertical midline of the port feature body.

5. The surgical port feature of claim 2:
 wherein the second channel is configured to receive an endoscope or a manually operated surgical instrument.

6. The surgical port feature of claim 1:
 wherein the first channel extends at a first acute angle from the top surface to the bottom surface; and
 wherein the second channel extends at a second acute angle from the top surface to the bottom surface.

7. The surgical port feature of claim 6:
 wherein the first and second acute angles are substantially equal; and
 wherein the first and second directions are substantially opposite to one another.

8. The surgical port feature of claim 6:
 wherein the first channel extends in the first direction across a vertical midsection of the port feature body; and
 wherein the second channel extends in the second direction across the vertical midsection of the port feature body.

9. The surgical port feature of claim 6:
 wherein the first channel and the second channel each intersect the bottom surface at about a vertical midline of the port feature body.

10. The surgical port feature of claim 6:
 wherein the second channel is configured to receive an endoscope or a manually operated surgical instrument.

11. The surgical port feature of claim 1 further comprising:
 an endoscope channel that extends vertically straight from the top surface to the bottom surface; and
 an auxiliary channel that extends vertically straight from the top surface to the bottom surface;
 wherein the endoscope channel and the auxiliary channel are each offset from the vertical centerline of the port feature.

12. The surgical port feature of claim 1 further comprising:
 a seal positioned in the first channel;
 wherein the seal is integrally molded with the port feature body.

13. The surgical port feature of claim 12:
 wherein the seal comprises an annular projection from a sidewall of the first channel inwards towards the center of the first channel; and
 wherein the annular projection comprises a generally triangular cross section with a rounded tip oriented towards the center of the first channel.

14. The surgical port feature of claim 12:
 wherein the seal comprises a membrane that covers a center opening in the seal; and
 wherein the membrane prevents gas from passing through the first channel.

15. The surgical port feature of claim 12, wherein the electrically conductive path comprises at least a portion of the seal.

16. The surgical port feature of claim 1,
 wherein the outer sidewall comprises a waisted shape such that a top circumferential lip is defined between the top surface and the outer sidewall and a bottom circumferential lip is defined between the bottom surface and the outer sidewall.

17. The surgical port feature of claim 1,
 wherein the electrically conductive path comprises an electrically conductive layer underlying the top surface.

18. The surgical port feature of claim 1:
 wherein the port feature body is a molded single piece.

19. The surgical port feature of claim 1:
 wherein the port feature body comprises a material comprising a durometer value in the range from about 40 Shore 00 to about 15 Shore A.

20. The surgical port feature of claim 1 further comprising:
 a port orientation feature that indicates a proper orientation of the port feature body within an opening into a patient's body with reference to a surgical site within the patient's body.

21. The surgical port feature of claim 1, wherein the electrically conductive path extends substantially in a transverse direction from the outer sidewall to at least one of the first channel and the second channel.

22. The surgical port feature of claim 1, wherein the electrically conductive path extends from the outer sidewall to a necked down region of at least one of the first channel and the second channel.

23. The surgical port feature of claim 1, wherein the electrically conductive path comprises silicone.

24. The surgical port feature of claim 1, wherein, in a position of insertion into a surgical incision site, the electrically conductive path is disposed to be in electrical communication with an electrical ground.

25. A surgical port feature comprising:
- a top surface, a bottom surface, and an outer sidewall that extends from the top surface to the bottom surface;
- a first channel that extends from the top surface to the bottom surface; and
- an electrically conductive path that extends from the outer sidewall to the first channel, wherein the electrically conductive path is disposed relative to less electrically conductive portions of the port feature to provide a predefined electrically conductive path through the port feature to an electrical ground.

26. The surgical port feature of claim 25, wherein the first channel is configured to receive an endoscope or a manually operated surgical instrument.

27. The surgical port feature of claim 25, wherein the first channel extends straight from the top surface to the bottom surface.

28. The surgical port feature of claim 25, further comprising:
- a second channel that extends from the top surface to the bottom surface,
- wherein the first channel and the second channel extend in differing directions from each other.

29. The surgical port feature of claim 28, wherein at least one of the first channel and the second channel extends vertically from the top surface to the bottom surface.

30. The surgical port feature of claim 28, wherein at least one of the first channel and the second channel extends at an acute angle from the top surface to the bottom surface.

31. The surgical port feature of claim 28, wherein the port feature further comprises:
- a seal positioned in at least one of the first channel and the second channel;
- wherein the electrically conductive path comprises at least a portion of the seal.

32. The surgical port feature of claim 25, wherein the channel comprises a necked down region sized to seal around a surgical instrument passing through the region.

33. The surgical port feature of claim 32, wherein the electrically conductive path extends from the outer sidewall to the necked down region.

34. The surgical port feature of claim 25, wherein the port feature and the electrically conductive path comprise a molded single piece structure.

35. The surgical port feature of claim 34, wherein the port feature and electrically conductive path comprise silicone.

36. The surgical port feature of claim 25, wherein the electrically conductive path comprises a plurality of electrically conductive paths.

37. An apparatus comprising:
- a port feature body having a top surface, a bottom surface, an outer sidewall that extends from the top surface to the bottom surface, a channel that extends from the top surface to the bottom surface, and an electrically conductive path that extends from the outer sidewall to the channel, wherein the electrically conductive path is disposed relative to less electrically conductive portions of the port feature body to provide a predefined electrically conductive path through the port feature body to an electrical ground; and
- a surgical instrument positioned in the channel to be in electrical contact with the electrically conductive path.

38. The apparatus of claim 37, wherein the electrically conductive path of the port feature body comprises an electrically conductive layer underlying the top surface.

39. The apparatus of claim 37, wherein the port feature body further comprises:
- a seal positioned in the channel; and
- wherein the electrically conductive path comprises at least a portion of the seal.

40. The apparatus of claim 37, wherein the electrically conductive path of the port feature body extends substantially in a transverse direction from the outer sidewall to the channel.

41. The apparatus of claim 40, wherein the channel comprises a necked down region sized to seal around the surgical instrument; and
- wherein the electrically conductive path extends from the outer sidewall to the necked down region.

* * * * *